United States Patent
McMillan et al.

(10) Patent No.: US 10,798,339 B2
(45) Date of Patent: Oct. 6, 2020

(54) TELEPRESENCE MANAGEMENT

(71) Applicant: RoboRep Inc., Aurora, Ontario (CA)

(72) Inventors: Steven Robert McMillan, Aurora (CA); Andrew Hogue, Courtice (CA)

(73) Assignee: RoboRep Inc., Aurora, Ontario (CA)

( * ) Notice: Subject to any disclaimer, the term of this patent is extended or adjusted under 35 U.S.C. 154(b) by 0 days.

(21) Appl. No.: 16/616,327

(22) PCT Filed: Jun. 13, 2018

(86) PCT No.: PCT/CA2018/050711
§ 371 (c)(1),
(2) Date: Nov. 22, 2019

(87) PCT Pub. No.: WO2018/227290
PCT Pub. Date: Dec. 20, 2018

(65) Prior Publication Data
US 2020/0120308 A1    Apr. 16, 2020

Related U.S. Application Data

(60) Provisional application No. 62/519,374, filed on Jun. 13, 2017.

(51) Int. Cl.
| | |
|---|---|
| *H04N 7/15* | (2006.01) |
| *G16H 80/00* | (2018.01) |
| *G06F 30/12* | (2020.01) |
| *G06F 3/01* | (2006.01) |
| *G06F 3/038* | (2013.01) |
| *G06K 7/10* | (2006.01) |

(Continued)

(52) U.S. Cl.
CPC ............. *H04N 7/15* (2013.01); *G06F 3/017* (2013.01); *G06F 3/0386* (2013.01); *G06F 30/12* (2020.01); *G06K 7/10386* (2013.01); *G16H 80/00* (2018.01); *H04N 5/23206* (2013.01); *H04N 7/147* (2013.01); *H04N 2007/145* (2013.01)

(58) Field of Classification Search
CPC . H04N 7/15; H04N 7/14; H04N 5/232; G06F 3/01; G06F 3/038; G06F 30/12; G16H 80/00; G06K 7/10
USPC ................. 348/14.01–14.16; 705/4; 434/262
See application file for complete search history.

(56) References Cited

U.S. PATENT DOCUMENTS

| | | |
|---|---|---|
| 5,258,837 A | 11/1993 | Gormley |
| 5,625,410 A | 4/1997 | Washino et al. |

(Continued)

OTHER PUBLICATIONS

Matsuda et al., "ScalableBody: A Telepresence Robot Supporting Socially Acceptable Interactions and Human Augmentation through Vertical Actuation", UIST '16 Adjunct Proceedings of the 29th Annual Symposium on User Interface Software and Technology; pp. 103-105; Published Oct. 16, 2016.

(Continued)

*Primary Examiner* — Melur Ramakrishnaiah

(57) ABSTRACT

A telepresence apparatus includes a first computer assembly configured to interface with a first memory assembly configured to tangibly store programmed coded instructions. The programmed coded instructions are configured to urge the first computer assembly to compute whether to suspend transmission of an aspect of a telepresence data unit to the second computer assembly via the communication network depending on a match made between a user gesture signal and a predetermined user gesture.

22 Claims, 12 Drawing Sheets

(51) Int. Cl.
*H04N 5/232* (2006.01)
*H04N 7/14* (2006.01)

(56) References Cited

U.S. PATENT DOCUMENTS

| | | | |
|---|---|---|---|
| 5,891,158 A * | 4/1999 | Manwaring | A61B 90/14 600/102 |
| 6,325,756 B1 | 12/2001 | Webb et al. | |
| 7,312,766 B1 | 12/2007 | Edwards | |
| 7,819,885 B2 | 10/2010 | Cooper | |
| 8,670,017 B2 | 3/2014 | Stuart et al. | |
| 8,758,352 B2 | 6/2014 | Cooper et al. | |
| 8,860,773 B2 | 10/2014 | Clapis et al. | |
| 8,897,920 B2 | 11/2014 | Wang et al. | |
| 8,988,483 B2 | 3/2015 | Schwartz | |
| 9,044,863 B2 | 6/2015 | Mead et al. | |
| 9,167,205 B2 | 10/2015 | Hines et al. | |
| 9,305,218 B2 | 4/2016 | Lewis et al. | |
| 9,440,356 B2 | 9/2016 | Sutherland et al. | |
| 2004/0030245 A1 * | 2/2004 | Noble | G09B 23/28 600/426 |
| 2006/0142739 A1 * | 6/2006 | DiSilestro | A61B 90/90 606/1 |
| 2009/0248041 A1 * | 10/2009 | Williams | A61B 8/12 606/130 |
| 2009/0300540 A1 * | 12/2009 | Russell | G06F 3/0483 715/783 |
| 2010/0100240 A1 | 4/2010 | Wang et al. | |
| 2010/0318380 A1 | 12/2010 | Feess et al. | |
| 2011/0288682 A1 | 11/2011 | Pinter et al. | |
| 2012/0075464 A1 | 3/2012 | Derenne et al. | |
| 2013/0002800 A1 * | 1/2013 | Mock | H04N 7/142 348/14.03 |
| 2014/0349580 A1 * | 11/2014 | Chen | G06F 1/1626 455/41.2 |
| 2014/0369491 A1 * | 12/2014 | Kloberdans | H04M 1/6008 379/421 |
| 2015/0120312 A1 | 4/2015 | Hyde et al. | |
| 2015/0269229 A1 | 9/2015 | Shenoy et al. | |
| 2016/0135234 A1 | 5/2016 | Nakazawa et al. | |
| 2016/0180743 A1 * | 6/2016 | Ahmad | G06F 19/3418 434/262 |
| 2016/0314711 A1 | 10/2016 | Grubbs | |
| 2016/0323350 A9 | 11/2016 | Ralph et al. | |
| 2017/0157514 A1 | 6/2017 | Nakano et al. | |
| 2017/0344121 A1 * | 11/2017 | Blanco | H04W 76/10 |
| 2017/0344717 A1 * | 11/2017 | Houlihan | G16H 40/67 |
| 2018/0054561 A1 * | 2/2018 | Morita | H04N 5/23203 |

OTHER PUBLICATIONS

Lepage et al., "Telehomecare telecommunications framework—From remote patient monitoring to video visits and robot telepresence", Engineering in Medicine and Biology Society (EMBC), 2016 IEEE 38th Annual International Conference, pp. 3269-3272, Published Aug. 2016.

Takacs et al., "Origins of surgical robotics: From space to the operating room", Acta Polytechnica Hungarica, vol. 13(1), pp. 13-30, published 2016.

Adel El Hamad, International Search Report for PCT/CA2018/050711, published Dec. 20, 2018.

Adel El Hamad, Written Opinion for PCT/CA2018/050711, published Dec. 20, 2018.

Adel El Hamad, Search Strategy for PCT/CA2018/050711, published Dec. 20, 2018.

* cited by examiner

TELEPRESENCE MANAGEMENT

TECHNICAL FIELD

This document relates to the technical field of (and is not limited to) a telepresence apparatus (and method therefor).

BACKGROUND

A telepresence apparatus (also called a tele-robotic system) is a type of videoconferencing system.

SUMMARY

It will be appreciated that there exists a need to mitigate (at least in part) at least one problem associated with the existing conferencing systems (also called the existing technology). After much study of the known systems and methods with experimentation, an understanding of the problem and its solution has been identified and is articulated as follows:

Known telepresence systems are configured to allow a first person (user) who is located in a first location to feel as if they were present (to a second person located in a second location), to give the appearance of being present, or to have an effect, at a place other than their true physical location (that is, the first location). The known telepresence system is configured to allow the second person to be comfortable interacting with a computer in a way that may be more akin to interacting with the first person (a physical person). The known telepresence apparatus is configured to require that a user's (located at a second location) senses are provided with stimuli that provide a sensation of the first person being present at the second location (when the first person is, in fact, not actually physically at the second location). The first person may be given the ability to impart an effect on the second location. In this case, the user's position, movements, actions, voice, etc. (located in the first location) may be sensed, transmitted and duplicated in the second location to bring about this effect. Telepresence information may be transmitted (communicated via a communication network between computer systems) in both directions between the first user who is located at the first location and the second user who is located at a second location (that is located remotely from the first location). Telepresence via video may deploy greater technical sophistication and improved fidelity of both sight and sound than in known videoconferencing. Technical advancements in mobile collaboration have also extended the capabilities of videoconferencing beyond the boardroom for use with hand-held mobile devices (thereby enabling collaboration independent of location).

It will be appreciated that the meaning of a user of a telepresence apparatus is a person that may be any participant associated with the telepresence apparatus (whether the participant is located at the place of transmission, such as a first location, or at the place of reception, such as the second location, of the telepresence data unit). For the case where the user is located at the first location, then the user may include surgical staff, a nurse, a doctor, etc. For the case where the user is located at the second location, then the user may include a clinical expert (or a representative from a medical device company) that may provide assistance to the surgical staff located in the first site. Preferably, the first location is defined as a local site (in which the surgical staff is located or positioned), and the second location is defined as the remote site in which the clinical expert is positioned.

For instance, a telepresence apparatus may be very desirable in an operating room (surgical setting) for performing a variety of surgeries, such as orthopedic (also spelled orthopaedic) surgeries, etc.

For instance, due to the complexity of a surgery, it may be desirable to have a surgery support representative (a person) physically present in the operating room.

For instance, due to the complexity of orthopaedic surgeries, it may be desirable to have an orthopaedic surgery support representative (a person) physically present in the operating room (however, this option may be prohibitively expensive to implement). Moreover, it may be logistically difficult to provide support representatives (surgical support people) that have adequate clinical expertise for each surgery (or the case where the support representative is required to be physically present in each surgical room during surgery).

The support representative may provide real-time support (in situ, in an operating room) on how to properly assemble, use, and install medical devices and/or medical instruments, and conduct the surgery. However, the need for a physical presence of the support representative may limit the ability of the support representative to service multiple operating rooms at the same time.

There are known systems configured to provide (facilitate) remote communication and support, in which these known systems may include the SKYPE (TRADEMARK) software (manufactured and/or supplied by MICROSOFT CORP., headquartered in the U.S.A.), etc., and any equivalent thereof, instant messaging software applications, cellular phones, and other systems configured to facilitate bidirectional exchange (exchanging communication) of video and audio during a conference call.

However, these known systems may serve only a single aspect of remote communication (such as audio or video). Moreover, these known systems are not configured to allow for an individual to demonstrate a procedure or provide additional information or additional non-verbal information. The additional information may include, for instance, a pre-made video, a rendered (pre-rendered) animation, a real-time animation of a medical procedure, etc. It will be appreciated that additional information may also include technical specifications about sterile prostheses, sizing interchangeability charts, indications and contraindications for particular implants, etc., (and any equivalent thereof).

Furthermore, these known systems are not configured to allow an individual to augment or annotate (with text or other means) the chat, a video feed, or a visual communication. For example, while participating in a video conference call, participants may not add information (text, images, media, etc.) to areas of a video. Therefore, it may be desirable to provide a system in which the participants may be able to add information (provide additional information to the system), and the other participants may gain some additional value in the additional information.

Other known systems attempt to allow for bidirectional video and audio conferencing, and to allow a user to manipulate another aspect of remote communication, such as allowing an individual to demonstrate a procedure. An example of such a known system includes the PETCUBE (TRADEMARK) system (manufactured and/or supplied by PETCUBE INC., headquartered in the U.S.A.). The PETCUBE system is configured to provide bi-directional audio transmission and/or bi-directional video transmission (capabilities) for pet owners to communicate and interact with their pets that are located remotely. The PETCUBE system may be provided with a laser pointer that is controlled remotely (intended to allow owners to play with their pets). The interaction is limited to remotely controlled laser dots. It may be desirable to provide a system configured to point (position or provide) a laser dot, or a fast-moving circular mark to make it relatively easier for nurses and doctors to follow the marking indication (laser light). It may be desirable to provide a system configured to make (at least in part) a contour for outlining a surgical instrument.

Other known systems that allow for bidirectional audio and video conferencing (and for a user to manipulate another aspect of remote communications) may be found in commercially-available robotics systems, including the DOUBLE ROBOTICS (TRADEMARK) system (manufactured and/or supplied by DOUBLE ROBOTICS INC. and headquartered in U.S.A.). The DOUBLE ROBOTICS system is configured to enable bi-directional exchange (exchanging communication) of audio and video (bi-directional audio and/or bi-directional video), and/or is configured to enable the remote participant to control the physical location of the robot system.

Other known telepresence robotic systems include: (A) the PADBOT (TRADEMARK) system (manufactured and/or supplied by INBOT TECHNOLOGY LTD. and headquartered in Guangzhou, China), (B) the UBBO (TRADEMARK) system (manufactured and/or supplied by AXYN ROBOTIQUE and headquartered in Meyreuil, France), (C) the AMY (TRADEMARK) system (manufactured and/or supplied by AMY ROBOTICS and headquartered in Zhejiang, China), (D) the SUPER DROID (TRADEMARK) system (manufactured and/or supplied by SUPERDROID ROBOTS INC. and headquartered in North Carolina, U.S.A.), (E) the VGO (TRADEMARK) system (manufactured and/or supplied by VGO/VECNA TECHNOLOGIES INC. and headquartered in Massachusetts, U.S.A.), (F) the TILR (TRADEMARK) system (manufactured and/or supplied by ROBO DYNAMICS and headquartered in U.S.A.), (G) the TEXAI (TRADEMARK) system (manufactured and/or supplied by WILLOW GARAGE INC. and headquartered in California, U.S.A.), (H) the RP-VITA (TRADEMARK) system (manufactured and/or supplied by INTOUCH TECHNOLOGIES INC. and headquartered in California, U.S.A), and (I) the QB (TRADEMARK) system (manufactured and/or supplied by ANYBOTS 2.0 INC. and headquartered in California, U.S.A). It should be noted that the examples provided are generally limited to bi-directional audio and video plus physical movement of the platform. These known systems provide robotic platforms configured to physically move, and provide bi-directional exchange (exchanging communication) of audio and video information, and include a virtual-reality interface to make the participants (users) feel present through visual and auditory means, etc.

Known telepresence systems for an operating room are provided, and these systems include an interface for remote surgery. These systems do not provide support for nurses and do not provide procedural support (for surgery). Moreover, the known telepresence systems do not appear to provide sufficient assistance for surgical support (to surgeons, etc.).

What may be needed, or may be contemplated, is a telepresence apparatus configured to allow a representative (an orthopedic surgery support representative) to provide service support (surgical support) for multiple remote locations (operating rooms, preferably at the same time or nearly the same time).

To mitigate, at least in part, at least one problem associated with the existing technology, there is provided (in accordance with a first major aspect (also called a first base model) of a first invention identified in the claims section of the parent application) a telepresence apparatus. Known systems may fail to suspend (temporarily suspend), while respecting the requirement for sterile conditions required for a surgical operating room, the transmission of an aspect of a telepresence data unit (telepresence data information) while avoiding the termination of a telepresence communication session (between computer systems). The problem that is solved by the first invention (amongst other problems) is the provision for the computation of whether to suspend transmission of an aspect of a telepresence data unit (between computer assemblies), preferably while avoiding the termination of a telepresence communication session (between computer assemblies). The telepresence apparatus includes and is not limited to (comprises) a gesture sensing device, a first computer assembly configured to interface with a first memory assembly configured to tangibly store programmed coded instructions. Preferably, the telepresence apparatus is configured to utilize a sterility mechanism configured to maintain sterility of the operating room at the first location (whether by utilizing contact sterility approaches and/or non-contact sterility approaches). In accordance with a preferred embodiment, the non-contact sterility approach is utilized in which the gesture sensing device is configured to receive and sense reflected light and/or audio from a person (such as a member of the surgical staff), and to convert the reflected light into a gesture-data unit (that is associated with the sensed gesture of the user).

The programmed coded instructions are configured to urge the first computer assembly to receive a telepresence data unit. The telepresence data unit is transmitted to the first computer assembly from any one of a first display system and an audio system.

The programmed coded instructions are also configured to urge the first computer assembly to transmit the telepresence data unit to a second computer assembly via a communication network. The first computer assembly is configured to be network connectable with the communication network. The first computer assembly is also configured to be network connectable with the second computer assembly. The second computer assembly is configured to be network connectable with the communication network. The first computer assembly and the second computer assembly are also configured to be network connectable (with each other) via the communication network.

The programmed coded instructions are also configured to urge the first computer assembly to receive a user gesture signal from a gesture-sensing device. The gesture-sensing device is configured to be connectable to the first computer assembly, and in which the gesture-sensing device is also configured to detect a user gesture to be provided by a user positioned proximate to the first computer assembly, and in which the gesture-sensing device is also configured to generate the user gesture signal associated with the user gesture that was detected.

The programmed coded instructions are also configured to urge the first computer assembly to compute whether the user gesture signal, which was received by the first computer assembly, matches a predetermined user gesture stored in a first memory assembly of the first computer assembly.

The programmed coded instructions are also configured to urge the first computer assembly to compute whether to suspend transmission of an aspect of the telepresence data unit to the second computer assembly via the communication network depending on the match made between the user gesture signal and the predetermined user gesture. Preferably, the suspension (temporary suspension) of a transmission of an aspect of a telepresence data unit (telepresence data information) is conducted while avoiding the termination of the telepresence communication session (between computer assemblies).

To mitigate, at least in part, at least one problem associated with the existing technology, there is provided (in accordance with a second major aspect (also called a second base model) of a first invention identified in the claims section of the parent application) a method. Known systems fail to suspend (temporarily suspend) the transmission of an aspect of a telepresence data unit (telepresence data information) while avoiding the termination of a telepresence communication session (between computer systems). The problem that is solved by the first invention (amongst other problems) is the provision for the computation of whether to suspend transmission of an aspect of a telepresence data unit (between computer assemblies), preferably while avoiding the termination of a telepresence communication session (between computer assemblies). The method is for operating a telepresence apparatus. The telepresence apparatus includes a first computer assembly and a gesture-sensing device. The method includes and is not limited to (comprises) receiving, by the first computer assembly, a telepresence data unit. The telepresence data unit is provided (to be provided) by a remote controllable camera and a first audio system. The telepresence data unit includes electronic data (digital or analog in format).

The method also includes transmitting, from the first computer assembly, the telepresence data unit to a second computer assembly via a communication network. The first computer assembly is configured to be network connectable with the communication network. The first computer assembly is also configured to be network connectable with the second computer assembly. The second computer assembly is configured to be network connectable with the communication network. The first computer assembly and the second computer assembly are also configured to be network connectable (with each other) via the communication network.

The method also includes receiving, by the first computer assembly, a user gesture signal from the gesture-sensing device. The gesture-sensing device is configured to be connected to the first computer assembly. The gesture-sensing device is configured to detect a user gesture to be provided by a user positioned proximate to the first computer assembly. The gesture-sensing device is also configured to generate the user gesture signal associated with the user gesture that was detected.

The method also includes computing, by the first computer assembly, whether the user gesture signal, which was received by the first computer assembly, matches a predetermined user gesture stored in a first memory assembly of the first computer assembly.

The method also includes computing, by the first computer assembly, whether to suspend transmission of an aspect of the telepresence data unit (from the first computer assembly) to the second computer assembly via the communication network depending on the match made between the user gesture signal and the predetermined user gesture. Preferably, the suspension (temporary suspension) of a transmission of an aspect of a telepresence data unit (telepresence data information) is conducted while avoiding the termination of the telepresence communication session (between computer assemblies).

To mitigate, at least in part, at least one problem associated with the existing technology, there is provided (in accordance with third major aspect (also called a third base model) of a first invention identified in the claims section of the parent application) a telepresence apparatus. Known systems fail to suspend (temporarily suspend) the transmission of an aspect of a telepresence data unit (telepresence data information) while avoiding the termination of a telepresence communication session (between computer systems). The problem that is solved by the first invention (amongst other problems) is the provision for the computation of whether to suspend transmission of an aspect of a telepresence data unit (between computer assemblies), preferably while avoiding the termination of a telepresence communication session (between computer assemblies). The telepresence apparatus includes and is not limited to (comprises) a first memory assembly configured to interface with a first computer assembly. The first memory assembly is also configured to tangibly store programmed coded instructions.

The programmed coded instructions are configured to urge the first computer assembly to receive a telepresence data unit. The telepresence data unit is provided by a remote controllable camera and a first audio system (to the first computer assembly)

The programmed coded instructions are also configured to urge the first computer assembly to transmit the telepresence data unit to a second computer assembly via a communication network. The first computer assembly is configured to be network connectable with the communication network. The first computer assembly is also configured to be network connectable with the second computer assembly. The second computer assembly is configured to be network connectable with the communication network. The first computer assembly and the second computer assembly are also configured to be network connectable (with each other) via the communication network.

The programmed coded instructions are also configured to urge the first computer assembly to receive a user gesture signal from a gesture-sensing device. The gesture-sensing device is configured to be connectable to the first computer assembly. The gesture-sensing device is also configured to detect a user gesture to be provided by a user positioned proximate to the first computer assembly. The gesture-sensing device is also configured to generate the user gesture signal associated with the user gesture that was detected.

The programmed coded instructions are also configured to urge the first computer assembly to compute whether the user gesture signal, which was received by the first computer assembly, matches a predetermined user gesture stored in a first memory assembly of the first computer assembly.

The programmed coded instructions are also configured to urge the first computer assembly to compute whether to suspend transmission of an aspect of the telepresence data unit to the second computer assembly via the communication network depending on the match made between the user gesture signal and the predetermined user gesture. Preferably, the suspension (temporary suspension) of a transmission of an aspect of a telepresence data unit (telepresence data information) is conducted while avoiding the termination of the telepresence communication session (between computer assemblies).

To mitigate, at least in part, at least one problem associated with the existing technology, there is provided (in accordance with a fourth major aspect, also called a fourth base model, of a second invention to be identified in the claims section of a divisional application) a telepresence apparatus. Known systems fail to provide independent control (at least in part) of a remote controllable camera and the remote controllable laser pointer device for spatial orientation of the remote controllable camera and the remote controllable laser pointer device along different spatial orientations relative to each other. The problem that is solved by the second invention (amongst other problems) is the provision for independent control (at least in part) of a remote controllable camera and the remote controllable laser pointer device for spatial orientation of the remote controllable camera and the remote controllable laser pointer device along different spatial orientations relative to each other. The telepresence apparatus includes and is not limited to (comprises) a second computer assembly configured to be network connectable with a first computer assembly via a communication network.

The second computer assembly is configured to be connectable to a camera controller system. The camera controller system is configured to control a remote controllable camera. The remote controllable camera is configured to be connectable to the first computer assembly. The remote controllable camera is configured to be controllable by the camera controller system once the first computer assembly and the second computer assembly are network connected via the communication network.

The second computer assembly is configured to be connectable to a laser pointer controller system. The laser pointer controller system is configured to control a remote controllable laser pointer device. The remote controllable laser pointer device is configured to be connectable to the first computer assembly. The remote controllable laser pointer device is configured to be controllable by the laser pointer controller system once the first computer assembly and the second computer assembly are network connected via the communication network.

The second computer assembly is configured to (A) transmit (to the first computer assembly via the communication network) camera-control instructions (to be) provided by the camera controller system, and (B) transmit (to the first computer assembly via the communication network) laser-control instructions (to be) provided by the laser pointer controller system. This is done in such a way that: (a) the camera-control instructions and the laser-control instructions, in use, independently control the remote controllable camera and the remote controllable laser pointer device (respectively), and (b) the camera-control instructions and the laser-control instructions, in use, spatially orient the remote controllable camera and the remote controllable laser pointer device along different spatial orientations relative to each other.

To mitigate, at least in part, at least one problem associated with the existing technology, there is provided (in accordance with a fifth major aspect, also called a fifth base model, of a second invention to be identified in the claims section of a divisional application) a telepresence apparatus. Known systems fail to provide independent control (at least in part) of a remote controllable camera and the remote controllable laser pointer device for spatial orientation of the remote controllable camera and the remote controllable laser pointer device along different spatial orientations relative to each other. The problem that is solved by the second invention (amongst other problems) is the provision for independent control (at least in part) of a remote controllable camera and the remote controllable laser pointer device for spatial orientation of the remote controllable camera and the remote controllable laser pointer device along different spatial orientations relative to each other. The telepresence apparatus includes and is not limited to (comprises) a second memory assembly. The second memory assembly is configured to interface with a second computer assembly configured to be network connectable with a first computer assembly via a communication network. The second computer assembly is configured to be connectable to a camera controller system. The camera controller system is configured to control a remote controllable camera. The remote controllable camera is configured to be connectable to the first computer assembly. The remote controllable camera is configured to be controllable by the camera controller system once the first computer assembly and the second computer assembly are network connected via the communication network. The second computer assembly is configured to be connectable to a laser pointer controller system. The laser pointer controller system is configured to control a remote controllable laser pointer device. The remote controllable laser pointer device is configured to be connectable to the first computer assembly. The remote controllable laser pointer device is configured to be controllable by the laser pointer controller system once the first computer assembly and the second computer assembly are network connected via the communication network.

The second memory assembly is also configured to tangibly store programmed coded instructions. The programmed coded instructions are configured to urge the second computer assembly to perform a first operation. The first operation includes (A) transmitting (from the second computer assembly to the first computer assembly via the communication network) camera-control instructions to be provided by the camera controller system, and (B) transmitting (from the second computer assembly to the first computer assembly via the communication network) laser-control instructions (to be) provided by the laser pointer controller system. This is done in such a way that: (a) the camera-control instructions and the laser-control instructions, in use, independently control the remote controllable camera and the remote controllable laser pointer device, respectively, and (b) the camera-control instructions and the laser-control instructions, in use, spatially orient the remote controllable camera and the remote controllable laser pointer device along different spatial orientations relative to each other.

To mitigate, at least in part, at least one problem associated with the existing technology, there is provided (in accordance with a sixth major aspect, also called a sixth base model, of a second invention to be identified in the claims section of a divisional application) a method. Known systems fail to provide independent control (at least in part) of a remote controllable camera and the remote controllable laser pointer device for spatial orientation of the remote controllable camera and the remote controllable laser pointer device along different spatial orientations relative to each other. The problem that is solved by the second invention (amongst other problems) is the provision for independent control (at least in part) of a remote controllable camera and the remote controllable laser pointer device for spatial orientation of the remote controllable camera and the remote controllable laser pointer device along different spatial orientations relative to each other. The method is for operating a telepresence apparatus. The telepresence apparatus includes a second computer assembly configured to be network connectable with a first computer assembly via a communication network. The second computer assembly is configured to be connectable to a camera controller system. The camera controller system is configured to control a remote controllable camera. The remote controllable camera is configured to be connectable to the first computer assembly. The remote controllable camera is configured to be controllable by the camera controller system once the first computer assembly and the second computer assembly are network connected via the communication network. The second computer assembly is configured to be connectable to a laser pointer controller system. The laser pointer controller system is configured to control a remote controllable laser pointer device. The remote controllable laser pointer device is configured to be connectable to the first computer assembly. The remote controllable laser pointer device is configured to be controllable by the laser pointer controller system once the first computer assembly and the second computer assembly are network connected via the communication network. The method includes and is not limited to (comprises) a first operation. The first operation includes (A) transmitting (from the second computer assembly to the first computer assembly via the communication network) camera-control instructions (to be) provided by the camera controller system, and (B) transmitting (from the second computer assembly to the first computer assembly via the communication network) laser-control instructions (to be) provided by the laser pointer controller system. This is done in such a way that: (a) the camera-control instructions and the laser-control instructions, in use, independently control the remote controllable camera and the remote controllable laser pointer device (respectively), and (b) the camera-control instructions and the laser-control instructions, in use, spatially orient the remote controllable camera and the remote controllable laser pointer device along different spatial orientations relative to each other.

To mitigate, at least in part, at least one problem associated with the existing technology, there is provided (in accordance with a seventh major aspect, also called a seventh base model, of a third invention to be identified in the claims section of a divisional application) a telepresence apparatus. Known systems fail to provide remote identification of a surgical instrument to a user positioned at a remote location. The problem that is solved by the third invention (amongst other problems) is the provision for a remote controllable laser pointer device to issue a light pattern, which is for the identification of a surgical instrument to a user positioned at a remote location. The telepresence apparatus includes and is not limited to (comprises) a second computer assembly configured to be network connectable with a first computer assembly via a communication network. The second computer assembly is configured to be connectable to a camera controller system. The camera controller system is configured to control a remote controllable camera. The remote controllable camera is configured to be connectable to the first computer assembly. The remote controllable camera is configured to be controllable by the camera controller system once the first computer assembly and the second computer assembly are network connected via the communication network.

The second computer assembly is configured to be connectable to a laser pointer controller system. The laser pointer controller system is configured to control a remote controllable laser pointer device. The remote controllable laser pointer device is configured to be connectable to the first computer assembly. The remote controllable laser pointer device is configured to be controllable by the laser pointer controller system once the first computer assembly and the second computer assembly are network connected via the communication network.

The second computer assembly is also configured to interface with a second display system. The second computer assembly is also configured to transmit (to the first computer assembly via the communication network) an image of a surgical instrument. This is done in such a way that the first computer assembly, in use, urges a first display system of the first computer assembly to display the image of the surgical instrument to a user positioned proximate to the first computer assembly. More specifically, the first computer assembly, in use, transmits a display command (along with the image) to the first display system of the first computer assembly to display the image of the surgical instrument (which was received from the second computer assembly via the communication network) to the user positioned proximate to the first computer assembly.

The second computer assembly is also configured to transmit (to the first computer assembly via the communication network) laser-control instructions (to be) provided by the laser pointer controller system. This is done in such a way that the laser-control instructions, in use, urge the remote controllable laser pointer device to issue a light pattern. The light pattern, in use, identifies (or alternately, matches an outline or contours of) the surgical instrument to the user positioned proximate to the first computer assembly (for instance, this may be useful when highlighting what instrument is required next in a surgery and when putting instruments back in their correct spots (respective spots or positions) located in a storage tray). For instance, the light pattern may also be a fast-moving circle to bring the attention of the eye of the nurse and/or surgeon to the surgical instrument being highlighted.

To mitigate, at least in part, at least one problem associated with the existing technology, there is provided (in accordance with an eighth major aspect, also called an eighth base model, of a third invention to be identified in the claims section of a divisional application) a telepresence apparatus. Known telepresence systems fail to provide remote identification of a surgical instrument to a user positioned at a first physical site or location. The problem that is solved by the third invention (amongst other problems) is the provision for a remote controllable laser pointer device to issue a light pattern, which is for the identification of a surgical instrument to a user positioned at a remote location. The telepresence apparatus includes and is not limited to (comprises) a second memory assembly. The second memory assembly is configured to interface with a second computer assembly configured to be network connectable with a first computer assembly via a communication network. The second computer assembly is configured to be connectable to a camera controller system. The camera controller system is configured to control a remote controllable camera. The remote controllable camera is configured to be connectable to the first computer assembly. The remote controllable camera is configured to be controllable by the camera controller system once the first computer assembly and the second computer assembly are network connected via the communication network. The second computer assembly is configured to be connectable to a laser pointer controller system. The laser pointer controller system is configured to control a remote controllable laser pointer device. The remote controllable laser pointer device is configured to be connectable to the first computer assembly. The remote controllable laser pointer device is configured to be controllable by the laser pointer controller system once the first computer assembly and the second computer assembly are network connected via the communication network. The second computer assembly is also configured to interface with a second display system.

The second memory assembly is also configured to tangibly store programmed coded instructions. The programmed coded instructions are configured to urge the second computer assembly to perform a first operation. The first operation includes transmitting (from the second computer assembly to the first computer assembly via the communication network) an image of a surgical instrument. This is done in such a way that the first computer assembly, in use, urges a first display system of the first computer assembly to display the image of the surgical instrument to a user positioned proximate to the first computer assembly. More specifically, the first computer assembly, in use, transmits a display command (along with the image) to the first display system of the first computer assembly to display the image of the surgical instrument (which was received from the second computer assembly via the communication network) to the user positioned proximate to the first computer assembly. The programmed coded instructions are configured to urge the second computer assembly to perform a second operation. The second operation includes transmitting (from the second computer assembly to the first computer assembly via the communication network) laser-control instructions (to be) provided by the laser pointer controller system. This is done in such a way that the laser-control instructions, in use, urge the remote controllable laser pointer device to issue a light pattern. The light pattern, in use, identifies (preferably, matches an outline or contours of) the surgical instrument to the user positioned proximate to the first computer assembly (useful when putting instruments back in their correct spots located in a storage tray). Although the remote controllable laser pointer device may assist the surgical staff in highlighting a surgical instrument (such as, the position in which the surgical instrument belongs in the surgical tray), the main function of the laser pointer includes highlighting (in use) a surgical instrument when the surgical instrument is required by the surgeon during the surgical procedure. If necessary, additional information on the correct assembly and use of the instrument may be provided on the computer screen (display screen) viewable by staff in the surgical field.

To mitigate, at least in part, at least one problem associated with the existing technology, there is provided (in accordance with a ninth major aspect, also called a ninth base model, of a third invention to be identified in the claims section of a divisional application) a method. Known systems fail to provide remote identification of a surgical instrument to a user positioned at a first physical site. The problem that is solved by the third invention (amongst other problems) is the provision for a remote controllable laser pointer device to issue a light pattern, which is for the identification of a surgical instrument to a user positioned at a remote location. The method is for operating a telepresence apparatus. The telepresence apparatus includes a second computer assembly configured to be network connectable with a first computer assembly via a communication network. The second computer assembly is configured to be connectable to a camera controller system. The camera controller system is configured to control a remote controllable camera. The remote controllable camera is configured to be connectable to the first computer assembly. The remote controllable camera is configured to be controllable by the camera controller system once the first computer assembly and the second computer assembly are network connected via the communication network. The second computer assembly is configured to be connectable to a laser pointer controller system. The laser pointer controller system is configured to control a remote controllable laser pointer device. The remote controllable laser pointer device is configured to be connectable to the first computer assembly. The remote controllable laser pointer device is configured to be controllable by the laser pointer controller system once the first computer assembly and the second computer assembly are network connected via the communication network. The second computer assembly is also configured to interface with a second display system.

The method includes and is not limited to (comprises) a first operation. The first operation includes transmitting (from the second computer assembly to the first computer assembly via the communication network) an image of a surgical instrument in such a way that the first computer assembly, in use, urges a first display system of the first computer assembly to display the image of the surgical instrument to a user positioned proximate to the first computer assembly. More specifically, the first computer assembly, in use, transmits a display command (along with the image) to the first display system of the first computer assembly to display the image of the surgical instrument (which was received from the second computer assembly via the communication network) to the user positioned proximate to the first computer assembly.

The method further includes a second operation. The second operation includes transmitting (from the second computer assembly to the first computer assembly via the communication network) laser-control instructions (to be) provided by the laser pointer controller system. This is done in such a way that the laser-control instructions, in use, urge the remote controllable laser pointer device to issue a light pattern, in which the light pattern, in use, identifies (preferably, matches an outline or contours of) the surgical instrument to the user positioned proximate to the first computer assembly (useful when putting instruments back in their correct spot located in a storage tray). Although the remote controllable laser pointer device may assist the surgical staff in highlighting a surgical instrument (such as, the position in which the surgical instrument belongs in the surgical tray), the main function of the laser pointer includes highlighting (in use) a surgical instrument when the surgical instrument is required by the surgeon during the surgical procedure. If necessary, additional information on the correct assembly and use of the instrument may be provided on the computer screen (computer display or computer display screen) viewable by staff in the surgical field.

To mitigate, at least in part, at least one problem associated with the existing technology, there is provided (in accordance with a tenth major aspect (also called a base model) of a fourth invention to be identified in the claims section of a divisional application) a telepresence apparatus. Known systems fail to control remote controllable cameras (a primary camera and an auxiliary camera) and to control a remote controllable laser pointer devices (a primary pointer device and an auxiliary pointer device). The problem that is solved by the fourth invention (amongst other problems) is the provision for the control of remote controllable cameras (a primary camera and an auxiliary camera), and the control of a remote controllable laser pointer devices (a primary pointer device and an auxiliary pointer device). The telepresence apparatus includes: (A) a first computer assembly configured to be network connectable with a second computer assembly via a communication network. The first computer assembly is also configured to interface with a first memory assembly configured to tangibly store programmed coded instructions, in which the programmed coded instructions are configured to urge the first computer assembly to interact with: (A) a remote controllable camera and a first auxiliary remote controllable camera each configured to be connectable to the first computer assembly, and in which the remote controllable camera and the first auxiliary remote controllable camera each configured to be controllable by a camera controller system once the first computer assembly and the second computer assembly are network connected via the communication network, and in which the second computer assembly is configured to be connectable to a camera controller system, and in which the second computer assembly is configured to transmit, to the first computer assembly, camera-control instructions provided by the camera controller system in such a way that the camera-control instructions, in use, control the remote controllable camera and the first auxiliary remote controllable camera; and (B) a remote controllable laser pointer device and a first auxiliary remote controllable laser pointer device each configured to be connectable to the first computer assembly, and in which the remote controllable laser pointer device and the first auxiliary remote controllable laser pointer device are each configured to be controllable by a laser pointer controller system once the first computer assembly and the second computer assembly are network connected via the communication network, and in which the second computer assembly is configured to be connectable to the laser pointer controller system, and in which the second computer assembly is configured to transmit, to the first computer assembly laser-control instructions provided by the laser pointer controller system in such a way that the laser-control instructions, in use, controls the remote controllable laser pointer device and the first auxiliary remote controllable laser pointer device. The above arrangement may be beneficial to a surgical environment (saves time by having a technician to work one, two, three steps ahead of the operating room users; avoids delays caused by pan, tilt and zoom of a single camera and single laser, which do not move quickly; helps operating room staff identify instruments and devices more quickly; some orthopedic operating rooms set-ups may be too large to be effectively covered by a single camera, especially when using a sterile implant room that is located adjacent or nearby to the operating room). Space may be limited in operating rooms. Deployment of the auxiliary devices allows access to other rooms with implants and other operating tables outside the field-of-view of a main camera while minimizing the physical footprint of the apparatus.

In accordance with an embodiment, the following describes a telepresence apparatus to be deployed in a command-center room. The telepresence apparatus is for a first computer assembly (an operating-room computer) that is positioned in (located in) an operating room. The telepresence apparatus includes (comprises) a second computer assembly (a command-center computer) positioned in (located in) a command-center room. The second computer assembly is configured to be network connected with the first computer assembly. The first computer assembly is configured to be network connectable with the second computer assembly via a communication network. The first computer assembly is also configured to interface with a first memory assembly configured to tangibly store programmed coded instructions (to be utilized by a processor of a computer system). The programmed coded instructions are configured to urge (instruct) the first computer assembly to receive (either directly or indirectly) a user gesture signal from a gesture-sensing device (which is positioned in the operating room) (when, or once, the coded instructions are utilized or executed by a processor or a computer system). The gesture-sensing device is configured to be connectable to the first computer assembly. The gesture-sensing device is also configured to detect a user gesture to be provided by a user positioned proximate to the first computer assembly. The gesture-sensing device is also configured to generate the user gesture signal associated with the user gesture that was detected. The programmed coded instructions (when, or once, the coded instructions are utilized by a processor or a computer system) are also configured to urge the first computer assembly to compute whether the user gesture signal, which was received by the first computer assembly, matches a predetermined user gesture stored in the first memory assembly of the first computer assembly. The programmed coded instructions are also configured to urge the first computer assembly to compute whether to suspend transmission of an aspect of a telepresence data unit from the first computer assembly to the second computer assembly via the communication network depending on a match made between the user gesture signal and the predetermined user gesture.

In accordance with an embodiment, the following describes a telepresence apparatus to be deployed in an operating room. The telepresence apparatus includes (comprises) a first computer assembly (an operating-room computer that is positioned in the operating room). The first computer system is configured to be network connectable with a second computer assembly (a command-center computer that is positioned in a command-center room) via a communication network. The first computer assembly is also configured to interface with a first memory assembly configured to tangibly store programmed coded instructions (when, or once, utilized by a processor of a computer system). The programmed coded instructions are configured to urge the first computer assembly to receive a user gesture signal from a gesture-sensing device (positioned in the operating room) (when, or once, the coded instructions are utilized by a processor or a computer system). The gesture-sensing device is configured to be connectable to the first computer assembly. The gesture-sensing device is also configured to detect a user gesture to be provided by a user positioned proximate to the first computer assembly. The gesture-sensing device is also configured to generate the user gesture signal associated with the user gesture that was detected. The programmed coded instructions are also configured to urge the first computer assembly to compute whether the user gesture signal, which was received by the first computer assembly, matches a predetermined user gesture stored in the first memory assembly of the first computer assembly (when, or once, the coded instructions are utilized by a processor or a computer system). The programmed coded instructions are also configured to urge the first computer assembly to compute whether to suspend transmission of an aspect of a telepresence data unit from the first computer assembly to the second computer assembly via the communication network depending on a match made between the user gesture signal and the predetermined user gesture (when, or once, the coded instructions are utilized by a processor or a computer system).

In accordance with an embodiment, the following describes a telepresence apparatus to be deployed in a data-storage room. The telepresence apparatus includes (comprises) a data-storage computer positioned in (located in) the data-storage room. The data-storage computer is configured to communicate with a first computer assembly (an operating-room computer that is positioned in an operating room). The first computer system is configured to be network connectable with a second computer assembly (a command-center computer that is located in the command-center (also called a control-center room, a control room, a central control room, etc.) via a communication network. It will be appreciated that the command-center computer may be called a control-center computer, etc. The data-storage computer is configured to communicate with the first computer assembly and the second computer assembly. The data-storage computer is configured to provide training materials to the first computer system (upon, or in response to, receiving a command request for such training materials). The data-storage computer is configured to provide training materials to the second computer system (upon, or in response to, receiving a command request for such training materials). The first computer assembly is also configured to interface with a first memory assembly configured to tangibly store programmed coded instructions (to be utilized by a processor or a computer system). The programmed coded instructions are configured to urge the first computer assembly to receive a user gesture signal from a gesture-sensing device positioned in the operating room. The gesture-sensing device is configured to be connectable to the first computer assembly. The gesture-sensing device is also configured to detect a user gesture to be provided by a user positioned proximate to the first computer assembly. The gesture-sensing device is also configured to generate the user gesture signal associated with the user gesture that was detected. The programmed coded instructions are also configured to urge the first computer assembly to compute whether the user gesture signal, which was received by the first computer assembly, matches a predetermined user gesture stored in the first memory assembly of the first computer assembly (when, or once, the coded instructions are utilized by a processor or a computer system). The programmed coded instructions are also configured to urge the first computer assembly to compute whether to suspend transmission of an aspect of a telepresence data unit from the first computer assembly to the second computer assembly via the communication network depending on a match made between the user gesture signal and the predetermined user gesture. It will be appreciated that the gesture sensing feature may have other uses in addition to suspending transmission of signals.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify key features or essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
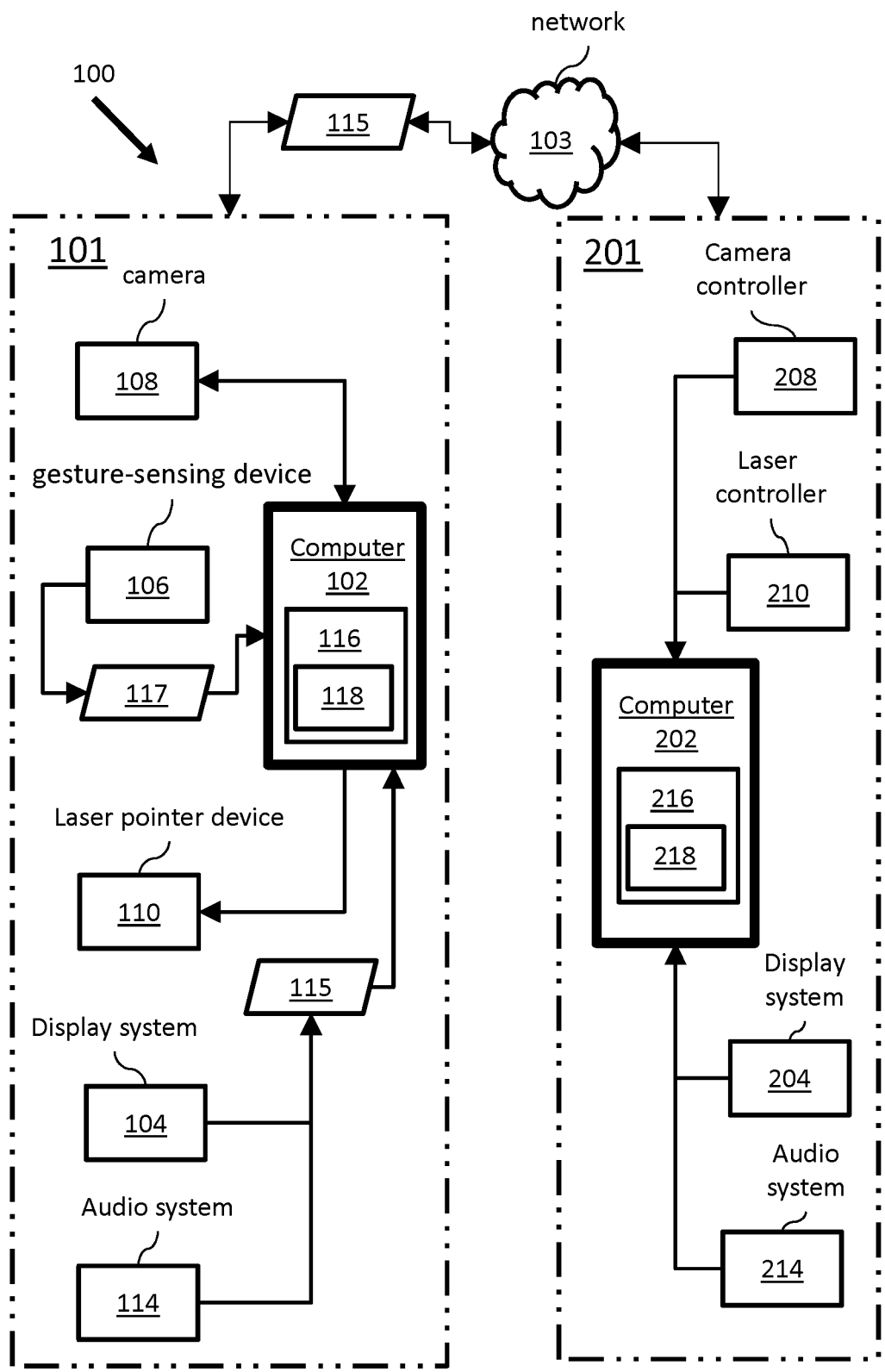
FIG. 1 depicts a schematic view of an embodiment of a telepresence apparatus including a synergistic combination of a first computer assembly and a gesture-sensing device.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, but well-understood, elements that are useful or necessary in commercially feasible embodiments are often not depicted to provide a less obstructed view of the embodiments of the present disclosure.

LISTING OF REFERENCE NUMERALS USED IN THE DRAWINGS 100 telepresence apparatus
101 first physical site
102 first computer assembly
103 communication network
104 first display system
106 gesture-sensing device
108A first auxiliary remote controllable camera
108B second auxiliary remote controllable camera
108 remote controllable camera
110A first auxiliary remote controllable laser pointer device
110B second auxiliary remote controllable laser pointer device
110 remote controllable laser pointer device
111 light pattern
114 first audio system
115 telepresence data unit
116 first memory assembly
117 user gesture signal
118 programmed coded instructions (tangibly stored programmed coded instructions)
196 first table
197 second table
201 second physical site
202 second computer assembly
204 second display system
208 camera controller system
210 laser pointer controller system
212 user interface
214 second audio system
216 second memory assembly
218 programmed coded instructions
300 cart assembly
301 surgical instrument (medical equipment)
302 casters
303 storage tray
304 working platform
802 first operation 804 second operation
806 third operation
808 fourth operation
810 fifth operation
812 first operation
814 first operation
816 second operation

DETAILED DESCRIPTION OF THE
EXEMPLARY EMBODIMENTS

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the invention (or inventions) may be defined by the claims (in which the claims may be amended during patent examination after filing of this application). For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the invention is limited to the subject matter provided by the claims, and that the invention is not limited to the particular aspects depicted and described.

FIG. 1 depicts a schematic view of an embodiment of a telepresence apparatus 100 including a synergistic combination of a first computer assembly 102 and a gesture-sensing device 106. For instance, the gesture-sensing device 106 may include (and is not limited to) (A) a multimodal interactive device, (B) a gesture-sensing sensor connected to a KINECT (TRADEMARK) compatible device (the KINECT device is manufactured by MICROSOFT (TRADEMARK), based in USA), (C) a speaker device for providing an audio command via the SIRI (TRADEMARK) system (the SIRI system is manufactured by APPLE COMPUTERS INC., based in U.S.A.), and/or a foot switch, etc., and any equivalent thereof.

Referring to the embodiment as depicted in FIG. 1 (and in accordance with a first general aspect), a telepresence apparatus 100 includes (and is not limited to) a first computer assembly 102. The first computer assembly 102 is configured to be positioned in a first physical site 101. The second computer assembly 202 is positioned in a second physical site 201, which is located remotely from the first physical site 101. For instance, the first computer assembly 102 includes (and is not limited to) a first display system 104, a first audio system 114 (which may include a microphone and speaker), a gesture-sensing device 106, a remote controllable camera 108, and a remote controllable laser pointer device 110. For instance, the second computer assembly 202 includes (and is not limited to) a second display system 204, a second audio system 214 (which may include a microphone and speaker), a camera controller system 208, and a laser pointer controller system 210. The first computer assembly 102 is configured to interface with a first memory assembly 116 configured to tangibly store programmed coded instructions 118 (also called an executable program). The programmed coded instructions 118 include coded instructions configured to be readable by, and executable by, the first computer assembly 102.

Embodiments of the programmed coded instructions 118 may include: (A) machine language and any equivalent thereof, (B) source code formed as a high-level language understood by humans and any equivalent thereof, and (C) code formed as an assembly language more complex for humans but more closely associated with machine-code instructions and any equivalent thereof. The high-level language of the source code is compiled into either an executable machine code file or a non-executable machine-code object file. Other equivalents to the programmed coded instructions 118 may include: (A) an application-specific integrated circuit and any equivalent thereof, and (B) a field-programmable gate array (FPGA) and any equivalent thereof.

The programmed coded instructions 118 are configured to urge the first computer assembly 102 to receive a telepresence data unit 115. The telepresence data unit 115 is provided by a remote controllable camera 108 and a first audio system 114 (to the first computer assembly 102). The telepresence data unit 115 may include audio and/or video information. The telepresence data unit 115 may include electronic data (digital or analog in format). It will be appreciated that the user gesture signal 117 is provided by the gesture-sensing device 106. The first computer assembly 102 is configured to (A) input (receive) the user gesture signal 117 from the gesture-sensing device 106, and (B) determine whether to suspend communication of the telepresence data unit 115 (the telepresence data unit 115 is provided by a remote controllable camera 108 and a first audio system 114).

In accordance with a preferred embodiment, the gesture-sensing device 106 (which is located in first physical site 101) may be configured to call for assistance from a support representative (which is located in the second physical site 201) without compromising the sterile field (which is located in first physical site 101).

The programmed coded instructions 118 are also configured to urge the first computer assembly 102 to transmit (exchange of or exchanging communication of) the telepresence data unit 115 to (with) the second computer assembly 202 via a communication network 103. The first computer assembly 102 is configured to: (A) be network connectable with the communication network 103, and (B) be network connectable with the second computer assembly 202. The second computer assembly 202 is configured to be network connectable with the communication network 103. The first computer assembly 102 and the second computer assembly 202 are also configured to be network connectable (with each other) via the communication network 103.

The programmed coded instructions 118 are also configured to urge the first computer assembly 102 to receive a user gesture signal 117 from the gesture-sensing device 106. The user gesture signal 117 may include, for instance, the wave of an arm of the user located in the first physical site 101. The gesture-sensing device 106 is configured to be connectable to the first computer assembly 102. The gesture-sensing device 106 is also configured to detect a user gesture to be provided by a user that is positioned proximate to the first computer assembly 102. The gesture-sensing device 106 is also configured to generate the user gesture signal 117 associated with the user gesture that was detected (in response to detection of the user gesture provided by the user positioned proximate to the first computer assembly 102). The gesture-sensing device 106 may include (and is not limited to) (A) a multimodal interactive device, (B) a gesture-sensing sensor connected to a KINECT (TRADEMARK) compatible device (the KINECT device is manufactured by MICROSOFT (TRADEMARK), based in USA), (C) a speaker device for providing an audio command via the SIRI (TRADEMARK) system (the SIRI system is manufactured by APPLE COMPUTERS INC., based in U.S.A.), and/or a foot switch, any type of signaling device such as foot-activated switch, a knee-activated switch, a hand-activated switch, devices configured to receive an audio signal (a word, words, phrases, sounds such as a clapping sound made by two hands, an interface of the first display system 104, etc., and any equivalent thereof (for the purpose of establishing a privacy screen). The scope of gesture sensing includes (and is not limited to) any type of multimodal interaction. Multiple communication methods and/or multimodal interactive devices may be utilized from the sterile field (located in the surgical room), and may include, and are not limited to, gesture communication via a KINECT (TRADEMARK) sensor, audio communication via a SIRI (TRADEMARK) device, and/or a foot-switch device, etc., and any equivalent thereof (devices for communicating with a remote user without compromising sterility of the surgical field located in the surgical room).

The programmed coded instructions 118 are also configured to urge the first computer assembly 102 to compute whether the user gesture signal 117, which was received by the first computer assembly 102, matches a predetermined user gesture stored in the first memory assembly 116 of the first computer assembly 102. For instance, the user gesture signal 117 may include, for instance, a signal that represents the wave of an arm of the user located in the first physical site 101, and the predetermined user gesture (information stored in the first memory assembly 116) includes code configured to assist in determining whether the user gesture signal 117, in fact, matches or does not match a wave of an arm of a user.

The programmed coded instructions 118 are also configured to urge the first computer assembly 102 to compute whether to suspend transmission of an aspect of (portion of) the telepresence data unit 115 to the second computer assembly 202 via the communication network 103. The suspension of the transmission of the aspect of the telepresence data unit 115 depends on the match made between the user gesture signal 117 and the predetermined user gesture.

For instance, the programmed coded instructions 118 are configured to urge the first computer assembly 102 to manage the privacy (an aspect) of the telepresence data unit 115. This arrangement may, for instance, ensure patient confidentiality during a surgical procedure that may be potentially exchanged (via the transmission of the telepresence data unit 115 during the telepresence communications session between the first computer assembly 102 and the second computer assembly 202 via the communication network 103). Management of the telepresence data unit 115 may include (and is not limited to): (A) forcing a blank screen (on the second display system 204 of the second computer assembly 202), and (B) forcing the stoppage of the transmission of the audio signal and/or the video signal content of the telepresence data unit 115 during the telepresence session (such as, pulling down a privacy curtain, etc.). It will be appreciated that the telepresence communications are suspended (stopped or muted) for audio transmission and/or video transmission between the first computer assembly 102 and the second computer assembly 202 without necessarily terminating the telepresence communication session. There may be an option, if desired (required), to entirely terminate the telepresence communications (such as, ending the telepresence call altogether). The first computer assembly 102 and the gesture-sensing device 106 may be configured to allow the user (the surgeon or the nurse) to restart or resume the telepresence communication session (also called the telepresence call) once the privacy issue is resolved in the surgical theater (operating room). Alternatively, the microphone (that is operatively connected to the first computer assembly 102) and the first computer assembly 102 are configured to receive from the user (the surgeon or the nurse) an audio signal ("start privacy" or "stop privacy" to start, stop and/or restart (resume) the telepresence communication session (for instance, once the privacy issue is identified and/or resolved in the surgical theater or the operating room). More specifically, the microphone is operatively connected to the first computer assembly 102. The microphone and the first computer assembly 102 are configured to receive from an audio signal associated with initiating a privacy screen to block a video feed from reaching the second display system 204 of the second computer assembly 202 (this is done in such a way that the first computer assembly 102 initiates the privacy screen to temporarily block (suspend) the video feed or the audio feed to be sent to the second computer assembly 202).

The gesture-sensing device 106 may include the MICROSOFT (TRADEMARK) KINECT (TRADEMARK) device and any equivalent thereof. The gesture-sensing device 106 is configured to receive audio information, video information, and/or mechanical information (mechanical movements). The gesture-sensing device 106 is configured to allow for the operating-room staff to interact with the telepresence apparatus 100 using any suitable type of gesturing technique, such as in-the-air gestures. This allows the operating-room staff to operate, at least in part, the telepresence apparatus 100 without having to physically be in contact with the telepresence apparatus 100 (thereby maintaining sterility of the operating room). The gesture-sensing device 106 helps, at least in part, to maintain a sterile operating room environment. In some examples, the gesture-sensing device 106 (in-air gestural interface) may allow the operating-room staff to (A) call for remote support, (B) pull down a privacy curtain that stops audio/video transmission to ensure patient confidentiality, and (C) end the call. For instance, the gesture-sensing device 106 may also include an interface for the first display system 104, in which the interface is configured to assist a person located in the operating room to pause the telepresence communication by touching a screen icon or computer key(s) in an emergency situation, or assuming such person was not part of the sterile team. This arrangement may allow the circulating nurse (non-sterile nurse) to control the privacy of the telepresence session (and/or the call buttons).

Referring to the embodiment as depicted in FIG. 1, and in accordance with another embodiment, the first computer assembly 102 (such as, an operating-room computer) is configured to be network connectable with the communication network 103. The first computer assembly 102 may include a desktop computer, a laptop computer, etc., and any equivalent thereof. For instance, the first computer assembly 102 may be (or may include, and is not limited to) an operating-room computer configured to be positioned in a surgical operating room (also called a surgical theater, a medical consultation room, a medical treatment room, etc., and any equivalent thereof). For instance, this is done in such a way that the operating-room computer is available for interactive use by the users or the participants (such as doctors, nurses, etc.) located in the operating room and involved with a surgical procedure or operation performed in the surgical operating room. The users of the first computer assembly 102 may require assistance (advice, training, information) during the surgical procedure, which may be provided to the users via the first computer assembly 102.

It will be appreciated that the communication network 103 may include any type of communications network, such as (and not limited to) the Internet, or any type of a public communications network with adequate controls put in place to ensure secured communications to and from the first computer assembly 102, a private communications network, etc., and any equivalent thereof.

Furthermore, the first computer assembly 102 is configured to be network connectable with a second computer assembly 202. For instance, the second computer assembly 202 may be (or may include) a remotely-located computer (that is, a computer that is located remotely from the first computer assembly 102). The second computer assembly 202 is configured to be positioned physically remotely relative to the first computer assembly 102. For instance, the second computer assembly 202 is configured to be positioned in a conference room, an office, etc., in which the second computer assembly 202 may be positioned or located many miles away from first computer assembly 102. The second computer assembly 202 may include a desktop computer, a laptop computer, a tablet device, a smartphone, and any equivalent thereof. The second computer assembly 202, in use, improves the mobility and/or the ability of operators to provide surgical support remotely (from the second computer assembly 202. The second computer assembly 202 is also configured to be network connectable with the communication network 103. The first computer assembly 102 and the second computer assembly 202 are configured to be network connectable (with each other) via the communication network 103. This is done in such a way that the first computer assembly 102 and the second computer assembly 202, in use, transceive (that is, exchange, transmit and/or receive, exchanging communication) the telepresence data unit 115 (also called a telepresence communications or a telepresence call) between the first computer assembly 102 and the second computer assembly 202. As such, the first computer assembly 102 and the second computer assembly 202 are configured to be network connected for establishing the exchange (exchanging communication) of the telepresence data unit 115 between the first computer assembly 102 and the second computer assembly 202.

In accordance with an embodiment, the gesture-sensing device 106 is provided. The gesture-sensing device 106 may include, for instance, a motion controller, such as the KINECT (TRADEMARK) motion controller Model Number 1517 manufactured and/or supplied by Microsoft Corporation (headquartered in the U.S.A.), and any equivalent thereof. The gesture-sensing device 106 is configured to detect or facilitate in-the-air gestures from a user. The gesture-sensing device 106 (also called a motion sensor and/or controller) is configured to sense (or control) the motion of an object (a virtual object or a non-virtual object). The gesture-sensing device 106 may be implemented using a digital computer. The gesture-sensing device 106 may also be implemented with only analog components as well). The gesture-sensing device 106 is configured to provide a natural user interface device that may be utilized by the first computer assembly 102 (such as the user interface, etc.), and may provide a motion controller system that uses, for instance, an infrared array configured to (A) detect the presence and motions of the user or users, (B) provide speech recognition, and (C) provide a microphone and a video camera that may be configured to record and stream video footage, etc. The gesture-sensing device 106 is configured to detect motion tracking (of the user) and recognize the voice (or predetermined sound made by or caused by) of the user. The gesture-sensing device 106 may be configured to track a number of users at once.

The gesture-sensing device is configured to: (A) be connected to the first computer assembly 102, (B) detect a user gesture associated with a user positioned proximate to the first computer assembly 102, (C) generate a user gesture signal 117 associated with the user gesture that was detected in association with the user positioned proximate to the first computer assembly 102, and (D) transmit, via the communication network 103, the user gesture signal 117 to the first computer assembly 102.

The first computer assembly 102 is further configured to: (A) receive the user gesture signal 117 from the gesture-sensing device 106, and (B) control a privacy aspect (portion) of the telepresence data unit 115 to be transceived (exchanged), via the communication network 103, between the first computer assembly 102 and the second computer assembly 202, depending on the content of the user gesture signal 117 that was received from the gesture-sensing device 106.

A technical effect of the telepresence apparatus 100 (as depicted in FIG. 1) is that sterile room conditions may be maintained (that is, the surgeon and/or nurses do not have to touch any potentially unsterile surfaces of the telepresence apparatus, such as control knobs, buttons, etc., because the telepresence apparatus 100 is configured to operate through receiving and responding to the hand gestures provided by the user or the surgeon, etc.). In addition, the telepresence apparatus 100 may improve or maintain patient confidentially (when needed), which is of paramount importance in operating rooms. For instance, the user (such as, the nurse or the surgeon) may wave their hand using a predetermined gesture, in which case the gesture-sensing device 106 may interpret the predetermined gesture as a request to manage or control the telepresence data unit 115, such as to temporarily suspend the exchange (exchanged communication) of the telepresence data unit 115, etc., and any equivalent thereof.

The telepresence apparatus is configured, at least in part, to allow the user in an environment (such as, but not limited to, an operating theater or room) to control, direct, manipulate, and/or manage the telepresence communications between the first computer assembly 102 and the second computer assembly 202. For instance, in this embodiment, the first computer assembly 102 and the gesture-sensing device 106 are configured to manage the privacy of the telepresence data unit 115 (for instance, to ensure patient confidentiality during a surgical procedure, etc., and any equivalent thereof) that may be exchanged during the telepresence communications. Management of the telepresence data unit 115 may include (and is not limited to): (A) forcing a blank screen (on the display of the second computer assembly 202), and (B) forcing stoppage of the audio signal and/or the video signal content of the telepresence data unit 115 during the telepresence session (such as, pulling down a privacy curtain), in which the telepresence communications are suspended (stopped or muted) for audio transmission and/or video transmission between the first computer assembly 102 and the second computer assembly 202 without necessarily terminating the telepresence communication session. There may be an option, if desired (required), to entirely terminate the telepresence communications (such as ending of the telepresence call). The first computer assembly 102 and the gesture-sensing device 106 may be configured to allow the user (the surgeon or the nurse) to restart or resume the telepresence communication session (also called the telepresence call) once the privacy issue is resolved in the surgical theater. It will be appreciated that the management of the telepresence data unit 115 may also include the provision of a signal (such as, a visual signal and/or an audio signal, etc.) to the technician (located proximate to the second computer assembly 202), in which the signal requests the remote technician's attention and/or for initiating a two-way audio-visual interaction, etc.

An embodiment of the manner in which the telepresence apparatus of FIG. 1 may be utilized is provided. The first computer assembly 102 is configured to be network connectable with the communication network 103, and the second computer assembly 202 is configured to be network connectable to the communication network 103. The first computer assembly 102 and the second computer assembly 202 are configured to be network connected (to each other) via the communication network 103.

It will be appreciated that the communication network 103 may include (and is not limited to) any one or a combination of devices communicating over communication channel, such as a wireless channel, a wired channel, the ETHERNET (TRADEMARK) network (manufactured and/or supplied by Xerox Corporation headquartered in the U.S.A.), a USB (Universal Serial Bus) network adaptor, the Internet, a VPN (Virtual Private Network), and/or a private network, etc., and any equivalent thereof. In this embodiment, the first computer assembly 102 and the second computer assembly 202 may be configured to be connected over the Internet using a Virtual Private Network (VPN), etc.

A telepresence communications may be established between the first computer assembly 102 and the second computer assembly 202, once the first computer assembly 102 is connected to the second computer assembly 202 over the communication network 103. Telepresence communication may include, and is not limited to, a one-way communication network (e.g., simplex or half-duplex), a two-way communication network (e.g., duplex), or a multi-way communication network (e.g. group). Telepresence communication may include, and is not limited to, phone calls (audio transmission), two-way radio communication, SMS (Short Message Service) messaging and/or MMS (Multimedia Messaging Service) messaging, network-enabled phone calling, network-enabled video calling, GOOGLE (TRADEMARK) HANGOUTS (TRADEMARK) communications system (manufactured by GOOGLE INC.), APPLE (TRADEMARK) FACETIME (TRADEMARK) communications system (manufactured by APPLE INC.), and/or any type of software application configured to exchange communications from one network-connected computer to another.

Once the user of the first computer assembly 102 (for instance, a surgeon) determines that the telepresence communication should be suspended, the user performs a pre-determined user gesture proximate to (in front of) the gesture-sensing device 106 in such a way that that the gesture-sensing device 106 can capture (receive and process) the predetermined user gesture. In some embodiments, the user gesture does not require that the user physically touch, or otherwise come in contact with, the first computer assembly 102 or the gesture-sensing device 106 (i.e., the user gesture is performed in-the-air).

It will be appreciated that the user gesture may include any combination of hand, head, and/or body movements, etc. In some embodiments, the user may also use a motion-enhancement device (known and not depicted) configured to assist in the capture (reception) of user gestures by the gesture-sensing device 106. This may include, and is not limited to, a wand device having one or more sensors (including, and not limited to, gyros, accelerometers, pressure sensors, etc.), a uniquely colored item, a light source, or any other device or item that may be utilized to enhance the user gestures to be collected by the gesture-sensing device 106.

Once the gesture-sensing device 106 captures the user gesture, the gesture-sensing device 106 generates a user gesture signal 117 associated with the user gesture that was detected in association with movement of the user. The gesture-sensing device 106 then transmits the user gesture signal 117 to the first computer assembly 102 (preferably using a wireless connection).

Referring to the embodiment as depicted in FIG. 1, the gesture-sensing device 106 may be connected to the first computer assembly 102 using a USB connection, etc., and any equivalent thereof. The gesture-sensing device 106 may be connected to the first computer assembly 102 using known wireless networking protocols (e.g., 802.11b, infrared, etc.), known wired networking protocols (e.g., the ETHERNET (TRADEMARK) connection), or may even be configured to communicate over the Internet with the first computer assembly 102. For instance, an IP-based remote camera may be connected via the Internet (network) to the first computer assembly 102, and the first computer assembly 102 is implemented in a cloud computing environment.

The first computer assembly 102 is configured to receive the user gesture signal 117 from the gesture-sensing device 106. Once the user gesture signal 117 is received by the first computer assembly 102 from the gesture-sensing device 106, the first computer assembly 102 is configured to process the user gesture signal 117. For instance, the first computer assembly 102 may analyze the user gesture signal 117, and compare the user gesture signal 117 to a pre-defined set of gestures (data stored in memory). These pre-defined sets of gestures may be associated with one or more functions for the control of (directing, manipulating, and/or managing) the telepresence communications between the first computer assembly 102 and the second computer assembly 202. The pre-defined set of gestures may also include functions to control and/or manage the operations of the first computer assembly 102.

The first computer assembly 102 is also configured to control a privacy aspect of the telepresence data unit 115 to be transceived, via the communication network 103, between the first computer assembly 102 and the second computer assembly 202, depending on the content of the user gesture signal 117 that was received from the gesture-sensing device 106. For instance, the first computer assembly 102 may analyze the user gesture signal 117 and determine that the user (for example, the surgeon) wishes to control a privacy aspect of the telepresence information that may be exchanged (exchanged communication) during the telepresence communications session. The control may include, and is not limited to, pausing the telepresence information, blocking or otherwise censoring some amount of the telepresence information (e.g., a patient's face, etc.), and/or cancelling or stopping the potential communications of the telepresence information. For the case where the user (e.g., a surgeon), for example, wishes to pause the telepresence information between the first computer assembly 102 and the second computer assembly 202, the user gesture signal 117 is interpreted by the first computer assembly 102, and a pause signal may be transmitted to the second computer assembly 202 from the first computer assembly 102. The pause signal may cause both the first computer assembly 102 and second computer assembly 202 to pause the exchange (exchange communication) of their respective telepresence information from potentially being transceived (exchanged). In some embodiments, connections from the first computer assembly 102 (or the second computer assembly 202, or both) to input and output devices (such as cameras, audio systems, video systems, etc.) may be suspended, and this arrangement may help to prevent private data from inadvertently being captured and exchanged while the pause (in telepresence information to be transceived) is in effect.

In some embodiments, a first audio system 114 may be connected to the first computer assembly 102, the second computer assembly 202, or both. The first audio system 114 is configured to transmit and receive audio signals to and from the first computer assembly 102 and the second computer assembly 202. In some embodiments, the first audio system 114 may include a microphone of the first audio system 114. The microphone of the first audio system 114 may be connected to the first computer assembly 102, in which the first computer assembly 102, in use, provides an audio signal received from the microphone of the first audio system 114 to the second computer assembly 202 once the first computer assembly 102 and the second computer assembly 202 are network connected (with each other) via the communication network 103.

For some embodiments, the first computer assembly 102 may include a first audio system 114. The first audio system 114 may be connected (connected either with wire or wirelessly) to the first computer assembly 102, in which the first computer assembly 102 provides the audio signal to the first audio system 114, in which the audio signal is to be received from the second computer assembly 202 once the first computer assembly 102 and the second computer assembly 202 are network connectable (with each other) via the communication network 103.

The first computer assembly 102 is configured to provide a display signal (such as the signal provided by the remote controllable camera 108) to be displayed on the second display system 204 of the second computer assembly 202.

It will be appreciated that the first audio system 114, the microphone of the first audio system 114, the speaker (known and not depicted) of the first audio system 114, the second display system 204, and any other device may be connected to the first computer assembly 102 or the second computer assembly 202 using a combination of networking and connection protocols that include, but are not limited to, the USB (TRADEMARK) system, the BLUETOOTH system (TRADEMARK), the THUNDERBOLT (TRADEMARK) system, analog audio (e.g., RCA), TRS (Tip-Ring-Sleeve) connectors, and the HDMI (TRADEMARK) system. Other devices, such as the gesture-sensing device 106 (and/or remote controllable laser pointer device, audio system, etc.) may be connected to its respective computer assembly (e.g., the first computer assembly 102 or the second computer assembly 202) using the USB (Universal Serial Bus), the BLUETOOTH (TRADEMARK) system, the THUNDERBOLT (TRADEMARK) system, or any other connection protocol.

In some embodiments, the first computer assembly 102 or the second computer assembly 202 may integrate one or more of the devices shown in FIG. 1. For instance, in some embodiments, the first audio system 114 includes (and is not limited to) a speaker and a microphone. The first display system 104 includes (and is not limited to), a screen system. The remote controllable camera 108 may or may not be an integral part of the first display system 104.

Embodiments of the first computer assembly 102 include (and are not limited to) laptop computers, personal computers, and mobile devices such as cell phones, tablets, and convertible laptop computers (i.e., computers that can operate as both a laptop and a tablet). It will also be understood that the first computer assembly 102 and second computer assembly 202 may include commercially available elements of a computer that include, but are not limited to, motherboards, CPUs (Central Processing Units), memory (any type of memory), persistent data storage (such as hard drives and SSDs), secondary storage devices (such as the BLU-RAY (TRADEMARK) recorder, removable flash memory), monitors, internal speakers, keyboards, and pointing devices such as a mouse, a trackpad, and/or a trackball. For other embodiments, the first computer assembly 102, the second computer assembly 202, or both may be implemented in a cloud computing environment. For this embodiment, the first computer assembly 102, second computer assembly 202, or both may be implemented on a virtual private server (VPS) that is operating on a shared-resource server. This may include, but is not limited to, cloud computing services (known and not discussed here), etc.

The telepresence apparatus 100 may be used to obviate the need for a support representative to be on-site during a procedure by allowing the support representative to remotely communicate with the team performing the procedure. For instance, in the example of an operating room, medical implant manufacturers typically require that surgical implant support representatives be physically available in the operating room to support medical personnel during surgical procedures. The representative provides technical support, such as, but not limited to, demonstrating how to use the instrumentation to implant the medical device. Having support personnel available during the procedure is important because of the ongoing technological advancements in these devices and the unfamiliarity of the surgeon and nurse(s) to the procedure and medical devices and instruments.

Providing adequate in-operating-room support has become challenging for medical implant manufacturers. For instance, operating room scheduling and overlapping surgeries at different hospitals may lead to a shortage of on-site (i.e., in the operating room) representatives to support the medical devices. This may have the undesirable effect of requiring the doctors and nurses to troubleshoot the equipment on their own or postpone or delay the surgeries.

Furthermore, since the representative (support person) may only be physically present in one location at a time, medical device manufacturers may be required to hire more representatives, which further erodes the profit margin on the medical implant. For instance, some orthopedic companies report that more than two thirds (⅔ or approximately 66%) of the expenses are attributable to salaries and commissions for the surgical implant representatives. In some embodiments, the increased staffing requirements for simultaneous surgeries (for instance) have prevented some orthopedic companies from pursuing or accepting business opportunities.

The telepresence apparatus 100 may allow for support representatives (in this embodiment, medical implant support personnel, or technician, with a high level of clinical expertise) to be available remotely to assist the operating-room staff with the instrumentation and surgical steps. That is, the representative no longer has to be physically present in the operating room to support the surgical team. Thus, for example, the representative can remotely service multiple operating rooms simultaneously. This may contribute towards a cost savings to orthopedic companies while improving the quality of service during operating procedures to the operating-room staff. Furthermore, since the support representative (technician) is no longer required to be physically present in each location, the technician may support more procedures simultaneously. This flexibility can provide several advantages. For instance, the telepresence apparatus may allow a remotely-located technician to support multiple procedures in multiple locations without the need to be physically present in any of the multiple locations. That is, the remotely-located technician can be "virtually present" in the multiple locations without being physically present in the multiple locations at the same time.

The telepresence apparatus 100 may allow for a remotely-located technician to support multiple back-to-back procedures in geographically disparate locations. For instance, the same remotely-located technician may be able to support, virtually and using the telepresence apparatus, a procedure in New York City and a procedure in Los Angeles in a single afternoon. This would be extremely difficult if the technician was required to be physically present in both locations.

The telepresence apparatus 100 may allow a veteran technician to support multiple procedures simultaneously. This can help to ensure that the multiple procedures each have adequate experienced support. Previously, without the telepresence apparatus, a shortage of veteran technicians might have led to inexperienced technicians, having little to no knowledge of the domain, being deployed in the field.

The telepresence apparatus 100 may allow a technician to use other, non-verbal, means of communication to direct a user of the telepresence apparatus. For instance, in the example of an orthopedic surgical procedure, the technician may be able to use the telepresence apparatus to demonstrate, via a video clip, how a medical tool should be used. In contrast, when a technician is physically present during a procedure, the technician may be limited in how he or she can communicate with the surgical staff (e.g., verbal/visual only). For instance, animated simulations of medical instruments and how the medical instruments fit together may be useful. Technical representatives may also receive and respond to questions from surgical staff about technical specifications regarding implants during a surgery (the telepresence apparatus 100 may allow that information to be presented via the first display system 104).

It will be appreciated that the subject matter in this disclosure may be applicable to many different domains, and not just for orthopedic surgery support. For instance, the present disclosure may apply to all aspects of surgical domains such as (but not limited to) plastic surgery, general surgery, veterinary surgery, and other surgical procedures. Furthermore, the present disclosure may also be usable in non-surgical and/or non-medical environments (for instance, in remote learning or remote training environments). For instance, the present disclosure may be used in any environment where a remotely located subject matter expert may be utilized to advise and interact with trainees. Examples include, but are not limited to, allowing an instructor to remotely advise and interact effectively with trainees to learn hands-on skill-sets, automotive training (e.g., mechanics training), military training, and aerospace training and inspection.

Referring to the embodiment as depicted in FIG. 1, the telepresence apparatus 100 is configured to allow (facilitate) a remotely-located technician, who uses the second computer assembly 202, to monitor and interact with multiple surgical procedures located at multiple remote locations. The technician uses the second computer assembly 202, and may bi-directionally monitor multiple surgical procedures using video, audio, and interactive presentations simultaneously. Moreover, the telepresence apparatus 100 allows the operating-room staff to engage the representative (also called technical support or technician), via the first computer assembly 102, on an as-needed basis. The technician may also provide presentations to the operating-room staff in the form of video clips (via the first display system 104 and/or first audio system 114), audio/verbal discussions (via the first audio system 114), a remote controllable laser pointer device 110 to point physically to instruments, and/or to bring up documentation and technical specifications on the first display system 104.

It will be appreciated that additional features or functions may be incorporated into the telepresence apparatus 100 as required. For instance, the telepresence apparatus 100 may be designed modularly in such a way that the functionality of the telepresence apparatus 100 may be extended as new media formats are defined.

For the case of an orthopedic surgery, the remotely-located technician may use the telepresence apparatus 100, via the second computer assembly 202, to interact with multiple teams of operating-room staff who are performing procedures, surgical procedures, or orthopedic surgical procedures. In this example, the telepresence apparatus 100 may assist the operating-room staff in any one or a combination of the following ways: (1) maintain two-way video and verbal communication between operating-room staff and the technician while preserving the sterile field, (2) remotely demonstrate how to use surgical instrumentation, (3) remotely identify individual and/or groups of surgical instruments (to ensure that the operating-room staff have a complete set of instruments for a procedure, or know which specific instrument to use at a given point during a procedure), (4) enable the technician to provide direction in a time-critical manner, (5) ensure that the operating-room staff are comfortable with the surgical procedure by ensuring access to a clinical expert (that is, the technician, etc.) and (6) save valuable surgical time relative to the known telepresence systems where the remote controllable laser pointer device is paired with, and its movement is synchronized with (and, therefore, comparatively slowed by) the movement of a remote controllable camera (in which the camera may be configured to pan, tilt and/or zoom in order to re-aim the remote controllable laser pointer device). In sharp contrast, the telepresence apparatus 100 utilizes a remote controllable laser pointer device 110 (that is located in the first physical site 101) that may be configured to quickly react (preferably, almost instantaneously) when directed by the remote technician (who is located in the second physical site 201). This may be an important issue for the case where the remote controllable camera 108 is too slow to operate (and may lead to unwanted delays for medical procedures where quicker response times may be critical in a surgical environment located in the first physical site 101). It will be appreciated that the remote controllable laser pointer device 110 (controllable, at least in part, independently of the remote controllable camera 108) may be configured to allow the remote operator, and in turn the scrub nurse, to stay several steps (one or two steps) ahead of the surgeon, which may be a highly-valued aspect of surgical assistance.

It will be appreciated that the telepresence apparatus 100 may be configured to assist the operating-room staff in other ways. It will be further appreciated that when the telepresence apparatus 100 is deployed in other domains (e.g., that are not orthopedic surgeries), the telepresence apparatus 100 is configured to assist a trainee and/or the user in various ways and/or in ways that depend on the specific domain requirements.

Preferably, the telepresence apparatus 100 includes bi-directional audio teleconferencing and/or bi-directional video teleconferencing, and a remote controllable laser pointer device 110. The remote controllable laser pointer device 110 may be configured in various shapes and sizes (e.g., not just a pointer, and may include the functionality to encircle physical items). For instance, for the case where surgical representatives use a remote controllable laser pointer device 110 in surgeries, it may be a frustrating experience for the scrub nurse if the surgical representative just points the laser light at the medical instrument as the nurse may have trouble picking up (detecting) the red dot (the light image produced by the remote controllable laser pointer device 110). Preferably, the remote controllable laser pointer device 110 is configured to emit a tight, fast moving laser-light pattern, curved pattern, or a circle (and any equivalent thereof) to make the reflected laser image relatively easier to pick up (detect) with the human eye. For instance, the laser light may include a neon, a yellow and/or a green laser light that is known to be relatively easier for the human eye to see (perceive).

The telepresence apparatus 100 may also include mechanisms for the remote support staff (technicians) to present different forms of media (such as animations, video, and three-dimensional models, etc.) of the procedures and instruments, to bookmark and annotate these forms of media both prior to surgery and during surgery, and to provide additional real-time information to the operating-room staff.

Referring to the embodiment as depicted in FIG. 1 (and in accordance with a second general aspect), a telepresence apparatus 100 includes (and is not limited to) a second computer assembly 202 configured to be network connectable with a first computer assembly 102 via a communication network 103. The second computer assembly 202 is configured to be connectable to a camera controller system 208. The camera controller system 208 is configured to control a remote controllable camera 108. The remote controllable camera 108 is configured to be connectable to the first computer assembly 102. The remote controllable camera 108 is configured to be controllable by the camera controller system 208 once the first computer assembly 102 and the second computer assembly 202 are network connected via the communication network 103.

The second computer assembly 202 is configured to be connectable to a laser pointer controller system 210. The laser pointer controller system 210 is configured to control a remote controllable laser pointer device 110. The remote controllable laser pointer device 110 is configured to be connectable to the first computer assembly 102. The remote controllable laser pointer device 110 is configured to be controllable by the laser pointer controller system 210 once the first computer assembly 102 and the second computer assembly 202 are network connected via the communication network 103.

The second computer assembly 202 is configured to (A) transmit (to the first computer assembly 102 via the communication network 103) camera-control instructions (to be) provided by the camera controller system 208, and (B) transmit (to the first computer assembly 102 via the communication network 103) laser-control instructions (to be) provided by the laser pointer controller system 210. This is done in such a way that: (a) the camera-control instructions and the laser-control instructions, in use, independently control the remote controllable camera 108 and the remote controllable laser pointer device 110 (respectively), and (b) the camera-control instructions and the laser-control instructions, in use, spatially orient the remote controllable camera 108 and the remote controllable laser pointer device 110 along different spatial orientations relative to each other.

It will be appreciated that in order to track (follow) the laser light, the FOV (field of view) of the remote controllable camera 108 may be positioned (oriented) to capture (view), at least in part, the laser light (to be provided by the remote controllable laser pointer device 110) that is reflected from the object located in the first physical site 101 (such as, the surgical room). The alignment (pointing) of the remote controllable laser pointer device 110 is not necessarily aligned (pointed) with the remote controllable camera 108 (since the remote controllable camera 108 has a FOV (field of view) that is sufficiently wide enough to capture the reflected laser light).

Referring to the embodiment as depicted in FIG. 1 (and in accordance with a second general aspect), a telepresence apparatus 100 includes (and is not limited to) a second memory assembly 216. The second memory assembly 216 is configured to interface with a second computer assembly 202 configured to be network connectable with a first computer assembly 102 via a communication network 103. The second computer assembly 202 is configured to be connectable to a camera controller system 208. The camera controller system 208 is configured to control a remote controllable camera 108. The remote controllable camera 108 is configured to be connectable to the first computer assembly 102. The remote controllable camera 108 is configured to be controllable by the camera controller system 208 once the first computer assembly 102 and the second computer assembly 202 are network connected via the communication network 103. The second computer assembly 202 is configured to be connectable to a laser pointer controller system 210. The laser pointer controller system 210 is configured to control a remote controllable laser pointer device 110. The remote controllable laser pointer device 110 is configured to be connectable to the first computer assembly 102. The remote controllable laser pointer device 110 is configured to be controllable by the laser pointer controller system 210 once the first computer assembly 102 and the second computer assembly 202 are network connected via the communication network 103.

The second memory assembly 216 is also configured to tangibly store programmed coded instructions 218. The programmed coded instructions 218 are configured to urge the second computer assembly 202 to perform a first operation 812. The first operation 812 includes (A) transmitting (from the second computer assembly 202 to the first computer assembly 102 via the communication network 103) camera-control instructions to be provided by the camera controller system 208, and (B) transmitting (from the second computer assembly 202 to the first computer assembly 102 via the communication network 103) laser-control instructions (to be) provided by the laser pointer controller system 210. This is done in such a way that: (a) the camera-control instructions and the laser-control instructions, in use, independently control the remote controllable camera 108 and the remote controllable laser pointer device 110, respectively, and (b) the camera-control instructions and the laser-control instructions, in use, spatially orient the remote controllable camera 108 and the remote controllable laser pointer device 110 along different spatial orientations relative to each other.

Figure 9:
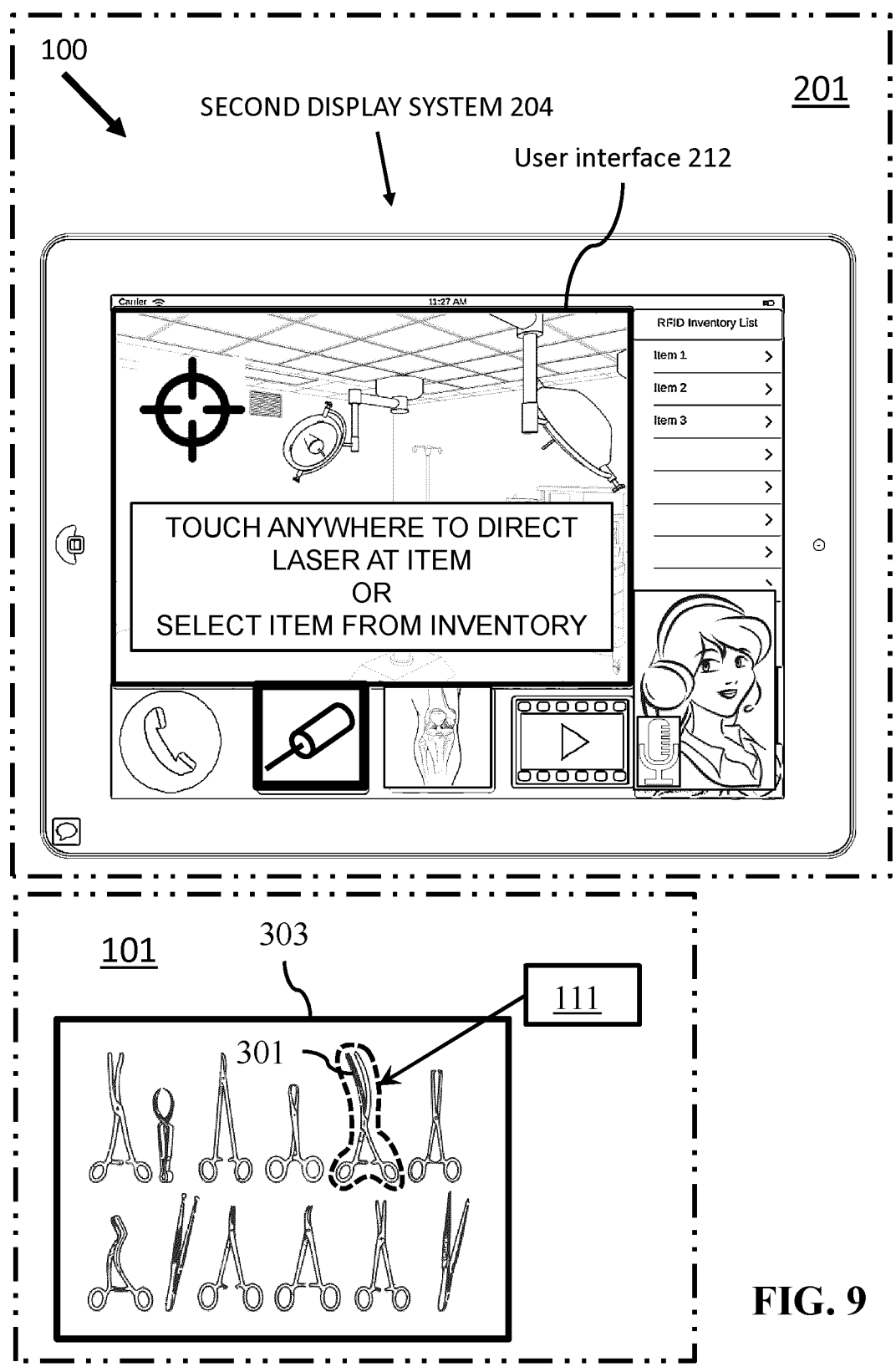

Referring to the embodiment as depicted in FIG. 1 and FIG. 9 (and in accordance with a third general aspect), a telepresence apparatus 100 includes and is not limited to (comprises) a second computer assembly 202 configured to be network connectable with a first computer assembly 102 via a communication network 103. The second computer assembly 202 is configured to be connectable to a camera controller system 208. The camera controller system 208 is configured to control a remote controllable camera 108. The remote controllable camera 108 is configured to be connectable to the first computer assembly 102. The remote controllable camera 108 is configured to be controllable by the camera controller system 208 once the first computer assembly 102 and the second computer assembly 202 are network connected via the communication network 103.

The second computer assembly 202 is configured to be connectable to a laser pointer controller system 210. The laser pointer controller system 210 is configured to control a remote controllable laser pointer device 110. The remote controllable laser pointer device 110 is configured to be connectable to the first computer assembly 102. The remote controllable laser pointer device 110 is configured to be controllable by the laser pointer controller system 210 once the first computer assembly 102 and the second computer assembly 202 are network connected via the communication network 103.

The second computer assembly 202 is also configured to interface with a second display system 204. The second computer assembly 202 is configured to display an image, and/or to show an animation of how the surgical instruments and/or the surgical implants go together and function. The second computer assembly 202 is also configured to transmit (to the first computer assembly 102 via the communication network 103) an image of a surgical instrument 301. This is done in such a way that the first computer assembly 102, in use, urges a first display system 104 of the first computer assembly 102 to display the image of the surgical instrument 301 to a user positioned proximate to the first computer assembly 102. More specifically, the first computer assembly 102, in use, transmits a display command (along with the image) to the first display system 104 of the first computer assembly 102 to display the image of the surgical instrument 301 (which was received from the second computer assembly 202 via the communication network 103) to the user positioned proximate to the first computer assembly 102.

The second computer assembly 202 is also configured to transmit (to the first computer assembly 102 via the communication network 103) laser-control instructions (to be) provided by the laser pointer controller system 210. This is done in such a way that the laser-control instructions, in use, urge the remote controllable laser pointer device 110 to issue a light pattern. The light pattern, in use, identifies (preferably, matches an outline or contours of) the surgical instrument 301 to the user positioned proximate to the first computer assembly 102 (useful when putting instruments back in their correct spot or position located in a storage tray 303). The light pattern may include a single point, a small fast-moving circular pattern to improve the identification of which specific medical instrument is being pointed to, and/or the light pattern 111 may match the contours of the medical instrument 301, etc.

Referring to the embodiment as depicted in FIG. 1 and FIG. 9 (and in accordance with a third general aspect), a telepresence apparatus 100 includes and is not limited to (comprises) a second memory assembly 216. The second memory assembly 216 is configured to interface with a second computer assembly 202 configured to be network connectable with a first computer assembly 102 via a communication network 103. The second computer assembly 202 is configured to be connectable to a camera controller system 208. The camera controller system 208 is configured to control a remote controllable camera 108. The remote controllable camera 108 is configured to be connectable to the first computer assembly 102. The remote controllable camera 108 is configured to be controllable by the camera controller system 208 once the first computer assembly 102 and the second computer assembly 202 are network connected via the communication network 103. The second computer assembly 202 is configured to be connectable to a laser pointer controller system 210. The laser pointer controller system 210 is configured to control a remote controllable laser pointer device 110. The remote controllable laser pointer device 110 is configured to be connectable to the first computer assembly 102. The remote controllable laser pointer device 110 is configured to be controllable by the laser pointer controller system 210 once the first computer assembly 102 and the second computer assembly 202 are network connected via the communication network 103. The second computer assembly 202 is also configured to interface with a second display system 204. In accordance with an option, there is provided an interface on the first display system 104 that is not touched and/or utilized by anyone sterile in the first physical site 101. The interface of the first display system 104 is configured to allow the circulating nurse (non-sterile nurse) to interface with the first computer assembly 102.

The second memory assembly 216 is also configured to tangibly store programmed coded instructions 218. The programmed coded instructions 218 are configured to urge the second computer assembly 202 to perform a first operation 814. The first operation 814 includes transmitting (from the second computer assembly 202 to the first computer assembly 102 via the communication network 103) an image of a surgical instrument 301. This is done in such a way that the first computer assembly 102, in use, urges a first display system 104 of the first computer assembly 102 to display the image of the surgical instrument 301 to a user positioned proximate to the first computer assembly 102. More specifically, the first computer assembly 102, in use, transmits a display command (along with the image) to the first display system 104 of the first computer assembly 102 to display the image of the surgical instrument 301 (which was received from the second computer assembly 202 via the communication network 103) to the user positioned proximate to the first computer assembly 102.

The programmed coded instructions 218 are configured to urge the second computer assembly 202 to perform a second operation 816. The second operation 816 includes transmitting (from the second computer assembly 202 to the first computer assembly 102 via the communication network 103) laser-control instructions (to be) provided by the laser pointer controller system 210. This is done in such a way that the laser-control instructions, in use, urge the remote controllable laser pointer device 110 to issue a light pattern. The light pattern, in use, identifies (preferably, matches an outline or contours of) the surgical instrument 301 to the user positioned proximate to the first computer assembly 102 (useful when putting instruments back in the correct spot positioned or located in a storage tray 303). Although the remote controllable laser pointer device may assist the surgical staff in highlighting a surgical instrument (such as, the position in which the surgical instrument belongs in the surgical tray), the main function of the laser pointer includes highlighting (in use) a surgical instrument when the surgical instrument is required by the surgeon during the surgical procedure. If necessary, additional information on the correct assembly and use of the surgical instrument may be provided on the computer screen viewable by staff in the surgical field. The term "surgical instrument" may include an orthopedic part and/or a surgical part.

Figure 2A:
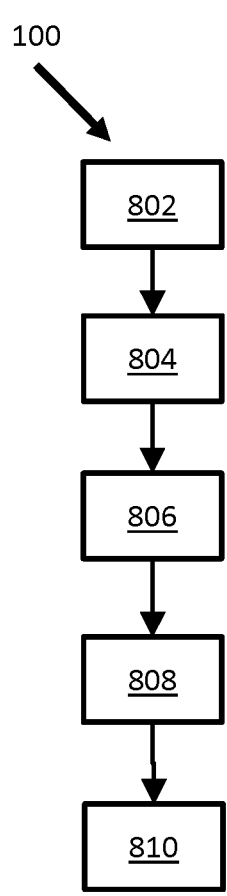
FIGS. 2A, 2B and 2C depict schematic view of methods for operating the aspects of the telepresence apparatus of FIG. 1.
Figure 2B:
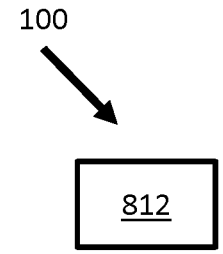
Figure 2C:
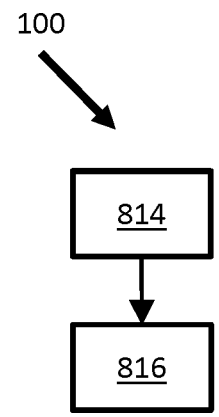

FIGS. 2A, 2B and 2C depict schematic views of methods for operating the aspects of the telepresence apparatus 100 of FIG. 1.

Referring to the embodiment as depicted in FIG. 2A, in accordance with a first aspect, there is provided a method. The method is for operating the first computer assembly 102 of the telepresence apparatus 100 (as depicted in FIG. 1). The method includes (and is not limited to) a first operation 802, a second operation 804, a third operation 806, a fourth operation 808 and a fifth operation 810. The method is executable by the first computer assembly 102. The method may be implemented as programmed coded instructions 118 configured to urge the first computer assembly 102 to execute operations. For instance, a first memory assembly 116 is configured to interface with a first computer assembly 102, and the first memory assembly 116 is also configured to tangibly store the programmed coded instructions 118.

The first operation 802 includes (and is not limed to) receiving, by the first computer assembly 102, a telepresence data unit 115. The telepresence data unit 115 is provided by a remote controllable camera 108 and a first audio system 114 (to the first computer assembly 102. Once the first operation 802 is completed, operational control is transferred to the second operation 804.

The second operation 804 includes (and is not limed to) transmitting, from the first computer assembly 102, the telepresence data unit 115 to a second computer assembly 202 via a communication network 103. The first computer assembly 102 is configured to: (A) be network connectable with the communication network 103, and (B) be network connectable with the second computer assembly 202. The second computer assembly 202 is configured to be network connectable with the communication network 103. The first computer assembly 102 and the second computer assembly 202 are also configured to be network connectable (with each other) via the communication network 103. Once the second operation 804 is completed, operational control is transferred to the third operation 806.

The third operation 806 includes (and is not limed to) receiving, by the first computer assembly 102, a user gesture signal 117 from the gesture-sensing device 106. The gesture-sensing device 106 is configured to be connected to the first computer assembly 102. The gesture-sensing device 106 is configured to: (A) detect a user gesture to be provided by a user positioned proximate to the first computer assembly 102, and (B) generate the user gesture signal 117 associated with the user gesture that was detected (in response to detection of the user gesture provided by the user positioned proximate to the first computer assembly 102). Once the third operation 806 is completed, operational control is transferred to the fourth operation 808.

The fourth operation 808 includes (and is not limed to) computing, by the first computer assembly 102, whether the user gesture signal 117, which was received by the first computer assembly 102, matches a predetermined user gesture stored in a first memory assembly 116 of the first computer assembly 102. Once the fourth operation 808 is completed, operational control is transferred to the fifth operation 810.

The fifth operation 810 includes (and is not limed to) computing, by the first computer assembly 102, whether to suspend transmission of an aspect of the telepresence data unit 115 to the second computer assembly 202 via the communication network 103 depending on the match made between the user gesture signal 117 and the predetermined user gesture.

It will be appreciated that the second computer assembly 202 may include a computing device having the functionality described herein for the second computer assembly 202, examples of which include a personal computer, a laptop or notebook personal computer, a tablet computer, a smartphone, or any computing device capable of controlling remote devices and having an audio system, a display system, and some means of inputting user input (such as, for example, a touchscreen, keyboard, mouse, trackball, and/or touchpad), and any equivalent thereof.

Referring to the embodiment as depicted in FIG. 2B, in accordance with a second aspect, there is provided a method. The method is for operating a telepresence apparatus 100. The telepresence apparatus 100 includes a second computer assembly 202 configured to be network connectable with a first computer assembly 102 via a communication network 103. The second computer assembly 202 is configured to be connectable to a camera controller system 208. The camera controller system 208 is configured to control a remote controllable camera 108. The remote controllable camera 108 is configured to be connectable to the first computer assembly 102. The remote controllable camera 108 is configured to be controllable by the camera controller system 208 once the first computer assembly 102 and the second computer assembly 202 are network connected via the communication network 103. The second computer assembly 202 is configured to be connectable to a laser pointer controller system 210. The laser pointer controller system 210 is configured to control a remote controllable laser pointer device 110. The remote controllable laser pointer device 110 is configured to be connectable to the first computer assembly 102. The remote controllable laser pointer device 110 is configured to be controllable by the laser pointer controller system 210 once the first computer assembly 102 and the second computer assembly 202 are network connected via the communication network 103. The method includes and is not limited to (comprises) a first operation 812. The first operation 812 includes (A) transmitting (from the second computer assembly 202 to the first computer assembly 102 via the communication network 103) camera-control instructions (to be) provided by the camera controller system 208, and (B) transmitting (from the second computer assembly 202 to the first computer assembly 102 via the communication network 103) laser-control instructions (to be) provided by the laser pointer controller system 210. This is done in such a way that: (a) the camera-control instructions and the laser-control instructions, in use, independently control the remote controllable camera 108 and the remote controllable laser pointer device 110 (respectively), and (b) the camera-control instructions and the laser-control instructions, in use, spatially orient the remote controllable camera 108 and the remote controllable laser pointer device 110 along different spatial orientations relative to each other.

Referring to the embodiment as depicted in FIG. 1, FIG. 2C and FIG. 9, in accordance with a second aspect, there is provided a method. The method is for operating a telepresence apparatus 100. The telepresence apparatus 100 includes a second computer assembly 202 configured to be network connectable with a first computer assembly 102 via a communication network 103. The second computer assembly 202 is configured to be connectable to a camera controller system 208. The camera controller system 208 is configured to control a remote controllable camera 108. The remote controllable camera 108 is configured to be connectable to the first computer assembly 102. The remote controllable camera 108 is configured to be controllable by the camera controller system 208 once the first computer assembly 102 and the second computer assembly 202 are network connected via the communication network 103. The second computer assembly 202 is configured to be connectable to a laser pointer controller system 210. The laser pointer controller system 210 is configured to control a remote controllable laser pointer device 110. The remote controllable laser pointer device 110 is configured to be connectable to the first computer assembly 102. The remote controllable laser pointer device 110 is configured to be controllable by the laser pointer controller system 210 once the first computer assembly 102 and the second computer assembly 202 are network connected via the communication network 103. The second computer assembly 202 is also configured to interface with a second display system 204.

The method includes and is not limited to (comprises) a first operation 814. The first operation 814 includes transmitting (from the second computer assembly 202 to the first computer assembly 102 via the communication network 103, an image of a surgical instrument 301 in such a way that the first computer assembly 102, in use, urges a first display system 104 of the first computer assembly 102 to display the image of the surgical instrument 301 to a user positioned proximate to the first computer assembly 102. More specifically, the first computer assembly 102, in use, transmits a display command (along with the image) to the first display system 104 of the first computer assembly 102 to display the image of the surgical instrument 301 (which was received from the second computer assembly 202 via the communication network 103) to the user positioned proximate to the first computer assembly 102.

The method further includes a second operation 816. The second operation 816 includes transmitting (from the second computer assembly 202 to the first computer assembly 102 via the communication network 103) laser-control instructions (to be) provided by the laser pointer controller system 210. This is done in such a way that the laser-control instructions, in use, urge the remote controllable laser pointer device 110 to issue a light pattern, in which the light pattern, in use, identifies (preferably, matches an outline or contours of) the surgical instrument 301 to the user positioned proximate to the first computer assembly 102 (useful when putting instruments back in their correct spots located in a storage tray 303). Although the remote controllable laser pointer device may assist the surgical staff in highlighting a surgical instrument (such as, the position in which the surgical instrument belongs in the surgical tray), the main function of the laser pointer includes highlighting (in use) a surgical instrument when the surgical instrument is required by the surgeon during the surgical procedure. If necessary, additional information on the correct assembly and use of the instrument may be provided on the first display system 104 viewable by staff in the surgical field.

Figure 3:
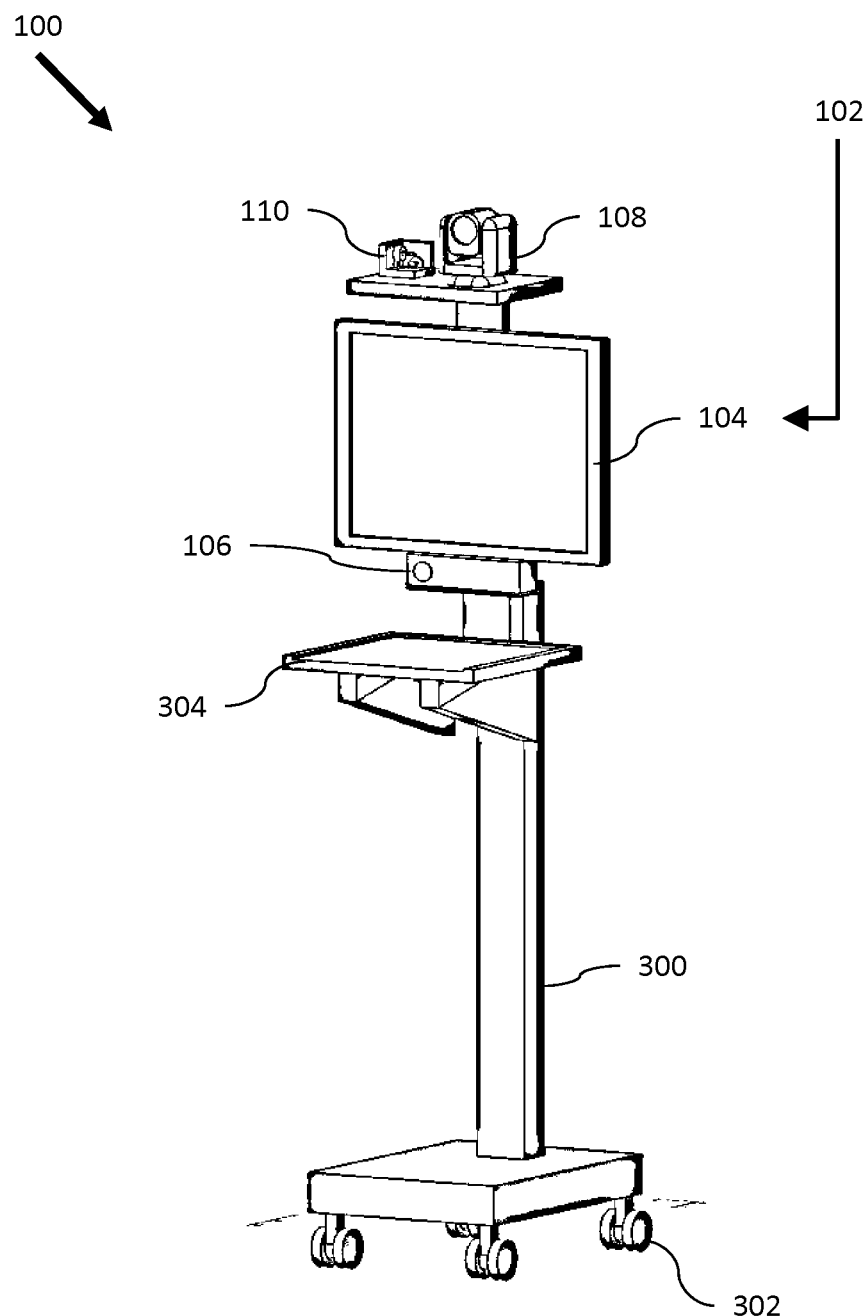
FIG. 3 and FIG. 4 depict perspective front views of the telepresence apparatus of FIG. 1.
Figure 4:
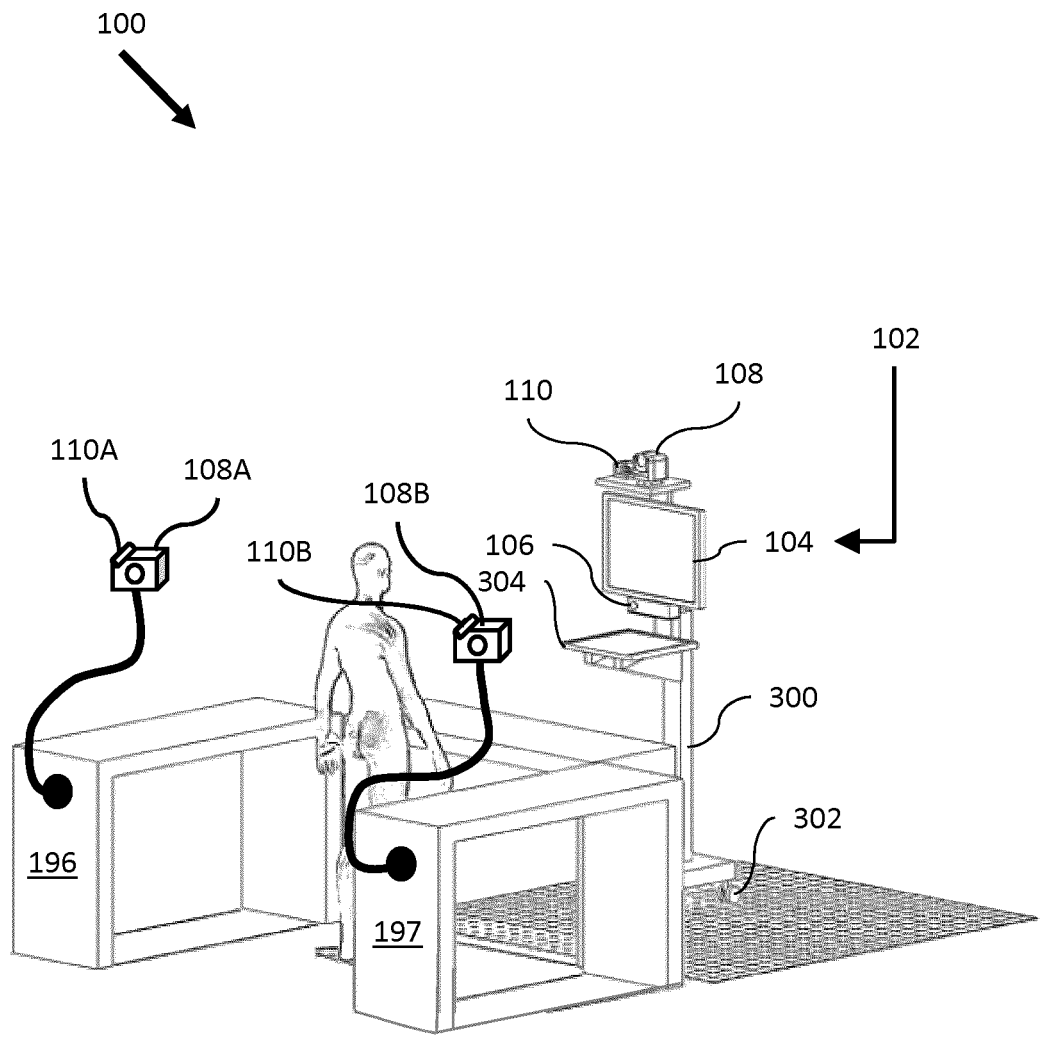

FIG. 3 and FIG. 4 depict perspective front views of the telepresence apparatus 100 of FIG. 1.

Referring to the embodiments as depicted in FIG. 3 and FIG. 4, the first computer assembly 102 of the telepresence apparatus 100 is depicted. The first computer assembly 102 includes the remote controllable laser pointer device 110. It will be appreciated that the technician (located in the second physical site 201) may direct orientation of the remote controllable laser pointer device 110 where he wants by moving the laser pointer indicator that is located on an interface shown on the second display system 204, manipulating a joy stick, a trackball, a button on a key board, movement of an arrow key on a keyboard, etc., and any equivalent thereof. The remote controllable laser pointer device 110 is configured to (A) accept (receive) laser-pointing instructions, via the communication network 103, from the laser pointer controller system 210 (as depicted in FIG. 1) of the second computer assembly 202, and (B) point to a desired (predetermined) target (one or more targets) located in the vicinity of the first computer assembly 102 (in response to the nature of the instructions). Preferably, the remote controllable laser pointer device 110 is configured to accept (receive) instructions, via the communication network 103, from the laser pointer controller system 210 (as depicted in FIG. 1) of the second computer assembly 202, and (C) draw an outline on a desired (predetermined) target (one or more targets) located in or near the vicinity of the first computer assembly 102. The technician (which is located in the second physical site 201) may view the laser light (which was emitted by the laser pointer controller system 210 and subsequently reflected from an object located in the first physical site 101) via the remote controllable camera 108 (which is configured to be controlled by the camera controller system 208 under the manipulations of the technician located in (or near) the second physical site 201, as depicted in FIG. 1). The terms "user" and "technician" may be used interchangeably. The user may include a surgeon (located in the first physical site 101), a doctor (located in the first physical site 101), a nurse (located in the first physical site 101), a technician (located in the second physical site 201), a remotely-located support representative (located in the second physical site 201), a representative (located in the second physical site 201), a remote support staff (located in the second physical site 201), an individual technical support technician (located in the second physical site 201). Preferably, the remote controllable laser pointer device 110 is configured to outline shapes. In accordance with an option, a light-scattering filter is configured to scatter, at least in part, the light emitted from the remote controllable laser pointer device 110 to outline shapes (around an object). The light emitted from the remote controllable laser pointer device 110 may be made to flash ON and OFF (if desired).

Preferably, the remote controllable laser pointer device 110 is mountable on a movement platform. The movement platform has motors configured to move the remote controllable laser pointer device 110 in a desired alignment (predetermined alignment, or direction), such as allowing the remote controllable laser pointer device 110 to move in six degrees of freedom. The motors may be controlled by a motor controller configured to accept instructions remotely, directly or indirectly, from the second computer assembly 202. The movement platform is configured to move the remote controllable laser pointer device 110 in such a way as to trace a shape around an object.

The first computer assembly 102 also includes a remote controllable camera 108. The remote controllable camera 108 is configured to pan, tilt, and/or zoom according to instructions received, via the communication network 103, from the camera controller system 208 of the second computer assembly 202. The technician located in (or near) the second physical site 201 may remotely view the first physical site 101 surrounding the first computer assembly 102 (preferably, without the need for physically moving the first computer assembly 102 within the first physical site 101). Examples of the remote controllable camera 108 include, but are not limited to, the PANASONIC (TRADEMARK) Model Number AW-HE40SKPJ camera, and any equivalent thereof.

The first computer assembly 102 also includes bi-directional audio communication device and/or a bi-directional visual communication device, which may be integrated with the first display system 104. The first display system 104 may incorporate the functionality of the first audio system 114 (as depicted in FIG. 1). The first display system 104 may be connected to the first computer assembly 102 via a cable or wirelessly in such a way that both audio and video data are transmittable from the first computer assembly 102 to the first display system 104. The first display system 104 may include a microphone (not shown). The bi-directional audio/visual communication may be established using a video chat program, such as SKYPE (TRADEMARK) software (manufactured by MICROSOFT headquartered in the U.S.A.), etc., and any equivalent thereof.

The first computer assembly 102 includes the gesture-sensing device 106. The gesture-sensing device 106 is configured to detect (facilitate, collect) in-the-air gestures from a user. The gesture-sensing device 106 may include a microphone (which is considered a part of the first audio system 114 as depicted in FIG. 1).

The first computer assembly 102 is configured to be supported by a portable (movable) cart assembly 300. The components of the first computer assembly 102 may be affixed, removable or otherwise, to the cart assembly 300. The cart assembly 300 may be a commercially-available standing workstation commonly deployed in a healthcare environment. The cart assembly 300 (portable cart assembly) includes casters 302 configured to permit rolling movement of the cart assembly 300. The casters 302 may be lockable in such a way that the cart assembly 300 remains in place once the casters 302 are locked. The cart assembly 300 may include a working platform 304 (such as a keyboard shelf).

The first computer assembly 102 includes an input device for accepting user inputs, such as a mouse, keyboard, trackball, trackpad, pen input, etc. (in which the inputs may be displayed on the first display system 104). The physical input device can be placed, at least in part, on the working platform 304. Orthopedic medical tools may be placed on the working platform 304. The working platform 304 may further include a drawer for storing assorted medical tools and accessories (e.g., input devices, pens, tools, orthopedic tools, etc.).

Referring to the embodiment as depicted in FIG. 4, the first computer assembly 102 is deployed in the first physical site 101 (of FIG. 1). A user is oriented towards the first computer assembly 102 in such a way that the user can view and hear audio output from the audio system and/or a visual output from the first display system 104 (or any audio can be captured by the audio system and/or any video can be captured by the remote controllable camera 108). The gesture-sensing device 106 is positioned to detect gestures performed by the user.

Referring to the embodiment as depicted in FIG. 4, the telepresence apparatus 100 further includes a first auxiliary remote controllable camera 108A and a second auxiliary remote controllable camera 108B. Generally, the first auxiliary remote controllable camera 108A is configured to communicate (provide) ancillary information to the first computer assembly 102 (as depicted in FIG. 1, or the second computer assembly 202) in such a way that the ancillary information is receivable from the space (such as a sterile implant room, a surgical room, etc.) associated with the first physical site 101. The first auxiliary remote controllable laser pointer device 110A is configured to communicate with the first computer assembly 102 (as depicted in FIG. 1, or the second computer assembly 202) in such a way that that ancillary information (ancillary information) is provided to the space associated with the first physical site 101. The first auxiliary remote controllable camera 108A is positioned (is configured to be positioned) proximate to a first table 196. For instance, the first auxiliary remote controllable camera 108A may be mounted to a camera-support assembly (such as, a tripod assembly, etc.). The camera-support assembly may be positioned on or near the first table 196. It will be appreciated that the camera-support assembly may include a flexible structure or may include a ridged structure (or any combination thereof). The camera-support assembly may be fixedly clamped or connected to the table or other suitable structure. The camera-support assembly may be placed proximate to a top surface of the operating room table. It will be appreciated that the top of the operating room table is a sterile field, in which case the camera-support assembly is configured to be fixedly connected (clamped) to a lower part of the table, and the camera-support assembly extends upwardly as required (such as, about 24 inches, etc.) above the first table 196 (to be positioned in, for instance, an operating room) and/or about a distance (such as about 12 inches) back from a plane (working surface) of the first table 196. The second auxiliary remote controllable camera 108B is positioned proximate to a second table 197. For instance, the second auxiliary remote controllable camera 108B may be mounted to a camera-support assembly (such as, a tripod assembly, etc.). The camera-support assembly may be positioned on or near the second table 197. The first table 196 and the second table 197 may be positioned in the surgical room and/or any other room (such as, the sterile implant room, the sterilization room, etc.). Any number of the auxiliary remote controllable cameras may be utilized for the case where the remote controllable camera 108 does not have sufficient field of view (for covering a specific room, etc.). The first auxiliary remote controllable camera 108A includes a first auxiliary remote controllable laser pointer device 110A. The first auxiliary remote controllable camera 108A and the first auxiliary remote controllable laser pointer device 110A are configured to communicate with the telepresence apparatus 100 in such a way that ancillary information (either through audio or the other modules, animation, video, etc.) may be provided to the operating staff that are positioned in the sterile field and to the remotely-located technician (located in the second physical site 201, via the telepresence apparatus 100 as depicted in FIG. 1). The first auxiliary remote controllable camera 108A and the first auxiliary remote controllable laser pointer device 11A are configured to operate similar to the operations associated with the remote controllable camera 108 and the remote controllable laser pointer device 110. The second auxiliary remote controllable camera 108B includes a second auxiliary remote controllable laser pointer device 110B. The second auxiliary remote controllable camera 108B and the second auxiliary remote controllable laser pointer device 110B are configured to operate similar to the operations associated with the remote controllable camera 108 and the remote controllable laser pointer device 110.

FIG. 5 to FIG. 11 depict front views of embodiments of a user interface 212 of a second display system 204 of a second computer assembly 202, in which the second computer assembly 202 is configured to be network connectable with the first computer assembly 102 of the telepresence apparatus 100 of FIG. 1.

Figure 5:
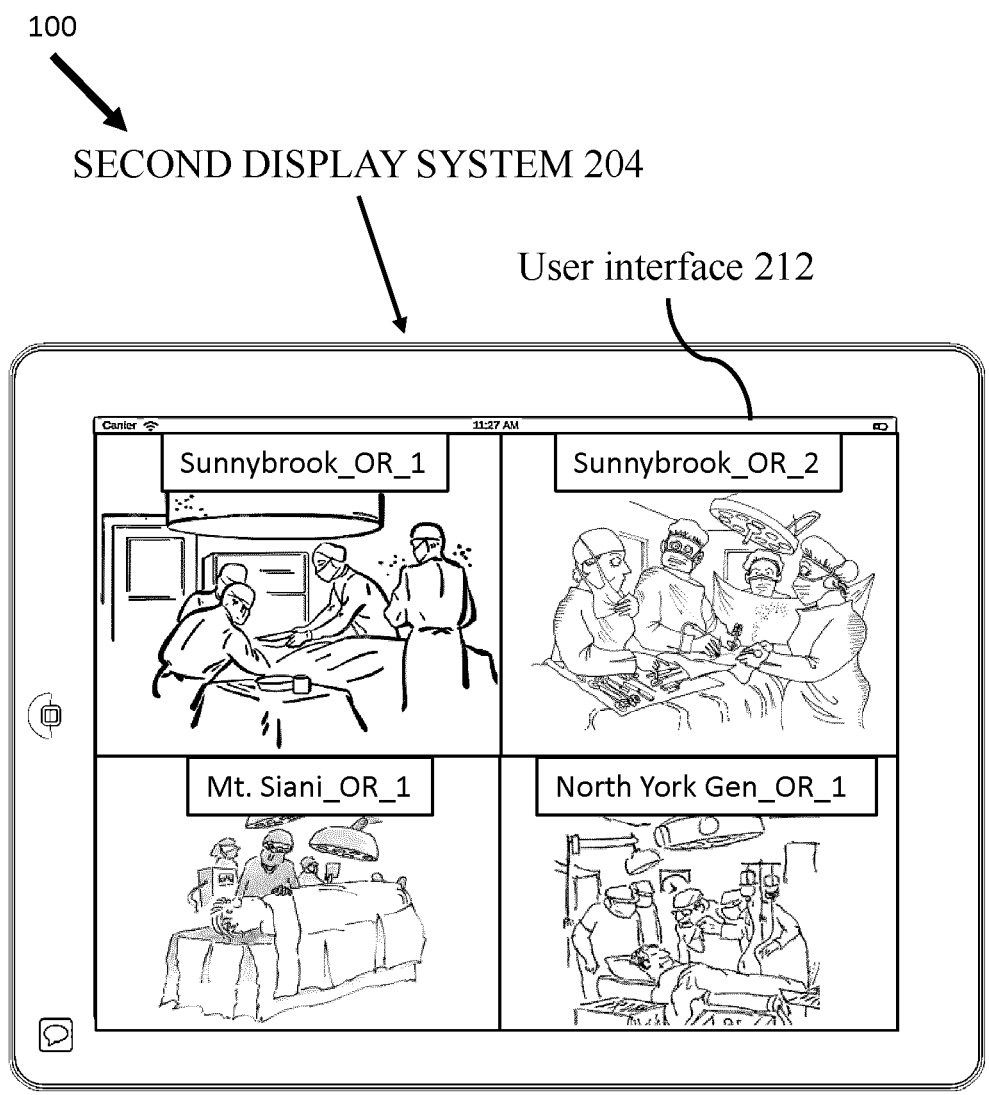
FIG. 5 to FIG. 11 depict front views of embodiments of a user interface of a second display system of a second computer assembly, in which the second computer assembly is configured to be network connectable with the first computer assembly of the telepresence apparatus of FIG. 1.

Referring to the embodiment as depicted in FIG. 5, a user interface 212 is shown on the second display system 204 of the second computer assembly 202. The user interface 212 allows a technician (located in the second physical site 201 depicted in FIG. 1) to view, simultaneously or near-simultaneously, visual data and/or audio data that is transmitted by respective instances of the first computer assembly 102 each of which are deployed in four or more separate (respective) physical locations. For instance, each of the respective instances of the first computer assembly 102 are deployed in a respective operating room in a specific hospital, such as (A) at Sunnybrook hospital in Sunnybrook operating room number one (Sunnybrook OR_1), (B) at Sunnybrook hospital in Sunnybrook operating room number two (Sunnybrook OR_2), (C) at Mount Sinai hospital in Mount Sinai operating room number one (Mt Sinai OR_1), and (D) at North York General hospital in North York General hospital operating room number one (North York Gen OR_1).

The second display system 204 includes a user interface 212 (such as a touchscreen, etc.) in such a way that the technician may interact with the second display system 204. The user interface 212 is configured to be responsive to the technician's touch in such a way that a specific display feed from a selected one of the respective instances of the first computer assembly 102 (located in the first physical site 101) may be selected for additional information and/or focus (by the technician). Other input methods may be used to navigate the user interface 212 (if so desired). For example, a mouse, trackpad, keyboard, trackball, or other input device may be used.

Figure 6:
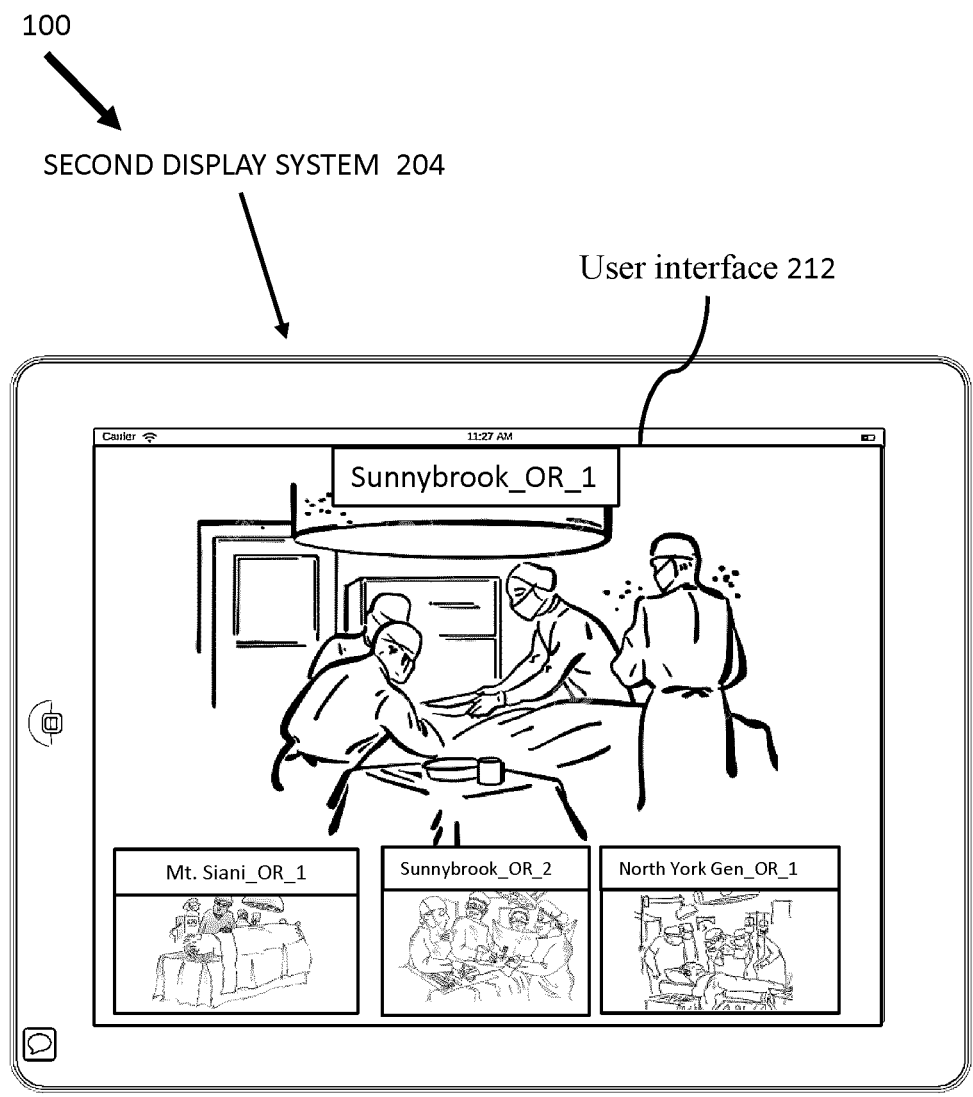

Referring to the embodiment as depicted in FIG. 6, the user interface 212 is shown to the technician (located in the second physical site 201 as depicted in FIG. 1) once a specific display feed is selected (by the technician) from among one of the first computer assemblies 102. The technician has selected a display feed from the first computer assembly 102 deployed (located) at Sunnybrook hospital operating room number 1 (Sunnybrook OR_1). This display feed may be zoomed-in on the second display system 204 in such a way that the display feed of Sunnybrook OR_1 takes up a significant portion of the display space on the second display system 204. The second display system 204 reduces and repositions the video feeds that are received from the remaining instances of the first computer assembly 102 (they are displayed near the bottom of the second display system 204). For instance, whatever operating room is "live" (that is, a medical procedure is active) may be clicked on (the display for that room may be clicked on), and may go to a full-screen view with the non-live operating rooms positioned in smaller displays but still visible (to the remote clinical expert). For instance, for the case where two or more hospitals need assistance at the same time, the system may be configured to transfer the request for service (the call) to the next available clinical expert running another secondary computer system, etc. The system may be configured to keep searching for a clinical expert until an available clinical expert is located, etc.

Referring to the embodiment as depicted in FIG. 6, the touchscreen of the second display system 204 is configured to allow the technician to select another display feed that is transmitted from a desired location (or instance, predetermined instance) of the first computer assembly 102. For the case where the technician desires to view the video feed (in greater detail) that is transmitted from Mount Sinai operating room number 1 (Mt Sinai OR_1) to the second display system 204, the technician may select the display feed icon for Mt Sinai OR 1. In response, the second display system 204 is configured to enlarge the Mt Sinai OR_1 video feed while reducing the current zoomed-in feed that is received from Sunnybrook OR_1. The previously zoomed-in video feed may then be reduced and positioned in such a way that the reduced video feed is displayed near the bottom of the second display system 204 of the second computer assembly 202.

Figure 7:
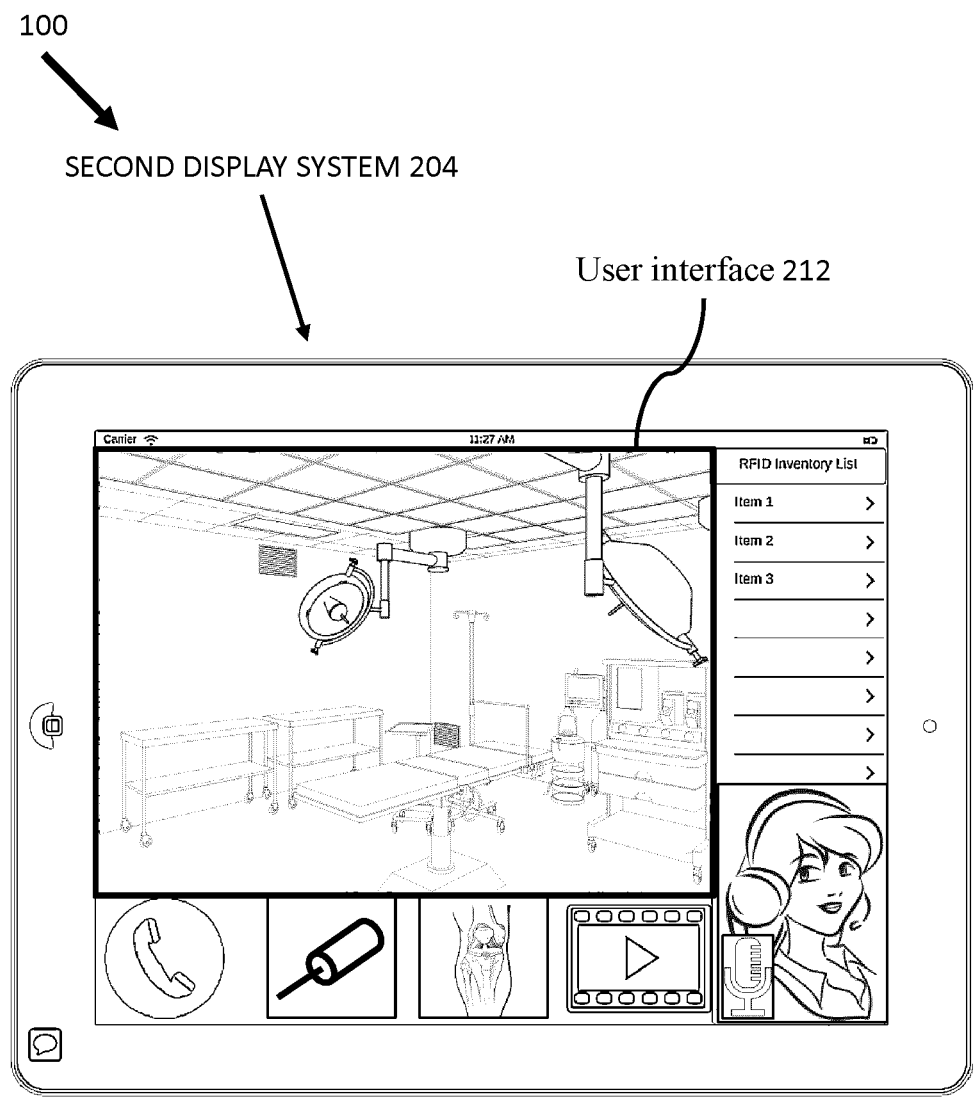

Referring to the embodiment as depicted in FIG. 7, the control options are displayed along the bottom right-hand side of the second display system 204 of the second computer assembly 202. The control options may be presented once the zoomed-in display feed on the first display system 104 (as depicted in FIG. 6) is clicked (a second time). Once the control options are displayed, the technician may use the second computer assembly 202 to control the first computer assembly 102 that corresponds to the zoomed-in display feed. The control options may be configured to (A) control for communicating with users of the first computer assembly 102, (B) control the movement of the first computer assembly 102, (C) control the remote controllable camera 108 (as depicted in FIG. 1), (D) control the remote controllable laser pointer device 110 (as depicted in FIG. 1), (E) maintain the first computer assembly 102 (as depicted in FIG. 1), or (F) control a function or an aspect of the first computer assembly 102 (that may be controllable remotely).

Figure 8:
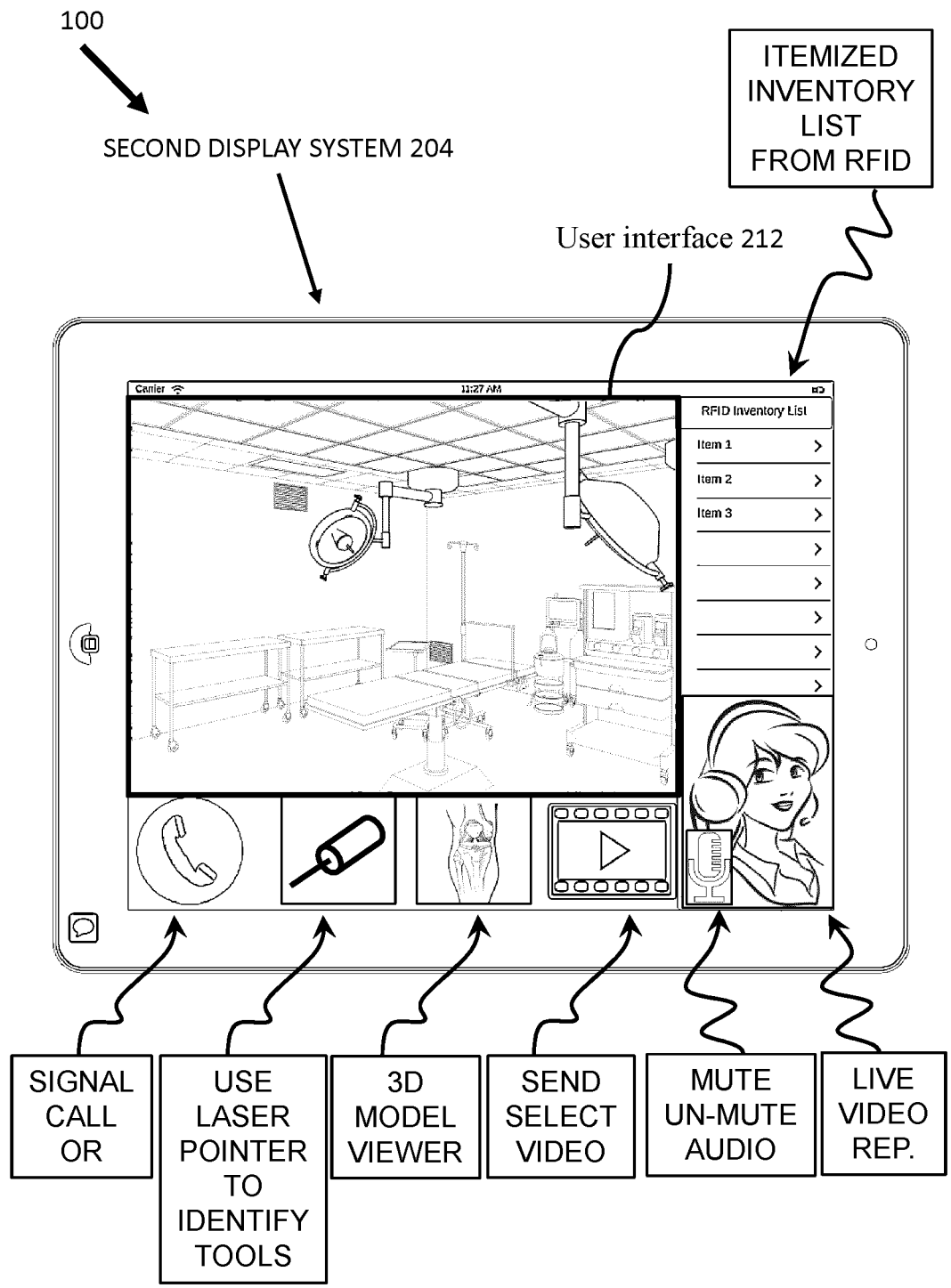

Referring to the embodiment as depicted in FIG. 8, the user interface 212 includes a subset of the control options. A video feed of the technician is provided in the lower right corner of the user interface 212. The technician may also mute and unmute a microphone associated with the technician from the video feed. Along the bottom section of the display feed of the second computer assembly 202, and proximate to the video feed of the technician, there are a series of four controls. The controls are configured to allow the technician to: (A) signal or call the operating room, (B) use the remote controllable laser pointer device 110 (as depicted in FIG. 1) to indicate a medical tool to a nurse, etc., (C) bring up a three-dimensional (3D) model or animation on a section of the first display system 104 and/or the second display system 204 and/or (D) select and/or send a video to the first display system 104 of the first computer assembly 102 located in the first physical site 101 such as the operating room (as depicted in FIG. 1). It will be appreciated that the controls may change depending on the circumstances and context in which the first computer assembly 102 is deployed and used. For instance, in an industrial training setting (such as, an automotive or aerospace repair facility) the controls may be different from those depicted. The main video feed of the first computer assembly 102 that is being controlled by the technician is shown to take up a larger portion of the second display system 204 (i.e., the zoomed-in portion) of the second computer assembly 202. The user interface 212 also includes a list of instruments that are available for the operating room team to use. This may include lists of 3D diagrams, animations, videos and/or lists of the various sites and auxiliary sites, etc. The medical instruments may be RFID tagged (Radio-Frequency Identification). The tagged medical instruments may be tracked by a RFID tracker (known and not depicted) that may be interfaced to the first computer assembly 102. Once tracked, these RFID tagged medical instruments may be listed in the user interface 212 (if desired). Sterile implants may be bar coded, in which case a scanner may be integrated to the system, and the scanner is configured to allow scanning of the implants for implant verification, sterility expiration, and/or automatic hospital reordering of implants.

Referring to the embodiment as depicted in FIG. 9, the user interface 212 is configured to display a main video feed of the first computer assembly 102, and the main video feed (received from the first computer assembly 102) takes up a relatively larger portion of the second display system 204 (i.e., the zoomed-in portion the second display system 204). The technician has selected the laser-pointer option located in the control options. The active and selected control option may be highlighted or otherwise distinguished from unselected and/or inactive control options. The laser pointer control option is highlighted to show that the laser pointer option has been selected.

Referring to the embodiment as depicted in FIG. 9, a pointer indicator (in this case, crosshairs) is displayed in the main video feed. The crosshairs indicate where the remote controllable laser pointer device 110 (as depicted in FIG. 1) is pointing. The software is configured to compute where (or more precisely what surgical instrument) the remote clinical expert is clicking on and to convert that to a signal that moves the laser pointer and has the remote controllable laser pointer device 110 (in use) point to the corresponding (actual) surgical instrument located on or near the operating room table. The technician may control the remote controllable laser pointer device 110 by clicking on a part of the video feed displayed on the user interface 212. Once clicked, the remote controllable laser pointer device 110 may move in such a way that the laser light from the remote controllable laser pointer device 110, in use, points to a location that (approximately) corresponds to the location indicated by the pointer indicator positioned on the user interface 212. Alternately, the technician may select one of the medical instruments on the instrument list on the right side of the screen of the user interface 212. Once the instrument is selected, the remote controllable laser pointer device 110 moves in such a way that the remote controllable laser pointer device 110, in use, points at the selected instrument located in the operating room (that is, in the first physical site 101 of FIG. 1). The remote controllable laser pointer device 110 may be configured to outline the selected instrument located in the operating room. The pointer indicator positioned on the user interface 212 may also be updated or computed to indicate the location that (approximately) corresponds to the location of the medical instrument (that is positioned in the operating room).

Figure 10:
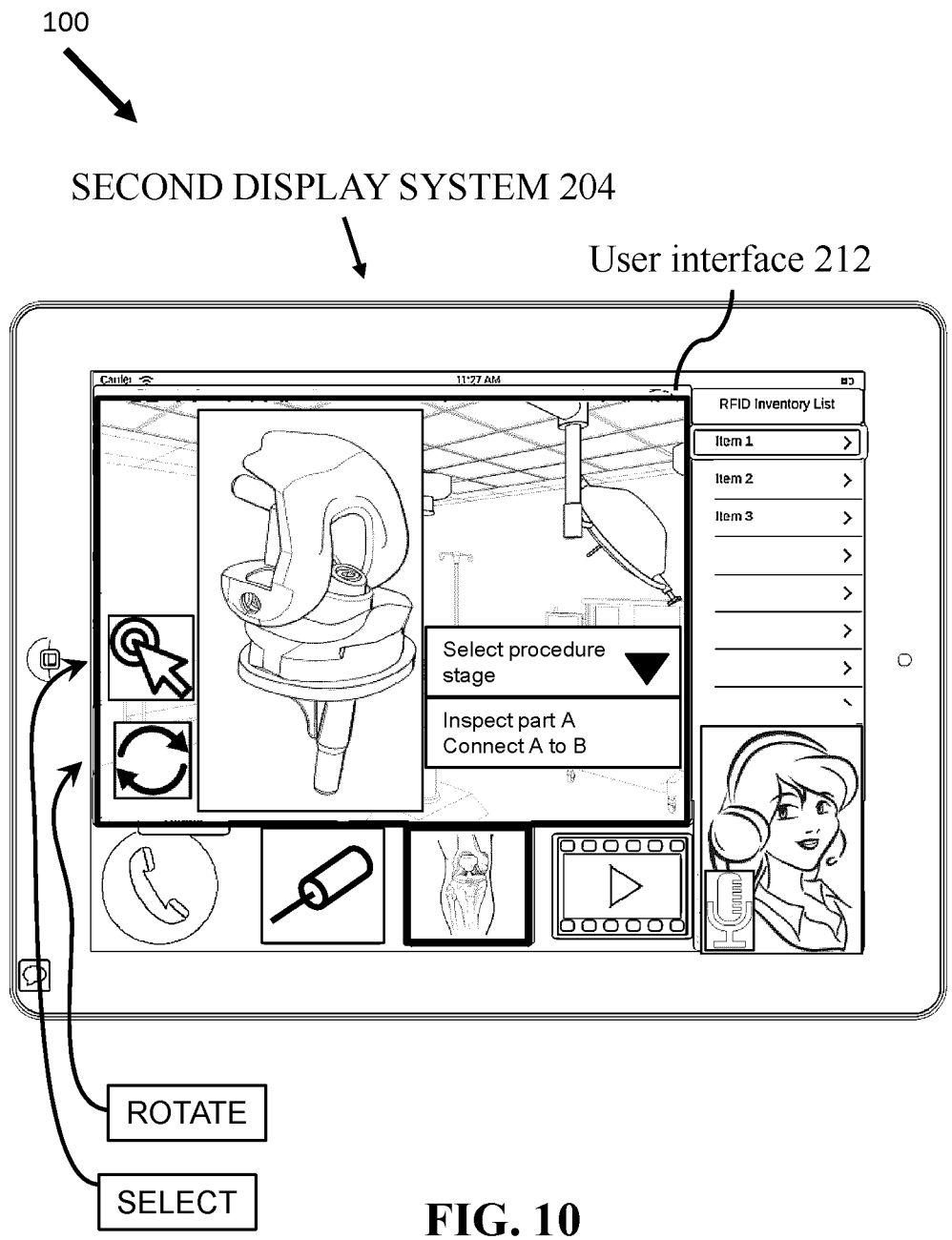

Referring to the embodiment as depicted in FIG. 10, the user interface 212 is configured to display a 3D (three-dimensional) model viewer control option (as shown by the highlighted control option panel). Once selected, a 3D view (three-dimensional view) of a model of an orthopedic device is displayed in a window panel of the user interface 212 (i.e., the component taking up the largest portion of the second display system 204 of the user interface 212). Once the technician selects the 3D model viewer, a corresponding 3D model viewer may be displayed on the first display system 104. Alternately, a 3D model viewer may not be displayed on the first display system 104 until the technician on the second computer assembly 202 activates the viewer accordingly. Once the 3D model viewer control option button has been selected, the previous contents of the main window (e.g., in FIG. 7, a video feed from the remote controllable camera 108 depicted in FIG. 1) are replaced with the 3D model viewer (a three-dimensional model viewer). The 3D model viewer allows a technician to rotate and/or select parts of the 3D model (three-dimensional model). Performing gestures on a touchscreen of the user interface 212 may cause the 3D image to rotate, move, zoom, etc. A corresponding movement is performed on the 3D image being displayed on the first display system 104 (as depicted in FIG. 1) in such a way that the operating-room staff may view the parts of the 3D model that the technician wishes the operating-room staff to view.

The user interface 212 may further include a drop-down list containing a list of animations (whether pre-rendered or rendered on-the-fly) related to the 3D model that is rendered in the 3D viewer (a three-dimensional model viewer). These animations may then be selected by the technician for playback on the first display system 104 (as depicted in FIG. 1). The drop-down list may allow the technician to select a pre-rendered animation that demonstrates, using the 3D model, how to assemble/disassemble/install the orthopedic device. This pre-rendered animation may then be performed using the first display system 104 and the first audio system 114 of the first computer assembly 102 in such a way that the users may be able to view the pre-rendered animation.

Figure 11:
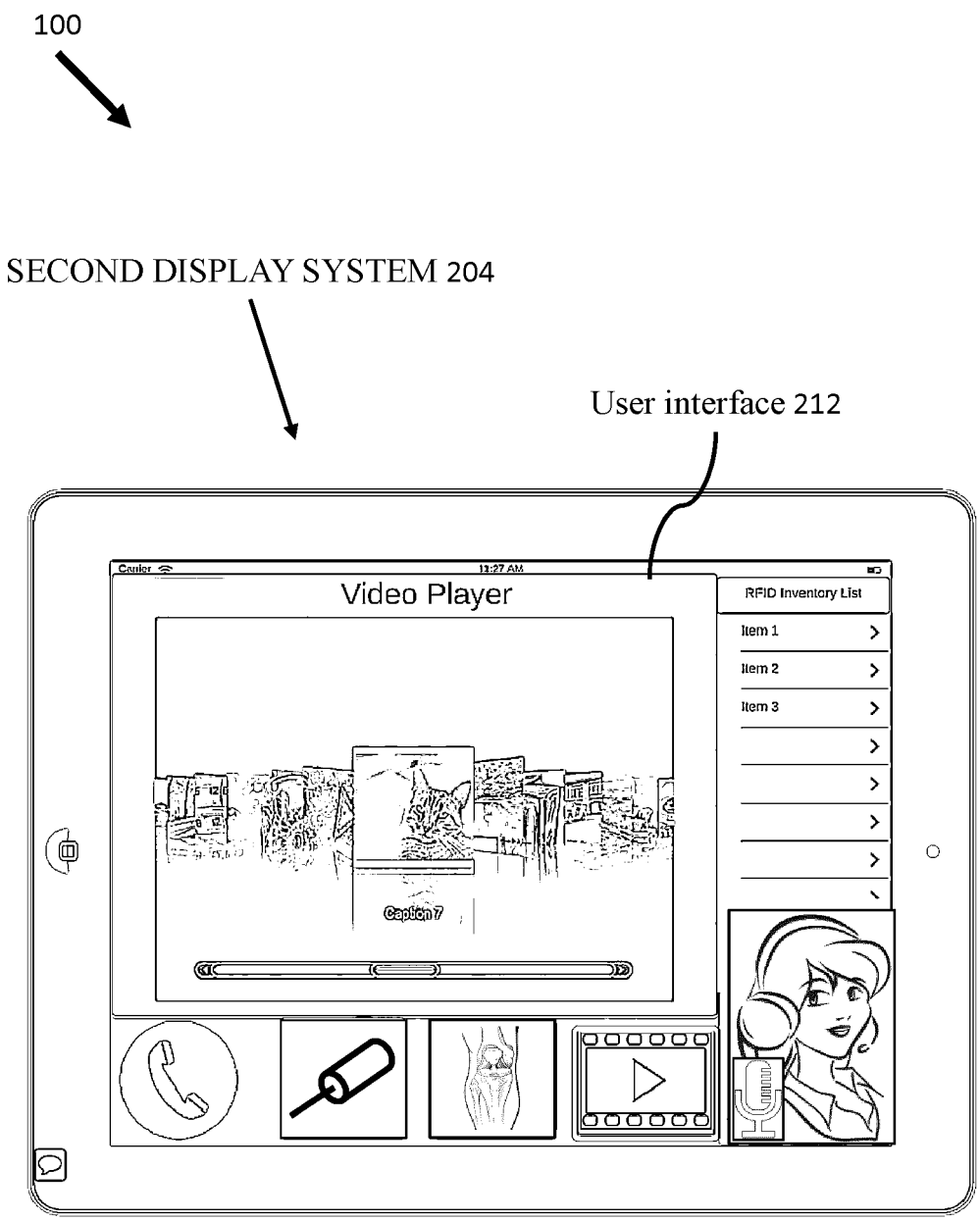

Referring to the embodiment as depicted in FIG. 11, the user interface 212 is configured to show (display) a video viewer control option (as shown by the highlighted control option panel). Once the technician selects the video viewer control option, a video gallery shows one or more pre-recorded videos. The technician may swipe left or right to find an appropriate video to play. Alternately, the technician may use the scrollbar to scroll amongst the pre-recorded videos. Once the desired pre-recorded video (predetermined pre-recorded video) is found, the technician may select it for playback on the first display system 104 of the first computer assembly 102 (as depicted in FIG. 1). The technician may click on the pre-recorded video in the center of the main window. The video may play both on the first display system 104 and the user interface 212 of the second display system 204 in such a way that both the technician (the clinical expert or surgical consultant) and the operating-room staff (surgical staff) may watch the same pre-recorded video.

WORKFLOW EXAMPLE 1

An exemplary workflow for using the telepresence apparatus 100 (as depicted in FIG. 1), from the perspective of a user of the first computer assembly 102 in an operating room environment, is provided. The operating-room staff moves the first computer assembly 102 into the surgical area, and are careful not to cross a sterile boundary. The first computer assembly 102 is activated. Once the first computer assembly 102 has completed the start-up procedure, the user performs a gesture in such a way that the gesture-sensing device 106, in use, may sense the gesture to start the gestural interface. The user performs a gesture associated with calling a remote technician in such a way that the gesture-sensing device 106, in use, senses the specific gesture and makes the call. Once the gesture has been detected by the gesture-sensing device 106, the first computer assembly 102 initiates bi-directional audio transmission and/or bi-directional video transmission between the first computer assembly 102 and the second computer assembly 202. Once the technician, located at the second computer assembly 202, accepts the transmission, the operating-room staff can hear and see the individual technical support technician on the first display system 104 and first audio system 114 of the first computer assembly 102 and begin (manage) a communications session with the second computer assembly 202 (via the second audio system 214).

Once communication has been established between the first computer assembly 102 and the second computer assembly 202, the operating-room staff may set up the sterile equipment and medical tools on a table located in the operating room. While the operating-room staff are setting up the equipment and medical tools, the technician, via the second computer assembly 202, may provide instructions to the operating-room staff (over the first audio system 114) and/or provide an image of the layout of the medical tools on the first display system 104 of the first computer assembly 102, etc. What is intended here is to display an image to the sterile surgical staff for suggesting the best way to set-up their various instrument trays.

The operating-room staff may ask questions about the medical procedure prior to the start of the surgical procedure. The technician, using the second computer assembly 202, may respond to these questions. For example, the technician may, using the remote controllable laser pointer device 110, direct various laser-pointer shapes to the individual medical tools positioned on the table while discussing these medical tools. The technician may also manipulate the remote controllable camera 108 to see different areas of the operating room. The technician may also play back animations and video for each medical tool to show the operating-room staff how the medical tool, medical devices, and medical instruments are to be used during surgery.

Once the operating-room staff's questions are answered, the operating-room staff may optionally perform a gesture associated with initiating a privacy screen (to block the video feed from reaching the second display system 204 located in the second physical site 201) in response to the gesture-sensing device 106 capturing the gesture (predetermined gesture).

For instance, the privacy feature may be primarily used for the case where the patient is being prepared for surgery as that is when the need for patient confidentiality is at its highest. During this time (preparation for surgery), it may still be beneficial to have audio communication with the surgical staff but not video communication. Once the patient is prepared and properly draped, the video communication may be re-established.

Once the gesture-sensing device 106 has captured the gesture from the operating-room staff, the first computer assembly 102 may initiate the privacy screen (that is, temporarily block or suspend the video feed and/or the audio feed to be sent to the second computer assembly 202 located in the second physical site 201). This may include muting the first audio system 114, turning off the remote controllable camera 108, altering the video feed captured by the remote controllable camera 108 to block certain parts or aspects of the video feed, or placing the first computer assembly 102 into a standby mode (pause mode), etc. During the medical procedure, once the operating-room staff requires input from the technician, the operating-room staff performs a gesture associated with disabling the privacy screen (and then the video and audio feed may resume). In accordance with an option, a predetermined gesture may be utilized to call up a menu or a video of the control gestures, and/or the predetermined gesture may be played (displayed) if required by the control-room (command-center) technician (worker) by (via) audio communication, etc. The gesture-sensing device 106 captures the predetermined gesture from the operating-room staff. Once the gesture is detected, the first computer assembly 102 reverses the steps that initiated the privacy screen. Once the privacy screen has been disabled, the technician and the operating-room staff may resume communications with each other.

The technician, through the second computer assembly 202, may also provide support to operating-room staff through any one or a combination of audio/video, directed laser pointing, bringing up documentation, and initiating video 3D animation playback to aid the operating-room staff in the current portion of the procedure.

Once the surgery is complete, the operating-room staff performs a gesture associated with disconnecting the communication (stopping the conference call or stopping any further connection with the second computer assembly 202). The gesture-sensing device 106 captures this predetermined gesture. Once the gesture is detected, the first computer assembly 102 disconnects the communication between the first computer assembly 102 and the second computer assembly 202. It will be appreciated that this workflow is for example purposes only and that other ways of using the system can be used without departing from the scope of this disclosure.

WORKFLOW EXAMPLE 2

The following is an operational workflow for using the telepresence apparatus 100 from the perspective of the technician using the second computer assembly 202.

The first computer assembly 102, once activated, wakes the second computer assembly 202. A representation of the first computer assembly 102 may be displayed as previously described in FIG. 5 or FIG. 6. Once a connection is established between the second computer assembly 202 and the first computer assembly 102 (located in one or more operating rooms), the technician selects the operating room she wishes to monitor. The technician does this by selecting the corresponding video feed or image displayed on the second display system 204 of the second computer assembly 202. The technician may select, via a drop-down menu displayed on the second display system 204, a medical procedure to be performed in the operating room that is being monitored. Once the user of the first computer assembly 102 initiates a call with the technician, bidirectional communication is established between the first computer assembly 102 and the second computer assembly 202. Once the bidirectional communication is established, the technician may view the operating room on the second display system 204. The technician may also be able to control the remote controllable camera 108, and may scan the room by panning/tilting and zooming the remote controllable camera 108 to focus on a table positioned in the first physical site 101, in which the medical tools are present.

In this example, the second display system 204 may include one or more contextual interfaces. These contextual interfaces show the necessary information, media, animation, etc., available to support the selected medical procedure (orthopedic procedure). The contextual interface may also include a tool layout function that may be displayed to the operating-room staff over the first display system 104 of the first computer assembly 102, to show the operating-room staff the preferred layout of the medical tools. If the operating-room staff move any of the medical tools to a different location, the technician may be able to update the second computer assembly 202 of the moved tool by moving a representation of the tool on the second display system 204 of the second computer assembly 202. This is so the location of the medical tools may be tracked. Preferably, a camera (configured to pan, tilt and zoom) may allow real time (near real time) tracking of the location of the surgical instruments in such a way that the remote controllable laser pointer device 110 may be utilized to highlight the surgical instruments when their location changes in the surgical field.

Once the preliminary inspection is complete, the operating-room staff may raise the privacy screen. The second computer assembly 202 may then update the second display system 204 to show the operating room as being in privacy mode. In this example, the video feed may be minimized.

Once the operating-room staff resumes the telepresence call, a connection between the first computer assembly 102 and the second computer assembly 202 is re-established. The technician may be alerted that the call has resumed. An audio alert may be played over the second audio system 214 of the second computer assembly 202. A flashing border around the video representation of the operating room may also be depicted on the second display system 204.

The technician selects the appropriate video representation of the operating room to focus on the selected connection. For the case where a touchscreen device is used, the technician may touch the video representation of the appropriate operating room. Once the operating room is selected, the second computer assembly 202 may control, at least in part, the first computer assembly 102 associated with that operating room. For example, the technician may now talk, direct the remote controllable laser pointer device 110 by touching the second display system 204, select pre-defined laser shapes to direct to the location being pointed to, and select documentation, images, video, animations and 3D models to present to the operating staff (on the first display system 104). The technician may also select bookmarks in the media (i.e., animations, pre-rendered animations, operating manuals, etc.,) to show particular parts of the medical procedure. The technician may also show non-bookmarked media to the operating-room staff. Once the operating-room staff are satisfied with the technician's response, the operating-room staff may then re-initiate the privacy screen (if desired). If the medical procedure has been completed, the operating-room staff may disconnect the call.

Common Remote Server

Both the first computer assembly 102 and the second computer assembly 202 may include software that operates automatically once the first computer assembly 102, the second computer assembly 202, or both are powered up. Once respective start-up procedures are completed, the first computer assembly 102 and the second computer assembly 202 may connect to a common remote server, and provide information regarding themselves to the server.

The first computer assembly 102 may query the server to determine whether any updates have been deployed since the first computer assembly 102 was last started. If so, the first computer assembly 102 may download and install the requisite updates. In some cases, the first computer assembly 102 contains the same set of pre-rendered video, pre-rendered animation, 3D models, manuals, etc. as the second computer assembly 202. This data may also be updated during the update process. Having this data stored locally on the first computer assembly 102 may be useful (rather than relying on network connections, which may be unreliable, and the information will already be available on the first computer assembly 102). This may mitigate the problems associated with slow or no network connections. Once the updates are completed, and the devices are registered on the server, the second computer assembly 202 may display the main interface to the technician. The technician may select, using the second display system 204 (such as a touchscreen device), a specific instance of the first computer assembly 102 corresponding to an operating room to monitor from the list of available instances of the first computer assembly 102 that are currently network connected to the server.

Once the technician has selected an instance of the first computer assembly 102 corresponding to an operating room to be monitored, the technician may select a specific medical procedure from a drop-down list. Once the medical procedure is selected, the relevant data is loaded from the database to the second computer assembly 202. It will be appreciated that the database may be physically located anywhere, such as in a cloud computing environment, etc.

The first computer assembly 102 may be configured to automatically scan for procedure-related objects once the technician has selected the specific procedure to be performed from a drop-down list. The remote controllable camera 108 may be configured to scan the room to identify any procedure-related objects. Preferably, the medical tools have unique markers, colors, barcodes, or other such identifiers. The video feed from the remote controllable camera 108 may be analyzed by the first computer assembly 102 to identify procedure-related objects. The location, position, and orientation data of the procedure-related objects may then be tracked by the first computer assembly 102. This data may be translated and transformed in such a way that the video representation of the operating room displayed on the second display system 204 is calibrated. The calibration effectively maps the image pixels on the second display system 204 to the real-world location of the procedure-related tool (located in the first physical site 101 of FIG. 1). The technician may be able to point to the specific medical instrument, using the remote controllable laser pointer device 110, by touching the mapped procedure-related tool on the interface displayed on the second display system 204 of the second computer assembly 202.

The remote controllable camera 108 and the remote controllable laser pointer device 110 may be calibrated with each other. For instance, the remote controllable camera 108 and the remote controllable laser pointer device 110 are operated, at least in part, independently (semi independently) of each other (to point the remote controllable camera 108 and the remote controllable laser pointer device 110 along individual or independent spatial directions or alignments). When the FOV (field of view) of the remote controllable camera 108 is changed, the calibration data for the remote controllable laser pointer device 110 may need to be updated (preferably, continuously every time the remote controllable camera 108 pans, tilts or zooms). A home position may be set to allow the remote controllable laser pointer device 110 to go back to the original calibration condition. This process may allow accurate pointing of the remote controllable laser pointer device 110 throughout the procedure.

For the case where the procedure-related medical tool is a medical toolbox, the technician, on the second computer assembly 202 may select a toolbox (on the second display system 204) to show an image to the operating room (on the first display system 104 of the first computer assembly 102) of the medical tools inside the tool box with a pre-defined image of the tools for visual inspection. It will be appreciated that the tool box may be called an instrument tray, and the tools may be called medical instruments.

In accordance with an option, the operating-room staff may be asked to wave a Radio Frequency ID (RFID) wand (a radio frequency identifier wand) over the medical toolboxes. The medical tools and toolboxes have predetermined RFID tags (radio frequency identifier tags) that identify the tool and toolbox. Waving the RFID wand reads these RFID tags, and may identify which toolboxes are available and which tools are contained within. This feature may be useful for verifying completeness of sterile implants (that is, all of the medical tools and instruments are accounted for). The IDs (radio frequency identifiers) of each toolbox and tool may then be communicated (wirelessly) to the first computer assembly 102, which then updates the database of tools on the server and/or the second computer assembly 202 or both. Any missing medical tool(s) may be clearly identified (that is, identified in a paper record, etc.).

For the case where the operating-room staff, via the first computer assembly 102, request assistance regarding a medical procedure, once the technician selects a form of media (e.g., pre-rendered video) for playback to the first computer assembly 102, a message is sent to the first computer assembly 102. The message, once received, is configured to cause the first computer assembly 102 to load the pre-rendered video (for example) from its local storage device. Once the pre-rendered video (for example) is loaded, the pre-rendered video is played back. The technician may then control the playback from the second computer assembly 202 as necessary (the appropriate video is communicated to the first computer assembly 102 which loads that video from its local data storage). The only information that needs to be transferred from the second computer assembly 202 to the first computer assembly 102 to initiate playback is the name and/or the identifier (ID) of the video and the timestamp and/or bookmark. Furthermore, in this embodiment, the technician may control playback/pause through onscreen controls which synchronizes with the first computer assembly 102. It will be appreciated that the playback of any media (such as, a pre-rendered 3D animation, presenting a document, etc.) may follow the above described pattern.

The first computer assembly 102, the second computer assembly 202, or the server (not shown and known) may be configured to record, archive, and otherwise save any and all data being transmitted between the first computer assembly 102 and the second computer assembly 202. This archived data may be later reviewed for quality assurance reasons. This data may also be used for training purposes. For example, an exemplary support session may be recorded in such a way that the session may be replayed for new technicians or the operating-room staff for training purposes.

In yet another embodiment, the telepresence apparatus 100 may allow another party to listen in to and/or view the communications between the first computer assembly 102 and the second computer assembly 202. This may be useful for supervisory or training purposes. The telepresence apparatus 100 may allow another party to join the call. That is, a third party, on a third computing device, may be able to connect to the ongoing call between the first computer assembly 102 and the second computer assembly 202. This may be useful for supervisory, training, or support services. For instance, a veteran technician may be permitted to join the ongoing call between the first computer assembly 102 and the second computer assembly 202 for the case where the technician on the second computer assembly 202 is unable to support the operating-room staff on the first computer assembly 102.

Database

The data center (also called a database, telepresence data, etc.) may be physically located with (on) (A) the command-center computer device, (B) the operating room computer device, (C) cloud storage (distributed networked storage), and/or (D) a data storage facility or a data-storage room (or in any combination and/or permutation thereof). The database may contain or include videos, training materials, audio information, etc. that is usable by the command-center computer device and/or the operating room computer device, etc. In accordance with an embodiment, both the first computer assembly and the second computer assembly have hard drives configured as data-storage devices for the database (configured to store training materials for offline or online training of surgeons, nurses and reps, either between surgeries or during the actual surgery). During a surgery, the surgeon (surgical staff) may access the training materials using the various gesture sensing technologies, etc. Alternatively, the training materials may be brought forward to the first computer assembly by the remote clinical expert located at the command-center when a need arises.

Computing Operations

It will be appreciated that a computing method includes an operating step of computing (by using a processor for the execution of computing operations) to provide a computing function and/or calculation (comparison, etc.). Computer hardware and other operating components suitable for performing the processes of the embodiments are not intended to limit the applicable environments. One of skill in the art will immediately appreciate that the embodiments of the invention can be practiced with other computer system configurations, including set-top boxes, hand-held devices, multiprocessor systems, microprocessor-based or programmable consumer electronics, network PCs, minicomputers, mainframe computers, and the like. The computer system may include, for instance, a processing unit, which may include a microprocessor such as the INTEL (TRADEMARK) PENTIUM (TRADEMARK) microprocessor, or the MOTOROLA (TRADEMARK) POWER PC (TRADEMARK) microprocessor, and any equivalent thereof. One of skill in the art will immediately recognize that the terms computer-readable medium and machine-readable medium may include any type of storage device that is accessible by a processor or by other data processing systems. A machine-readable storage medium may be embodied on a magnetic hard disk or an optical disk having executable instructions to cause a processor to perform a computing method (operational steps or computing operations).

Camera Options

In accordance with an embodiment, the operating room devices (that is, the devices positioned or located in, or proximate to, the operating room) include and are not limited to (comprise) the following devices: a first camera device, a second camera device, and a laser pointer device, etc., and any equivalent thereof.

In accordance with a preferred embodiment, the first camera device includes a pan-tilt-zoom camera (PTZ-operated camera) that is used for tracking (following) the laser light that becomes reflected from an object located in the operating room. The PTZ camera is controlled by the command-center computer via the network and via the operating room computer). The laser light is provided by, or generated by, the laser pointer device that is positioned in the operating room. The first camera device is configured to be controlled by the operator located in the command-center that is located remotely from the operating room (via the network, etc).

In accordance with a preferred embodiment, the first camera device is movable or orientable for pointing to (and/or also for focusing on) a specific object that is located or positioned in the operating room. The first camera includes a non-stationary (PTZ) camera (a pan-tilt-zoom camera). The first camera device (that is located in the operating room) is configured to be utilized by the user that is positioned in the command-center, and the first camera device is utilized in the computer process for tracking the laser spot (reflected light). It will be appreciated that viewing or watching is included in the meaning of tracking. It will be appreciated that the first camera device is configured to provide a field-of-view usable by the technician located in the command-center for controlling the orientation of the laser pointer (located in the operating room) by directing (aiming, re-positioning, pointing) the laser pointer at a specific object (located in the operating room within the field of view of the first camera device). The computer located in the command-center is configured to track and control (follow and locate) the position of the laser spot (the reflected laser light that is reflected from an object located in the operating room) by utilizing the PTZ camera located in the operating room. The laser light is to be generated by the laser pointer device (that is located in the operating room). The non-stationary (PTZ) camera is configured to view the laser light reflected from an object located in the operating room (in a field of view). The computer located in the command-center is configured to track (follow and/or locate) the reflected laser light. The non-stationary (PTZ) camera is configured to be controlled by the user located or positioned in the command-center, which is located remotely from the operating room. The first camera device is orientable and is configured to cooperate with a laser pointer device (a movable laser pointer) based on receiving, and acting on, orientation commands issued from the command-center via the network. The first camera device and the laser pointer device are both located in the operating room, and are controlled (via the network) by the user located in the command-center (also called the control-center).

In accordance with a preferred embodiment, the second camera device is configured to be stationary (that is, to be non-orientable or not to be aimed at any specific object located in the operating room). For instance, the second camera includes a depth-sensing camera (such as a RGB-D camera or a RGB-D depth-sensing camera, preferably fixed in position). The depth-sensing camera is configured for gesture recognition (that is, configured to recognize gestures initiated, or made, by the users, doctors, nurses, etc., who are located in the operating room). It will be appreciated that the gesture recognition operations (computing tasks or operations) may be performed, at least in part, by the depth-sensing camera, the computer device located in the operating room, and/or the computer device located in the command center. The depth-sensing camera includes, for instance, a processor unit. The depth-sensing camera (also called RGB-D camera) includes a depth-sensing device (also called a depth sensor) configured to cooperate (or cooperate in association) with a RGB-D camera (red-green-blue camera) or any equivalent thereof). The RGB-D camera is configured to augment a conventional image with depth information (related with the distance to the depth-sensing device) in a per-pixel basis. Preferably, the second camera (that is, the RGB-D depth-sensing camera) is utilized only for gesture recognition, and is not utilized for tracking the laser light reflected on an object located in the operating room. The second camera device is configured to be non-orientable or fixed. It will be appreciated that, in accordance with an embodiment, the position or orientation of the second camera is not coordinated with the position or orientation of the laser pointer device.

In accordance with an embodiment, a single camera assembly is configured for gesture recognition, and is also configured to provide a field of view usable for laser-light control (the single camera incorporates the functions of the first camera and the second camera in the single camera assembly).

In accordance with an embodiment, the operating room devices (that is, the devices positioned or located in, or proximate to, the operating room) include and are not limited to (comprise) the following devices: a first camera device, a second camera device, a third camera device, a laser pointer device (and in any combination or permutation thereof, and any equivalent thereof). The first camera device, the second camera device and the laser pointer device are as described above. The third camera device is configured to be pointed (aimed) at a surgical field, and thereby provide a field of view for access to relevant information that may be used by the remote clinical expert to ensure a successful surgical outcome. The surgical field (operating field or operative field) is an isolated area where surgery is performed; it must be kept sterile by aseptic techniques (also called surgical asepsis). The surgical field may include tables and equipment covered with sterile drapes and with all personnel being properly attired (for the operating room). The first camera device provides (is configured to provide) a field of view for the process of controlling the position of the laser light. The second camera device provides (is configured to provide) a second field of view for depth information for recognizing gestures (to be found in the operating room). The third camera device provides (is configured to provide) a field of view for the surgical field.

Smart Devices

It will be appreciated that any one or more of the first camera device, the second camera device, the third camera device, and the laser pointer device may be configured as (to be) a smart device. A smart device is an electronic device, generally connected to other devices or networks via different wireless protocols such as Bluetooth, NFC, Wi-Fi, 3G, etc., that can operate to some extent interactively and autonomously. The smart device has a processor that may perform functions (computations), thereby reducing the computation burden, to some extent, placed on the first computer device and/or the second computer device.

Location (Position) of Devices

It will be appreciated that the devices (such as, the camera, the laser pointer, computer device, etc.) may be configured to be stationary (configured to remain in place and not to be moved), or may be configured to be movable (positionable) to a desired position located within the operating room and/or in the command-center, etc.

Medical Signal from Operating Room

For the case where an operating-room equipment (such as, an X-ray machine, etc.) is configured to provide a medical signal (such as, a video output signal), the medical signal (originating in the operating room) may be received by the operating-room computer, and may be subsequently conveyed to the command-center (such as, to the command-center computer, via the network). Alternatively, the medical signal may be received by an auxiliary computer (located in the operating-room computer), and may be subsequently conveyed to the command-center computer (via the network). Alternatively, the medical signal may be received by an auxiliary computer (located in the operating-room computer), and may be subsequently conveyed to another auxiliary computer located in the command-center (via the network).

Visual Privacy and Audio Privacy

It will be appreciated that the following describes the privacy modes utilized by the computing system located in the operating room: (A) visual privacy mode (independent of audio privacy mode), in which the visual information is prevented from being transmitted to the command center, (B) audio privacy mode (independent of visual privacy mode), in which the audio information is prevented from being transmitted to the command center, and (C) visual and audio privacy mode, in which case both visual and audio information are prevented from being transmitted to the command center. The privacy modes may be enabled and disabled by the operating room attendees, such as nurses, etc., (once the operating-room computer system receives a privacy mode command from the user located in the operating room). Attendees (users) located in the operating room are permitted to initiate and terminate any one of the privacy modes (as may be needed). The attendee, consultant, and/or user, located in the command-center, is not permitted to alter the privacy mode as set by the attendee, consultant, and/or user, located in the operating room.

The visual privacy mode includes (A) blocking the transmission (communication) of any visual data (information, images, etc.) from any camera device located in the operating room back to the display unit located in the remote site (command-center), (the video data is neither recorded by the operating-room computer nor transmitted back to the command-center computer) and (B) permitting the transmission of audio information from any microphone (that is, a listening device) located in the operating room to the speaker (that is, an annunciation device) located in the remote site (command-center).

The audio privacy mode includes (A) blocking the transmission of any audio data (information) from the microphone located in the operating room back to the speaker located in the remote site (the audio data is neither recorded by the operating-room computer nor transmitted back to the command-center computer), and (B) permitting the transmission of video information from any camera located in the operating room to the display unit located in the remote site.

The visual and audio privacy mode includes blocking the transmission of any audio data and any video data from the device (microphone and camera) located in the operating room back to the devices (speaker and the display unit), (the video and audio data are neither recorded by the operating-room computer nor transmitted back to the command-center computer) located in the remote site. The operating room attendees may choose to have all video and/or audio data recorded on the operating-room computer notwithstanding the status of any privacy mode.

Camera Devices

In accordance with an embodiment, the camera device includes any type of camera. For instance, the camera may include a pan-tilt-zoom (PTZ) camera, and any equivalent thereof. A pan-tilt-zoom camera (PTZ camera) is a camera that is configured for directional and zoom control (preferably by remote control). The preferred embodiment includes a pan-tilt-zoom (PTZ) camera device and a laser pointer device, in which these devices are configured to cooperate with each other (each device may be independently controllable and controlled). The pointing action of the laser pointer device is controlled by the command-center operator; once the operator sees the field of view of the camera device, the operator may issue control commands, via the command-center computer device, for positioning (orienting) the laser spot (laser light) in the operating room (the laser-pointer device is controlled via positioning commands issued from the command-center computer device, which is located in the command-center).

In accordance with an embodiment, the camera device includes any type of camera. For instance, the camera may include an omnidirectional camera (and any equivalent thereof) having a 360-degree field of view (FOV) in the horizontal plane, or with a visual field that covers (approximately) the entire sphere. For instance, a 360 degree camera or 3D camera may be deployed in a storage facility or an implant storage room (or in the operating room, if required, etc.). A 3D camera is an imaging device that enables the perception of depth in images to replicate three dimensions as experienced through human binocular vision. Some 3D cameras use two or more lenses to record multiple points of view, while others use a single lens that shifts its position.

In accordance with an embodiment, a laser pointer device may include a laser pen, a laser diode module, etc., and any equivalent thereof. The laser pointer device is a device with a laser diode emitting a coherent laser beam of visible light. The laser pointer device may be configured to be used to highlight an object or area of interest (such as, the patient body, etc.) by illuminating the object/area with a bright spot or a laser spot of any type of color (or a non-colored light). It will be appreciated that the laser spot (also called a laser-reflection image) may be any light and/or colored light. It will be appreciated that the actual color of the light is not material. The brightness of the laser light may impact the ability for the camera device to find (sense) the laser spot. For instance, a green colored light may be used because there may be relatively more image resolution in the green channel of a CCD (charge-coupled device) utilized in a camera device, and humans are perceptually more tuned to sense a green colored light (versus other colors of light).

Kinetic Interface

In accordance with an embodiment, there is utilized a kinetic interface, such as using a hand-interface device, including a colored latex glove for the user positioned in the operating room to operate the operating-room computer system.

In accordance with an embodiment, there is utilized a non-kinetic interface, such as an audio command key word (keyword), including "SIRI", etc., followed by another audio command (such as ON, OFF, etc.) for the control of the operating-room equipment. SIRI voice recognition software is a TRADEMARK of APPLE INC. (registered in the U.S. and other countries). It will be appreciated that the word "SIRI" may be substituted with another word, such as "ROBOREP", etc.

In accordance with an embodiment, the gesture recognition interface is configured to interpret human gestures (kinetic gestures and/or audio gestures and/or visual gestures) via algorithms. For instance, gestures may originate from any bodily motion or state but commonly originate from the face or hand, and/or may include emotion recognition from face and hand gesture recognition. Users may use gestures to control or interact with devices without physically touching them. Gesture recognition interfaces enable humans to communicate with the machine HMI (human machine interface), and/or to interact (preferably, naturally) without any physical/mechanical contact with the machine HMI. The gesture recognition interface (such as a kinetic recognition interface) may include any one or more of the following: (A) a kinetic recognition interface (motion recognition interface) configured to facilitate the detection of user gestures (motions), such as (and not limited to) the RGB-D camera, etc., and a response to the gesture, (B) a voice recognition interface configured to facilitate detection of an audio input (a voice command input) and a response to the audio input, and/or (C) the detection of user gestures of (A) and the audio input of (B). The kinetic recognition interface is configured to track (follow) user movements and determine what gestures they may be performing (this may be achieved through various tools). The kinetic recognition interface allows users to interact with computing devices through the motion of objects and bodies. Preferably, the kinetic recognition interface does not require the user to hold anything or wear anything, and it is non-intrusive (such as the MICROSOFT (TRADEMARK) KINECT (TRADEMARK) recognition interface).

In accordance with an embodiment, the kinetic recognition interface does require the user to hold a device and/or wear a device, and it is intrusive (such as the NINTENDO (TRADEMARK) Wii (TRADEMARK) recognition interface system).

In accordance with an embodiment, there is provided a kinetic interface, including a hand interface such as a colored latex glove for the user to wear, for controlling or operating the system positioned in the operating room.

In accordance with an embodiment, the voice recognition interface (such as software) includes an intelligent personal assistant configured to utilize voice queries and a natural language user interface to answer questions, make recommendations, and/or perform actions by delegating requests to a set of services. The voice interface is configured to adapt to users' individual language usages. In accordance with another embodiment, the voice recognition interface is configured to be operated with an audio command keyword, such as "SIRI", followed by an audio command (ON/OFF, etc.) for control of the system located in the operating room. SIRI is a TRADEMARK of APPLE COMPUTER (TRADEMARK), located in the USA.

Artificial Intelligence

It will be appreciated that the computer system located in any one of (either one of) the operating room and/or the command-center may be programmed for artificial intelligence (AI, also machine intelligence, MI). AI is intelligence demonstrated by machines. In computer science, AI research is the study of "intelligent agents": any device that perceives its environment and takes actions that maximize its chance of successfully achieving its goals. The term "artificial intelligence" is applied when a machine mimics the cognitive functions that humans associate with other human minds, such as "learning" and "problem solving". Capabilities generally classified as AI may include successfully understanding human speech, interpreting complex data, including images and videos, reasoning, knowledge representation, planning, learning, natural language processing, perception, explainability (explainability is the state of being explainable), and/or the ability to move and manipulate objects. Artificial intelligence may include statistical methods, computational intelligence, search and mathematical optimization, neural networks, and methods based on statistics and probability.

Kinetic System

In accordance with an embodiment, the kinetic assembly includes a headset, a mixed reality headset, such as the MICROSOFT (TRADEMARK) HOLOLENS (TRADEMARK) device, a virtual reality headset, an augmented reality headset, and/or an augmented reality headset with holographic technology. The kinetic assembly is configured to be controllable by different user interfaces such as hand gestures, facial gestures, body gestures, eye gazes, and/or voice commands, etc., which permits the user to bridge the screen and physical space and extend the reality around them. For instance, the kinetic assembly may be configured to visualize a 3D model of the human body for reviewing potential surgical strategies. The mixed reality headset is configured to permit users to engage with digital content and interact with holographic objects thereby providing a mixed reality user experience. The definition of kinetic is relating to the motion of material bodies and the forces and energy associated therewith. The definition of Kinect is a device configured to add-on to the MICROSOFT (TRADEMARK) XBOX 360 (TRADEMARK) gaming system configured to enable users to control games, movies and music with physical motion or voice commands and without the need for a separate input controller like a joystick or keyboard. The controller-free gaming environment provided by the KINECT (TRADEMARK) system makes it possible for sensors to process basic gestures, facial characteristics, sounds and even full body motion activities such as jumping and kicking.

Laser Calibration

Figure 12:
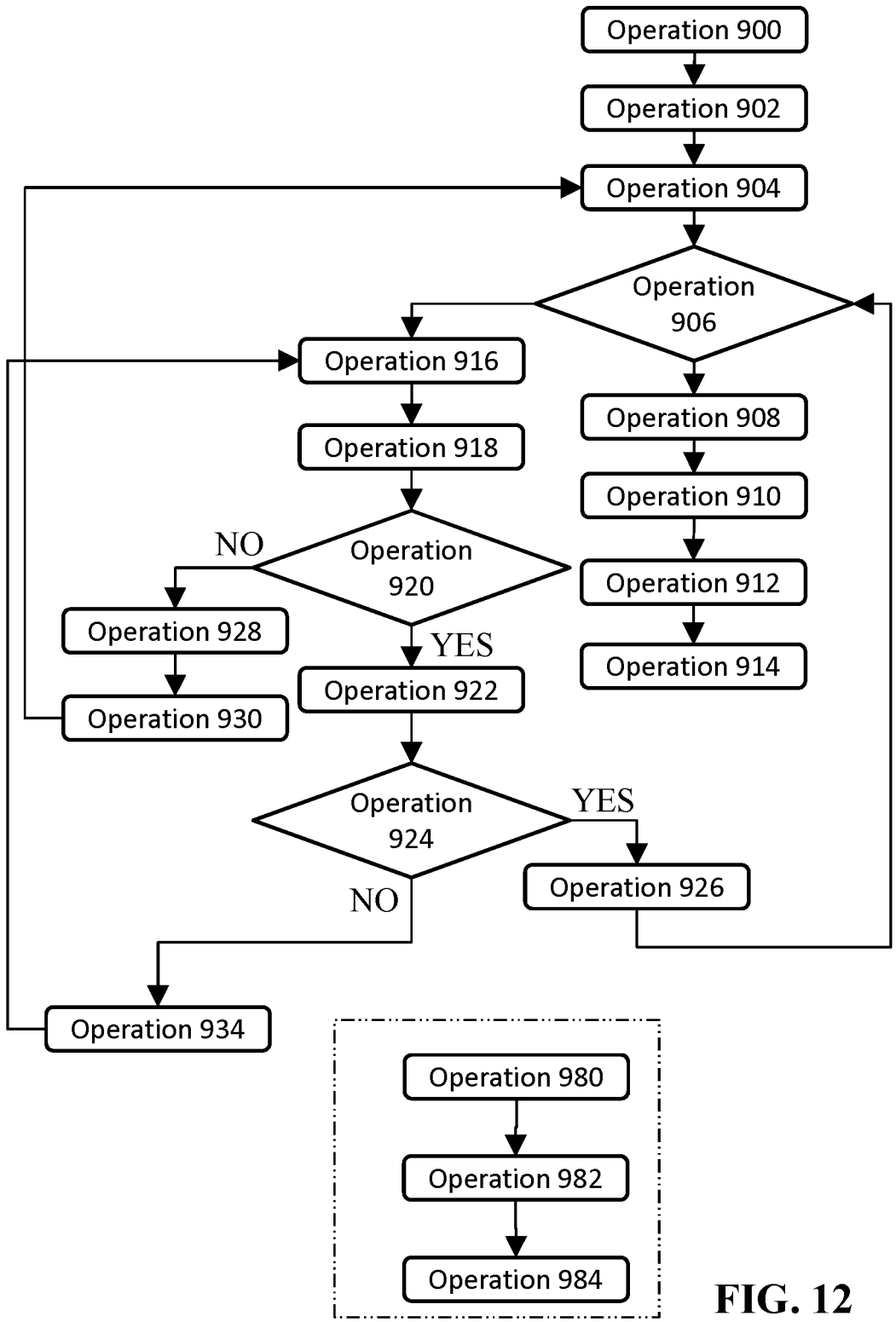
FIG. 12 depicts a flow chart of a calibration routine of the telepresence apparatus of FIG. 1.

FIG. 12 depicts a flow chart of a calibration routine of the telepresence apparatus of FIG. 1 (to be executed by the control-room computer).

It will be appreciated that it is within the scope of persons skilled in the art of computer vision technology to have the knowledge required to determine the manner in which to calibrate the spatial relationship between the laser light emission (emitted from a laser device) and the camera coordinates associated with a pixel position within an image (located on a display device of a control-room computer) of a table located in a room.

Calibration is performed so that the laser spot emitted from a laser may be movable once a user points and clicks a cursor (selects) on a desired pixel location (located on a display device of a computer).

Calibration of the laser pointer allows for accuracy, so that when the remote clinical expert uses his mouse to click on, for instance, an instrument or implant on the image of the operating room table, the motors of the laser pointer device will activate so that the laser pointer will highlight the correct object on the actual operating room table. The system maintains its calibration as the camera pans, tilts, and zooms by utilizing the feedback from the camera motors to know how far the camera has moved and the system makes adjustments accordingly.

The calibration process includes establishing a mapping (association) between image pixels (of a display connected to a computer) and a laser control parameter (such as, a laser control voltage of a motor of a laser pointer device). The laser pointer device includes, for instance, two motion-control motors (a first motion-control motor (first motor) for the X-direction, and a second motion-control motor (second motor) for the Y-direction). In accordance with an option, an optional lens may be placed in front of the laser egress to increase the field-of-view (FOV), if so desired.

The orientation (and control) of the camera device is adjustable (for angle, field-of-view (FOV), etc.) by the user located in the command-center. The frame of reference of the camera device changes once the camera device is re-oriented (the camera is made to be pointed or moved to view along another optical alignment or sight, so that another object may be viewed accordingly).

The orientation (controlled alignment) of the laser pointer device is calibrated by the user (via utilization of a user-control device such as the mouse) located at the command-center room (CC or remote site). The user may control (remotely control) the orientation of the laser pointer device that is positioned in the operating room (OR) so that the laser spot may be positioned in the operating room at a position desired by the user located in the command-center (also called the control-center room, the command-center room or the CC, etc.). The user utilizes the camera image to confirm that the laser spot (from the laser device) is, in fact, situated as required for the purposes of the user. The hardware set-up includes an operating-room computer, a camera device and a laser pointer device (all located in the operating room).

The system automatically updates to compensate for the system-controlled motion of the camera device by incorporating the current spatial data of the camera into the existing calibration. The current spatial data of the camera may be provided, for instance, by outputting the voltages of the control motors/encoders of the camera device, which may be inputted (read) by the system. The system thereby maintains the accuracy (within an acceptable tolerance) of positioning of the laser point so that, after the camera device has moved in response to instructions initiated by the user in the command-center (and received by the operating-room computer), the laser point (laser spot) will point at the correct items located in the operating room (medical instruments and/or implants on the operating room table). Preferably, the automatic update process is utilized for the case where the camera device is a PTZ camera (a movable camera).

Recalibration of the spatial position of the laser pointer may be necessary for the case where the distance [D] between the intended pixel location (the [S1] data) and the pixel location of the image of the actual laser points that were generated by the laser device (the [S2] data) is greater than desired (based on a comparison against a threshold). This recalibration condition, which requires user input, is likely to arise for the case where the physical location of the camera device and/or laser pointer device in the operating room is changed, or if the error on the calibration is too large due to insufficient resolution of the original X-Y calibration point.

Operations of FIG. 12 are described below from the point of view of operations to be executed by the operating-room computer located in the operating room. It will be appreciated that the calibration executable operations may be executable by either the operating-room computer located in the operating room or the command-center computer located in the command-center.

Referring to FIG. 12, operation 900 includes instructing (urging, controlling) the operating-room computer to start the calibration operation (routine or process). Operational control is transferred to operation 902 (once operation 900 is completed).

Operation 902 includes instructing (urging, controlling) the operating-room computer to control (via camera-control commands issued from the command-center computer under the direction of the user located in the command-center) the orientation (positional orientation or movement) of the camera device (located in the operating room, in which the camera device is connected to the operating-room computer). The command-center computer is configured to cooperate with the operating-room computer via a communication network. This is done in such a way that the camera device (located in the operating room), in use, views and captures the physical table (located in the operating room), and the table image (the virtual table) of the physical table is shown on the display device of the computer located in the command-center (and/or in the operating room).

Operation 902 also includes instructing (urging, controlling) the command-center computer (computer device) to receive the spatial data ([S1] positional data or [S1] position data) associated with the movement of a user-selection device (for instance, a mouse device) that is made to be moved over a surface or table surface (which is located in the command-center). The user-selection device is to be moved by the user (located in the command-center). The user (located in the command-center) selects (that is, points and clicks by utilizing the user selection device) a set of spaced-apart physical calibration points (the intended laser spot locations) that form, preferably, an outline (such as, the corners) of a calibration shape (such as, a rectangle formation or square formation). The spaced-apart physical calibration points (the [S1] position data points) are superimposed on the image of the operating room table (which is displayed in or on the display device located in the command center).

Operation 902 also includes instructing the command-center computer to issue commands to the operating-room computer to cause the laser pointer to emit a laser light to reflect on the physical operating-room table. Such laser light corresponds with each click of the user-selection device (the intended laser spot location). The operating-room computer captures the spatial data from each such laser light reflection (the data set formed by the laser light projections, the [S2] positional data or [S2] position data).

Operation 902 also includes instructing (urging, controlling) the operating-room computer to transmit the spatial data (the [S2] position data) to the command-center computer, and the command-center computer, in response, outputs the spatial data to a display device (located in the command-center). This is done in such a way that spaced-apart pixel calibration points (the [S2] position data points) are positioned on the virtual table image (as indicated on the display devices located in the command-center and/or the operating room). The spaced-apart pixel calibration points (the [S2] position data points) correspond with the set of spaced-apart physical calibration points formed from the corners of a rectangle (square) that was formed by the laser light projections on (located on) the physical table. The spaced-apart pixel calibration points (the [S2] position data points) are identified on the display by a cross or X formation displayed overtop of the virtual table image (as shown on the display device located in the command-center and/or the operating room). Operational control is transferred to operation 904 (once operation 902 is completed).

Operation 904 includes instructing (urging, controlling) the operating-room computer to wait for the command-center computer to respond to a user command (to be received from a user located in the command-center) for turning ON the laser pointer device. The command-center computer, in use, transmits (via the network) a laser control command to the laser pointer device located in the operating room. In this manner, the laser spot (that emanates from the laser pointer device that is located in the operating room) appears on the surface of the physical table (located in the operating room).

Operation 904 also includes instructing (urging, controlling) the operating-room computer to receive a control signal (via the network) from the command-center computer, in which the control signal is for instructing the operating-room computer to control the camera device (located in the operating room) to focus on the laser spot that is formed on the surface of the physical table that is located in the operating room (regardless of the focus quality for other items in the field of view of the camera device). Operational control is transferred to operation 906 (once operation 904 is completed).

Operation 906 includes instructing (urging, controlling) the operating-room computer to wait for the command-center computer to determine whether each of the acquired pixel coordinates for each of the spaced-apart calibration points have been processed (determining whether matrix [QimagePoints] is NOT empty).

For the case where matrix [QimagePoints] is NOT empty (TRUE), operational control is transferred to operation 916 (in which case processing of the next pixel calibration point is started). For the case where matrix [QimagePoints] is empty (FALSE), operational control is transferred to operation 908 (in which case each of the pixel calibration points has been processed).

Operation 908 includes instructing (urging, controlling) the operating-room computer to wait for the command-center computer to compute the homography between the laser voltages [V] (as found in matrix [ArrayLaserVoltage]) and the pixel calibration points (as found in matrix [ArrayImagePoint]). In projective geometry, a homography is an isomorphism of projective spaces, induced by an isomorphism of the vector spaces from which the projective spaces derive. It is a bijection that maps lines to lines, and thus a collineation. Homography is a function that transforms one planar region into another planar region, and thus, the application of a homography to a point will transform the point from one plane to the other plane (another plane). It will be appreciated that the equivalent of the concept of homography is "mapping". A preferred embodiment utilizes a planar surface, and a person skilled in the art would be able to utilize a non-planar method for mapping calibration points to laser voltages for computing the mapping between the laser voltages [V]. Operational control is transferred to operation 910 (once operation 908 is completed).

Operation 910 includes instructing (urging, controlling) the operating-room computer to obtain, and provide (via the network) to the command-center computer, the angles (the PTZ angles: pan, tilt, zoom) from the camera device (utilizing VISCA as a camera control protocol used with PTZ cameras, which was designed by SONY (TRADEMARK)). It will be appreciated that VISCA is an example of the protocol used, and that an equivalent of the VISCA camera may include a USB controlled camera using a different protocol for communication.

Operation 910 also includes instructing (urging, controlling) the operating-room computer to wait for the command-center computer to store the angle data in matrix [MatCalibrationPose]. Operational control is transferred to operation 912 (once operation 910 is completed).

Operation 912 includes instructing (urging, controlling) the operating-room computer to receive, from the command-center computer via the network, a camera reset command, and to execute the camera reset command on the camera device (located in the operating room) for resetting the camera capture settings (so that the camera device may detect the physical table located in the operating room). Operational control is transferred to operation 914 (once operation 912 is completed).

Operation 914 includes instructing (urging, controlling) the command-center computer to store the calibration homography that was computed for future use by the command-center computer to transform future user clicks into laser control voltages.

Operation 914 also includes instructing (urging, controlling) the operating-room computer to receive a stop calibration command (via the network) from the command-center computer, and to transfer operational control to other computer processes as required. Calibration is now complete and the system can resume functioning as designed.

Operation 916 includes instructing (urging, controlling) the operating-room computer to wait for the command-center computer to read (retrieve) the pixel calibration point (pixel position located in the image as shown on the display device) from the memory device (the image point [I] from the matrix [QimagePoints]). Operational control is transferred to operation 918 (once operation 916 is completed).

Operation 918 includes instructing (urging, controlling) the operating-room computer to receive a laser pointer command signal (from the command-center computer via the network) for turning ON (engaging or powering) the laser pointer device so that the laser spot is formed on the surface of the physical table (located in the operating room).

Operation 918 also includes instructing (urging, controlling) the operating-room computer to wait for the command-center computer to determine (detect, attempt to detect) the laser X-Y position [L] (the X-Y pixel position of the laser spot as displayed in the display device) in the current (latest) camera image. Operational control is transferred to operation 920 (once operation 918 is completed).

Operation 920 includes instructing (urging, controlling) the operating-room computer to wait for the command-center computer to determine whether the laser spot was found in the image as shown on the display device. For the case where, NO, a laser spot is not found in the image, operational control is transferred to operation 928. For the case where, YES, a laser spot is found in the image, operational control is transferred to operation 922.

Operation 922 includes instructing (urging, controlling) the operating-room computer to wait for the command-center computer to calculate (compute) a distance [D] between the image point [I] (the pixel X-Y calibration position) and the laser X-Y position [L] (the laser pixel X-Y position). Operational control is transferred to operation 924 (once operation 922 is completed).

Operation 924 includes instructing (urging, controlling) the operating-room computer to wait for the command-center computer to determine whether the computed distance [D] is within an acceptable range (acceptable low range of error). For Operation 924, for the case where, YES, the range of error is sufficiently low, operational control is transferred to operation 926 (the pixel positions are very close and the computed distance [D] is near zero). For Operation 924, for the case where, NO, the range of error is not sufficiently low enough, operational control is transferred to operation 934 (the pixel positions are too far apart, and the computed distance [D] is too large).

Operation 926 includes instructing (urging, controlling) the operating-room computer to wait for the command-center computer to associate the first calibration [X-Y or x-coordinate and y-coordinate] pixel position with the laser voltage [V] (that is, the laser control voltage of the first motion-control motor (for the X-direction) and the laser control voltage of the second motion-control motor (for the Y-direction) of the laser pointer device).

Operation 926 also includes instructing (urging, controlling) the operating-room computer to wait for the command-center computer to write (store) the laser voltage [V] in array [ArrayLaserVoltage], and write (store) the image point [I] in array [ArrayImagePoint]. Operational control is transferred to operation 906 (once operation 926 is completed, so that another pixel calibration point may be processed).

Operation 928 includes instructing (urging, controlling) the operating-room computer to receive, and execute, a reset command signal (from the command-center computer via the network), in which the reset command signal is for resetting the camera capture settings (so that the camera device may detect and provide an image of the surface of the physical table). Operational control is transferred to operation 930 (once operation 928 is completed).

Operation 930 includes instructing (urging, controlling) the operating-room computer to wait for the command-center computer to display the intended X-Y pixel calibration points on the image as displayed on the display device (located in the command-center and/or the operating room).

Operation 930 also includes instructing (urging, controlling) the operating-room computer to wait for the command-center computer to highlight the intended X-Y pixel calibration point that could not be found (identified in operation 920) so that the user (located in the command-center) may select a new pixel calibration point (a replacement pixel calibration point).

Operation 930 also includes instructing (urging, controlling) the operating-room computer to wait for the user (located in the command-center) to click another pixel calibration point located on the surface of the virtual table (in place of the pixel calibration point that could not be identified in operation 920). The user (located in the command-center) then selects (that is, points and clicks by utilizing the user selection device) a replacement pixel calibration point, which is then superimposed on the image of the operating room table (which is displayed in or on the display device located in the command center).

Once the replacement pixel calibration point is selected by the user, Operation 930 also includes instructing (urging, controlling) the command-center computer to add (write) a new X-Y pixel calibration point for replacement of the pixel calibration point that could not be identified in operation 920.

Operation 930 also includes instructing (urging, controlling) the operating-room computer to wait for the command-center computer to add (write) a replacement calibration point to matrix [QimagePoints].

Operation 930 also includes instructing (urging, controlling) the command-center computer to transmit the new X-Y pixel calibration point to the operating-room computer via the network. Operational control is transferred to operation 904 (once operation 930 is completed).

Operation 934 includes instructing (urging, controlling) the operating-room computer to wait for the command-center computer to adjust the laser voltage [V] (that is, the laser control voltage of the first motion-control motor (for the X-direction) and the laser control voltage of the second motion-control motor (for the Y-direction) of the laser pointer device) so that the laser spot is moved along the direction [D]. Operational control is transferred to operation 916 (once operation 934 is completed).

It will be appreciated that the calibration data may be utilized in the following manner (in the coded instructions) to assist the user (located in the command-center room) to move the laser spot of the laser pointing device (located in the operating room).

Operation 980 includes instructing (urging, controlling) the command-center computer to read the X-Y pixel position(s) in response to the user (located in the command-center room) selecting (with a mouse) a pixel position located on the images as shown in the display device (the user moves and clicks the mouse device that is positioned on the surface of the physical table, which is located in the command-center).

Operation 982 includes instructing (urging, controlling) the command-center computer to identify the motor voltages associated with the X-Y pixel positions (located on the physical table located in the command-center) as selected by the user (located in the command-center).

Operation 984 includes instructing (urging, controlling) the command-center computer to issue commands to the operating-room computer to apply the motor voltages (associated with the X-Y pixel positions as selected by the user located in the command-center) to the control motors of the laser pointer device (located in the operating room) so that the laser spot is moved by the laser pointer device (located in the operating room) to the X-Y pixel position located in the operating room (as selected by the user located in the command-center).

The following is offered as further description of the embodiments, in which any one or more of any technical feature (described in the detailed description, the summary and the claims) may be combinable with any another one or more of any technical feature (described in the detailed description, the summary and the claims). It is understood that each claim in the claims section is an open-ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the invention which does not materially modify the invention. Similarly, unless specifically made clear from its context, numerical values should be construed to include certain tolerances that the person skilled in the art would recognize as having negligible importance as they do not materially change the operability of the invention. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options would be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, un-recited elements or method steps. Comprising (comprised of) is an "open" phrase and allows coverage of technologies that employ additional, un-recited elements. When used in a claim, the word "comprising" is the transitory verb (transitional term) that separates the preamble of the claim from the technical features of the invention. The foregoing has outlined the non-limiting embodiments (examples). The description is made for particular non-limiting embodiments (examples). It is understood that the non-limiting embodiments are merely illustrative as examples.

What is claimed is:

1. A telepresence apparatus, comprising:
a first computer assembly configured to be network connectable with a second computer assembly via a communication network; and
the first computer assembly also configured to interface with a first memory assembly configured to tangibly store programmed coded instructions, in which the programmed coded instructions are configured to urge the first computer assembly to:
receive a user gesture signal from a gesture-sensing device, in which the gesture-sensing device is configured to be connectable to the first computer assembly, and in which the gesture-sensing device is also configured to detect a user gesture to be provided by a user positioned proximate to the first computer assembly, and in which the gesture-sensing device is also configured to generate the user gesture signal associated with the user gesture that was detected; and
compute whether the user gesture signal, which was received by the first computer assembly, matches a predetermined user gesture stored in the first memory assembly of the first computer assembly; and
compute whether to suspend transmission of an aspect of a telepresence data unit from the first computer assembly to the second computer assembly via the communication network depending on a match made between the user gesture signal and the predetermined user gesture; and
wherein:
an image of a medical instrument is configured to be displayed on a user interface of the second computer assembly; and
a remote controllable laser pointer device is configured to point at the medical instrument located proximate to the first computer assembly; and
a pointer indicator positioned on the user interface of the second computer assembly, in use, is updated to indicate a location that corresponds to the location of the medical instrument that is positioned proximate to the first computer assembly.

2. The telepresence apparatus of claim 1, wherein:
the second computer assembly is configured to be connectable to a camera controller system, and the camera controller system is configured to control a remote controllable camera, and the remote controllable camera is configured to be connectable to the first computer assembly, and the remote controllable camera is configured to be controllable by the camera controller system once the first computer assembly and the second computer assembly are network connected via the communication network; and
the second computer assembly is configured to be connectable to a laser pointer controller system, and the laser pointer controller system is configured to control a remote controllable laser pointer device, and the remote controllable laser pointer device is configured to be connectable to the first computer assembly, and the remote controllable laser pointer device is configured to be controllable by the laser pointer controller system once the first computer assembly and the second computer assembly are network connected via the communication network; and
the second computer assembly is configured to transmit, to the first computer assembly, camera-control instructions provided by the camera controller system, and to transmit laser-control instructions provided by the laser pointer controller system in such a way that:
the camera-control instructions and the laser-control instructions, in use, independently control the remote controllable camera and the remote controllable laser pointer device, respectively; and
the camera-control instructions and the laser-control instructions, in use, spatially orient the remote controllable camera and the remote controllable laser pointer device along different spatial orientations relative to each other.

3. The telepresence apparatus of claim 1, wherein:
the second computer assembly is configured to be connectable to a camera controller system, and the camera controller system is configured to control a remote controllable camera, and the remote controllable camera is configured to be connectable to the first computer assembly, and the remote controllable camera is configured to be controllable by the camera controller system once the first computer assembly and the second computer assembly are network connected via the communication network; and
the second computer assembly is configured to be connectable to a laser pointer controller system, and the laser pointer controller system is configured to control a remote controllable laser pointer device, and the remote controllable laser pointer device is configured to be connectable to the first computer assembly, and the remote controllable laser pointer device is configured to be controllable by the laser pointer controller system once the first computer assembly and the second computer assembly are network connected via the communication network; and
the second computer assembly is also configured to interface with a second display system; and
the second computer assembly is also configured to transmit, to the first computer assembly via the communication network, an image of a surgical instrument in such a way that the first computer assembly, in use, urges a first display system of the first computer assembly to display the image of the surgical instrument to a user that is positioned proximate to the first computer assembly; and
the second computer assembly is configured to transmit, to the first computer assembly via the communication network, laser-control instructions provided by the laser pointer controller system in such a way that the laser-control instructions, in use, urge the remote controllable laser pointer device to issue a light pattern, in which the light pattern, in use, identifies the surgical instrument to the user positioned proximate to the first computer assembly.

4. The telepresence apparatus of claim 1, wherein:
the first computer assembly includes:
a remote controllable laser pointer device configured to:
  receive laser-pointing instructions, via the communication network and the second computer assembly, from a laser pointer controller system of the second computer assembly; and
  point to a target located in a vicinity of the first computer assembly.

5. The telepresence apparatus of claim 4, wherein:
the remote controllable laser pointer device is configured to outline a medical instrument.

6. The telepresence apparatus of claim 1, wherein:
a user interface is provided on a second display system of the second computer assembly; and
the user interface is configured to allow a technician to use visual data and audio data that is receivable from instances of the first computer assembly of which are deployable in separate respective physical locations; and
the user interface is adapted to display a specific display feed from the first computer assembly that is selected for display.

7. The telepresence apparatus of claim 1, wherein:
control options are configured to be displayed on a second display system of the second computer assembly.

8. The telepresence apparatus of claim 7, wherein:
the control options are configured to provide control for:
exchanging communication with the first computer assembly; and
a remote controllable camera connected to the first computer assembly; and
a remote controllable laser pointer device connected to the first computer assembly.

9. The telepresence apparatus of claim 7, wherein:
the control options are configured to allow a technician to:
use a remote controllable laser pointer device to indicate a medical tool; and
bring up a three-dimensional model on a section of a user interface; and
select and send a video to a first display system of the first computer assembly.

10. The telepresence apparatus of claim 1, wherein:
a pointer indicator is configured to be displayed on a user interface; and
the pointer indicator is configured to indicate where a remote controllable laser pointer device is pointing; and
the remote controllable laser pointer device is configured to emit a laser to point to a location that corresponds to the location indicated by the pointer indicator positioned on the user interface.

11. The telepresence apparatus of claim 1, wherein:
a user interface is configured to display a control option for a three-dimensional model viewer, in which a three-dimensional view of a model of an orthopedic device is displayed, once selected, in a window panel of the user interface.

12. The telepresence apparatus of claim 1, wherein:
a user interface further includes a drop-down list containing a list of animations related to a three-dimensional model that is rendered in a three-dimensional model viewer.

13. The telepresence apparatus of claim 1, wherein:
the gesture-sensing device is configured to sense a gesture to start a call to the first computer assembly, and in response to the gesture being detected by the gesture-sensing device, the first computer assembly initiates a bi-directional audio transmission and a bi-directional video transmission between the first computer assembly and the second computer assembly.

14. The telepresence apparatus of claim 1, wherein:
the gesture-sensing device is configured to receive and detect performance of a gesture associated with initiating a privacy screen to block a video feed from reaching a second display system of the second computer assembly in such a way that the first computer assembly initiates the privacy screen to temporarily block suspension of the video feed or an audio feed to be sent to the second computer assembly.

15. The telepresence apparatus of claim 14, wherein:
the gesture-sensing device is configured to receive and detect performance of the gesture associated with disabling the privacy screen in such a way that the first computer assembly, in use, responds by reversing the privacy screen.

16. The telepresence apparatus of claim 1, wherein:
a microphone is operatively connected to the first computer assembly; and
the microphone and the first computer assembly are configured to receive from an audio signal associated with initiating a privacy screen to block a video feed from reaching a second display system of the second computer assembly in such a way that the first computer assembly initiates the privacy screen to temporarily block suspension of the video feed or an audio feed to be sent to the second computer assembly.

17. The telepresence apparatus of claim 1, further comprising:
a first auxiliary remote controllable camera configured to communicate with the first computer assembly; and
a first auxiliary remote controllable laser pointer device configured to communicate with the first computer assembly.

18. The telepresence apparatus of claim 1, wherein:
the first computer assembly is configured to scan for procedure-related objects once a specific procedure is to be performed from a drop-down list; and
a remote controllable camera is configured to scan a vicinity of the first computer assembly to identify any of the procedure-related objects; and
the first computer assembly is configured to track location, position, and orientation data of the procedure-related objects in such a way that:
  the location, the position, and the orientation data are displayed on a second display system; and
  a medical instrument is selectable by a remote controllable laser pointer device by touching a mapped procedure-related tool that is displayed on the second display system of the second computer assembly; and
wherein:
the first computer assembly is configured to receive, from a radio frequency identifier wand, a radio frequency identifier of a medical tool; and the first computer assembly transmits the radio frequency identifier to the second computer assembly; and the second computer assembly, in response to receiving the radio frequency identifier from the first computer assembly, identifies whether the medical tool is missing.

19. A telepresence apparatus, comprising:

a first computer assembly configured to be network connectable with a second computer assembly via a communication network; and the first computer assembly also configured to interface with a first memory assembly configured to tangibly store programmed coded instructions, in which the programmed coded instructions are configured to urge the first computer assembly to:

receive a user gesture signal from a gesture-sensing device, in which the gesture-sensing device is configured to be connectable to the first computer assembly, and in which the gesture-sensing device is also configured to detect a user gesture to be provided by a user positioned proximate to the first computer assembly, and in which the gesture-sensing device is also configured to generate the user gesture signal associated with the user gesture that was detected; and compute whether the user gesture signal, which was received by the first computer assembly, matches a predetermined user gesture stored in the first memory assembly of the first computer assembly; and compute whether to suspend transmission of an aspect of a telepresence data unit from the first computer assembly to the second computer assembly via the communication network depending on a match made between the user gesture signal and the predetermined user gesture; and wherein:

the first computer assembly is configured to scan for procedure-related objects once a specific procedure is to be performed from a drop-down list; and a remote controllable camera is configured to scan a vicinity of the first computer assembly to identify any of the procedure-related objects; and the first computer assembly is configured to track location, position, and orientation data of the procedure-related objects in such a way that:

the location, the position, and the orientation data are displayed on a second display system; and a medical instrument is selectable by a remote controllable laser pointer device by touching a mapped procedure-related tool that is displayed on the second display system of the second computer assembly.

20. A telepresence apparatus, comprising:

a first computer assembly configured to be network connectable with a second computer assembly via a communication network; and the first computer assembly also configured to interface with a first memory assembly configured to tangibly store programmed coded instructions, in which the programmed coded instructions are configured to urge the first computer assembly to:

receive a user gesture signal from a gesture-sensing device, in which the gesture-sensing device is configured to be connectable to the first computer assembly, and in which the gesture-sensing device is also configured to detect a user gesture to be provided by a user positioned proximate to the first computer assembly, and in which the gesture-sensing device is also configured to generate the user gesture signal associated with the user gesture that was detected; and compute whether the user gesture signal, which was received by the first computer assembly, matches a predetermined user gesture stored in the first memory assembly of the first computer assembly; and compute whether to suspend transmission of an aspect of a telepresence data unit from the first computer assembly to the second computer assembly via the communication network depending on a match made between the user gesture signal and the predetermined user gesture; and wherein:

the first computer assembly is configured to receive, from a radio frequency identifier wand, a radio frequency identifier of a medical tool; and the first computer assembly transmits the radio frequency identifier to the second computer assembly; and the second computer assembly, in response to receiving the radio frequency identifier from the first computer assembly, identifies whether the medical tool is missing.

21. A method of operating a telepresence apparatus, the method comprising:

receiving, by a first computer assembly, a telepresence data unit, in which the telepresence data unit is provided by a remote controllable camera and a first audio system transmitting, from the first computer assembly, the telepresence data unit to a second computer assembly via a communication network, in which the first computer assembly is configured to: (A) be network connectable with the communication network, and (B) be network connectable with the second computer assembly, in which the second computer assembly being configured to be network connectable with the communication network, and in which the first computer assembly and the second computer assembly also being configured to be network connectable via the communication network; and receiving, by the first computer assembly, a user gesture signal from a gesture-sensing device, in which the gesture-sensing device is configured to be connected to the first computer assembly, and in which the gesture-sensing device is configured to: (A) detect a user gesture to be provided by a user positioned proximate to the first computer assembly, and (B) generate the user gesture signal associated with the user gesture that was detected; and computing, by the first computer assembly, whether the user gesture signal, which was received by the first computer assembly, matches a predetermined user gesture stored in a first memory assembly of the first computer assembly; and computing, by the first computer assembly, whether to suspend transmission of an aspect of the telepresence data unit to the second computer assembly via the communication network depending on a match made between the user gesture signal and the predetermined user gesture; and wherein:

an image of a medical instrument is configured to be displayed on a user interface of the second computer assembly; and a remote controllable laser pointer device is configured to point at the medical instrument located proximate to the first computer assembly; and a pointer indicator positioned on the user interface of the second computer assembly, in use, is updated to indicate a location that corresponds to the location of the medical instrument that is positioned proximate to the first computer assembly.

22. A telepresence apparatus, comprising:

a first memory assembly configured to:
  interface with a first computer assembly; and
  tangibly store programmed coded instructions, in which the programmed coded instructions are configured to urge the first computer assembly to:
    receive a telepresence data unit, in which the telepresence data unit is provided by a remote controllable camera and a first audio system; and
    transmit the telepresence data unit to a second computer assembly via a communication network, in which the first computer assembly is configured to: (A) be network connectable with the communication network, and (B) be network connectable with the second computer assembly, in which the second computer assembly being configured to be network connectable with the communication network, and in which the first computer assembly and the second computer assembly also being configured to be network connectable via the communication network; and
    receive a user gesture signal from a gesture-sensing device, in which the gesture-sensing device is configured to be connectable to the first computer assembly, and in which the gesture-sensing device is also configured to detect a user gesture to be provided by a user positioned proximate to the first computer assembly, and in which the gesture-sensing device is also configured to generate the user gesture signal associated with the user gesture that was detected; and
    compute whether the user gesture signal, which was received by the first computer assembly, matches a predetermined user gesture stored in the first memory assembly of the first computer assembly; and
    compute whether to suspend transmission of an aspect of the telepresence data unit to the second computer assembly via the communication network depending on a match made between the user gesture signal and the predetermined user gesture; and
  wherein:
    an image of a medical instrument is configured to be displayed on a user interface of the second computer assembly; and
    a remote controllable laser pointer device is configured to point at the medical instrument located proximate to the first computer assembly; and
    a pointer indicator positioned on the user interface of the second computer assembly, in use, is updated to indicate a location that corresponds to the location of the medical instrument that is positioned proximate to the first computer assembly.

* * * * *

UNITED STATES PATENT AND TRADEMARK OFFICE
CERTIFICATE OF CORRECTION

PATENT NO. : 10,798,339 B2
APPLICATION NO. : 16/616327
DATED : October 6, 2020
INVENTOR(S) : Steven Robert McMillan and Andrew Hogue Page 1 of 1

It is certified that error appears in the above-identified patent and that said Letters Patent is hereby corrected as shown below:

Related U.S. Application Data (60) should read:
Provisional application No. 62/519,374, filed on Jun. 14, 2017.

Signed and Sealed this
Tenth Day of November, 2020

Andrei Iancu
*Director of the United States Patent and Trademark Office*